(12) United States Patent
Nti-Addae et al.

(10) Patent No.: US 10,716,789 B2
(45) Date of Patent: *Jul. 21, 2020

(54) CO-CRYSTALS AND PHARMACEUTICAL COMPOSITIONS COMPRISING THE SAME

(71) Applicant: Vertex Pharmaceuticals Incorporated, Boston, MA (US)

(72) Inventors: Kwame Wiredu Nti-Addae, Wilmington, MA (US); Simon Adam O'Neil, Belmont, MA (US); Yuegang Zhang, Wayland, MA (US); Michael P. Waldo, Grafton, MA (US); Praveen Mudunuri, Waltham, MA (US); Bin Song, Belmont, MA (US); John Gregg Van Alsten, Framingham, MA (US); Mark Strohmeier, Arlington, MA (US); Kathy Stavropoulos, Quincy, MA (US); Irina Nikolaevna Kadiyala, Newton, MA (US); Mettachit Navamal, Belmont, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/038,696

(22) Filed: Jul. 18, 2018

(65) Prior Publication Data

US 2018/0325897 A1 Nov. 15, 2018

Related U.S. Application Data

(63) Continuation of application No. 15/130,266, filed on Apr. 15, 2016, now Pat. No. 10,039,761, which is a
(Continued)

(51) Int. Cl.
*A61K 31/506* (2006.01)
*C07D 401/14* (2006.01)
(Continued)

(52) U.S. Cl.
CPC .......... *A61K 31/506* (2013.01); *A61K 31/337* (2013.01); *A61K 31/5025* (2013.01); *A61K 31/513* (2013.01); *A61K 31/517* (2013.01); *A61K 31/555* (2013.01); *A61K 31/704* (2013.01); *A61K 31/7048* (2013.01); *A61K 33/24* (2013.01); *A61K 38/14* (2013.01); *A61K 39/39558* (2013.01); *A61K 45/06* (2013.01); *A61P 35/00* (2018.01); *C07B 59/002* (2013.01);
(Continued)

(58) Field of Classification Search
CPC .............. A61K 31/337; A61K 31/5025; A61K 31/506; A61K 31/513; A61K 31/517; A61K 31/555; A61K 31/704; A61K 31/7048; A61K 33/24; A61K 38/14; A61K 39/39558; A61K 45/06; A61P 35/00; C07B 2200/05; C07B 2200/13; C07B 59/002; C07C 55/14; C07C 63/08; C07D 401/14
See application file for complete search history.

(56) References Cited

U.S. PATENT DOCUMENTS 5,478,938 A 12/1995 Clemence et al.
5,571,506 A 11/1996 Regan et al.
(Continued)

FOREIGN PATENT DOCUMENTS

CA 2716898 9/2009
CN 102137854 7/2011
(Continued)

OTHER PUBLICATIONS

Childs et al., "The Salt-Cocrystal Continuum: The Influence of Crystal Structure on Ionization State," Molecular Pharmaceutics, vol. 4, No. 3, Apr. 2007 (pp. 323-338).
(Continued)

*Primary Examiner* — My-Chau T. Tran
(74) *Attorney, Agent, or Firm* — Dechert LLP; Andrea L. C. Reid

(57) ABSTRACT

The present invention relates to compositions and co-crystals each comprising a compound of formula I having the structure:

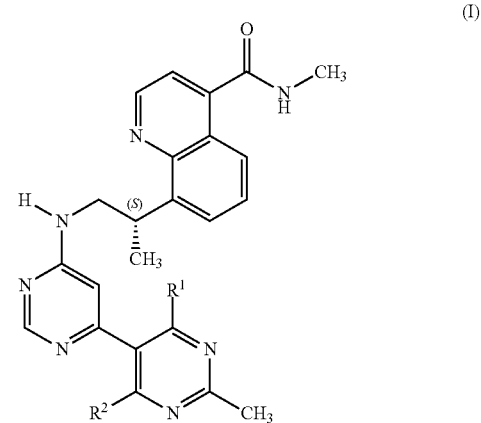

wherein each of $R^1$ and $R^2$ is H or $^2$H and a co-crystal former selected from adipic acid, citric acid, fumaric acid, maleic acid, succinic acid, or benzoic acid. Also within the scope of this invention are methods of making and using the same.

22 Claims, 19 Drawing Sheets

Related U.S. Application Data continuation of application No. PCT/US2014/061102, filed on Oct. 17, 2014.

(60) Provisional application No. 61/892,002, filed on Oct. 17, 2013.

(51) Int. Cl.

| | | |
|---|---|---|
| *A61P 35/00* | (2006.01) | |
| *A61K 31/337* | (2006.01) | |
| *A61K 31/5025* | (2006.01) | |
| *A61K 31/513* | (2006.01) | |
| *A61K 31/517* | (2006.01) | |
| *A61K 31/555* | (2006.01) | |
| *A61K 31/704* | (2006.01) | |
| *A61K 31/7048* | (2006.01) | |
| *A61K 33/24* | (2019.01) | |
| *A61K 38/14* | (2006.01) | |
| *A61K 39/395* | (2006.01) | |
| *A61K 45/06* | (2006.01) | |
| *C07B 59/00* | (2006.01) | |
| *C07C 55/10* | (2006.01) | |
| *C07C 55/14* | (2006.01) | |
| *C07C 57/145* | (2006.01) | |
| *C07C 57/15* | (2006.01) | |
| *C07C 59/265* | (2006.01) | |
| *C07C 63/08* | (2006.01) | |
| *C07K 16/28* | (2006.01) | |
| *A61N 5/10* | (2006.01) | |

(52) U.S. Cl.
CPC .............. *C07C 55/10* (2013.01); *C07C 55/14* (2013.01); *C07C 57/145* (2013.01); *C07C 57/15* (2013.01); *C07C 59/265* (2013.01); *C07C 63/08* (2013.01); *C07D 401/14* (2013.01); *C07K 16/2863* (2013.01); *A61N 2005/1098* (2013.01); *C07B 2200/05* (2013.01); *C07B 2200/13* (2013.01); *C07K 2317/24* (2013.01)

(56) References Cited

U.S. PATENT DOCUMENTS

| | | |
|---|---|---|
| 5,571,815 A | 11/1996 | Schaper et al. |
| 5,595,756 A | 1/1997 | Bally et al. |
| 5,668,140 A | 9/1997 | Schaper et al. |
| 5,723,461 A | 3/1998 | Rosner et al. |
| 5,977,117 A | 11/1999 | Chan et al. |
| 6,004,979 A | 12/1999 | Clemence et al. |
| 6,057,371 A | 5/2000 | Glennon |
| 6,222,073 B1 | 4/2001 | Herwig et al. |
| 6,265,428 B1 | 7/2001 | Chan et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,727,251 B2 | 4/2004 | Bebbington et al. |
| 6,743,791 B2 | 6/2004 | Cao et al. |
| 6,762,179 B2 | 7/2004 | Cochran et al. |
| 6,777,413 B2 | 8/2004 | Zhu et al. |
| 6,825,190 B2 | 11/2004 | Moon et al. |
| 6,844,347 B1 | 1/2005 | Schnidler et al. |
| 6,875,781 B2 | 4/2005 | Hong et al. |
| 6,884,804 B2 | 4/2005 | Choon-Moon |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,098,330 B2 | 8/2006 | Bebbington et al. |
| 7,115,739 B2 | 10/2006 | Bebbington et al. |
| 7,122,552 B2 | 10/2006 | Ledford |
| 7,144,911 B2 | 12/2006 | Flynn et al. |
| 7,179,912 B2 | 2/2007 | Halbrook et al. |
| 7,189,724 B2 | 3/2007 | An et al. |
| 7,208,507 B2 | 4/2007 | Hong et al. |
| 7,226,919 B2 | 6/2007 | Ledeboer et al. |
| 7,244,735 B2 | 7/2007 | Straub et al. |
| 7,253,187 B2 | 8/2007 | Cao et al. |
| 7,256,190 B2 | 8/2007 | Cochran et al. |
| 7,259,161 B2 | 8/2007 | Bethiel et al. |
| 7,271,179 B2 | 9/2007 | Bemis et al. |
| 7,300,929 B2 | 11/2007 | Baxter et al. |
| 7,304,061 B2 | 12/2007 | Hale et al. |
| 7,304,071 B2 | 12/2007 | Cochran et al. |
| 7,312,227 B2 | 12/2007 | Ledeboer et al. |
| 7,329,652 B2 | 2/2008 | Salituro et al. |
| 7,345,054 B2 | 3/2008 | Hale et al. |
| 7,358,258 B2 | 4/2008 | Hale et al. |
| 7,361,665 B2 | 4/2008 | Ledeboer et al. |
| 7,390,815 B2 | 6/2008 | Davies et al. |
| 7,407,962 B2 | 8/2008 | Aronov et al. |
| 7,419,984 B2 | 9/2008 | Bhatt et al. |
| 7,427,681 B2 | 9/2008 | Bebbington et al. |
| 7,452,555 B2 | 11/2008 | Childs |
| 7,456,190 B2 | 11/2008 | Maltais et al. |
| 7,473,691 B2 | 1/2009 | Davies et al. |
| 7,488,727 B2 | 2/2009 | Cochran et al. |
| 7,501,415 B2 | 3/2009 | Aronov et al. |
| 7,517,870 B2 | 4/2009 | Auricchio et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,592,340 B2 | 9/2009 | Bernis et al. |
| 7,625,913 B2 | 12/2009 | Bebbington et al. |
| 7,635,683 B2 | 12/2009 | Gai et al. |
| 7,666,895 B2 | 2/2010 | Flynn et al. |
| 7,691,853 B2 | 4/2010 | Bebbington et al. |
| 7,696,204 B2 | 4/2010 | McDonald et al. |
| 7,732,444 B2 | 6/2010 | Fleming et al. |
| 7,767,672 B2 | 8/2010 | Binch et al. |
| 7,820,685 B2 | 10/2010 | Binch et al. |
| 7,951,820 B2 | 5/2011 | Bebbington et al. |
| 7,968,565 B2 | 6/2011 | Arkin et al. |
| 7,982,037 B2 | 7/2011 | Bebbington et al. |
| 8,026,359 B2 | 9/2011 | Chen |
| 8,084,457 B2 | 12/2011 | Choidas et al. |
| 8,129,399 B2 | 3/2012 | Binch et al. |
| 8,268,811 B2 | 9/2012 | Mortimore et al. |
| 8,268,829 B2 | 9/2012 | Charrier et al. |
| 8,304,414 B2 | 11/2012 | Bebbington et al. |
| 8,372,850 B2 | 2/2013 | Jimenez et al. |
| 8,383,633 B2 | 2/2013 | Mortimore et al. |
| 8,410,133 B2 | 4/2013 | Jimenez et al. |
| 8,426,425 B2 | 4/2013 | Jimenez et al. |
| 8,455,500 B2 | 6/2013 | Okano et al. |
| 8,455,507 B2 | 6/2013 | Studley et al. |
| 8,476,287 B2 | 7/2013 | Okano et al. |
| 8,518,953 B2 | 8/2013 | Pierce et al. |
| 8,524,720 B2 | 9/2013 | Bebbington et al. |
| 8,541,428 B2 | 9/2013 | Gavish et al. |
| 8,546,392 B2 | 10/2013 | Hartmann et al. |
| 8,557,833 B2 | 10/2013 | Binch et al. |
| 8,563,549 B2 | 10/2013 | Burger et al. |
| 8,633,210 B2 | 1/2014 | Charrier et al. |
| 8,637,511 B2 | 1/2014 | Binch et al. |
| 8,664,219 B2 | 3/2014 | Jimenez et al. |
| 8,691,847 B2 | 4/2014 | Zhu et al. |
| 8,697,685 B2 | 4/2014 | Axten et al. |
| 8,697,698 B2 | 4/2014 | Bebbington et al. |
| 8,735,593 B2 | 5/2014 | Jimenez et al. |
| 8,779,127 B2 | 7/2014 | Charrier et al. |
| 8,784,782 B2 | 7/2014 | Tachdjian et al. |

(56) References Cited

U.S. PATENT DOCUMENTS

| | | | |
|---|---|---|---|
| 8,785,444 B2 | 7/2014 | Mortimore et al. | |
| 8,841,308 B2 | 9/2014 | Charrier et al. | |
| 9,062,076 B2 | 6/2015 | Williams et al. | |
| 9,296,701 B2 | 3/2016 | Charifson et al. | |
| 9,340,557 B2 | 5/2016 | Maxwell et al. | |
| 9,359,380 B2 | 6/2016 | Maxwell et al. | |
| 9,376,448 B2 | 6/2016 | Charifson et al. | |
| 9,592,232 B2 | 3/2017 | Charifson | |
| 9,878,993 B2 * | 1/2018 | Charifson | C07D 239/42 |
| 9,925,188 B2 * | 3/2018 | Charifson | C07D 403/14 |
| 10,039,761 B2 * | 8/2018 | Nti-Addae | C07D 401/14 |
| 2002/0111353 A1 | 8/2002 | Ledeboer et al. | |
| 2003/0096813 A1 | 5/2003 | Cao et al. | |
| 2003/0199525 A1 | 10/2003 | Hirst et al. | |
| 2003/0199526 A1 | 10/2003 | Choquette et al. | |
| 2003/0207873 A1 | 11/2003 | Harrington | |
| 2003/0207886 A1 | 11/2003 | Plucker et al. | |
| 2004/0097502 A1 | 5/2004 | Gellibert | |
| 2004/0235834 A1 | 11/2004 | Farmer et al. | |
| 2005/0054568 A1 | 3/2005 | Ling et al. | |
| 2006/0142572 A1 | 6/2006 | Martinez-Botella et al. | |
| 2006/0166936 A1 | 7/2006 | Binch et al. | |
| 2007/0179125 A1 | 8/2007 | Fraysse et al. | |
| 2007/0265263 A1 | 11/2007 | Cao et al. | |
| 2007/0270420 A1 | 11/2007 | Harbeson et al. | |
| 2008/0139585 A1 | 6/2008 | Rathinavelu et al. | |
| 2008/0207616 A1 | 8/2008 | Aquila et al. | |
| 2008/0267918 A1 | 10/2008 | Gai et al. | |
| 2008/0280891 A1 | 11/2008 | Kelly et al. | |
| 2009/0023729 A1 | 1/2009 | Nakamura et al. | |
| 2009/0053192 A1 | 2/2009 | Millan et al. | |
| 2009/0221581 A1 | 9/2009 | Wabnitz et al. | |
| 2009/0298844 A1 | 12/2009 | Pollard | |
| 2010/0137305 A1 | 6/2010 | Binch et al. | |
| 2010/0137337 A1 | 6/2010 | George et al. | |
| 2010/0197674 A1 | 8/2010 | Tamai et al. | |
| 2011/0046104 A1 | 2/2011 | Mortimore et al. | |
| 2011/0060013 A1 | 3/2011 | Mortimore et al. | |
| 2011/0065739 A1 | 3/2011 | Ishikawa et al. | |
| 2011/0144114 A1 | 6/2011 | Lochead et al. | |
| 2011/0275643 A1 | 11/2011 | Liou et al. | |
| 2011/0319618 A1 | 12/2011 | Nishio | |
| 2012/0009151 A1 | 1/2012 | Han et al. | |
| 2012/0202806 A1 | 8/2012 | Durrenberger et al. | |
| 2013/0012489 A1 | 1/2013 | Mederski et al. | |
| 2013/0150359 A1 | 6/2013 | Fuchss et al. | |
| 2013/0172337 A1 | 7/2013 | Fuchss et al. | |
| 2013/0209400 A1 | 8/2013 | Bach Tana et al. | |
| 2013/0281431 A1 | 10/2013 | Charifson et al. | |
| 2014/0045869 A1 | 2/2014 | Charifson et al. | |
| 2014/0113012 A1 | 4/2014 | Schultz et al. | |
| 2014/0148434 A1 | 5/2014 | Boyall et al. | |
| 2014/0187772 A1 | 7/2014 | Bebbington et al. | |
| 2014/0194444 A1 | 7/2014 | Jimenez et al. | |
| 2014/0256703 A1 | 9/2014 | Jimenez et al. | |
| 2014/0275024 A1 | 9/2014 | Maxwell et al. | |
| 2014/0275059 A1 | 9/2014 | Maxwell et al. | |
| 2014/0275072 A1 | 9/2014 | Mederski et al. | |
| 2015/0111871 A1 | 4/2015 | Charifson et al. | |
| 2016/0250212 A1 | 9/2016 | Charifson et al. | |
| 2016/0368899 A1 | 12/2016 | Charifson | |

FOREIGN PATENT DOCUMENTS

| | | |
|---|---|---|
| DE | 102006050512 | 4/2008 |
| DE | 102007044032 | 3/2009 |
| EP | 1678147 | 7/2006 |
| EP | 1701944 | 7/2009 |
| JP | H10-251255 | 9/1998 |
| JP | 2005336138 | 12/2005 |
| JP | 2007008045 | 1/2007 |
| JP | 2011246389 | 12/2011 |
| WO | WO-1993022291 | 11/1993 |
| WO | WO-1998037079 | 8/1998 |
| WO | WO-1998054158 | 12/1998 |
| WO | WO-2000009496 | 2/2000 |
| WO | WO-2000042026 | 7/2000 |
| WO | WO-2001027089 | 4/2001 |
| WO | WO-2001064646 | 9/2001 |
| WO | WO-2002020500 | 3/2002 |
| WO | WO-2004085418 | 10/2004 |
| WO | WO-2005026129 | 3/2005 |
| WO | WO-2005066139 | 7/2005 |
| WO | WO-2005089730 | 9/2005 |
| WO | WO-2005121121 | 12/2005 |
| WO | WO-2006044503 | 4/2006 |
| WO | WO-2006044732 | 4/2006 |
| WO | WO-2006108107 | 10/2006 |
| WO | WO-2006138418 | 12/2006 |
| WO | WO-2007056143 | 5/2007 |
| WO | WO-2007082899 | 7/2007 |
| WO | WO-2007109783 | 9/2007 |
| WO | WO-2008006583 | 1/2008 |
| WO | WO-2008008747 | 1/2008 |
| WO | WO-2008008852 | 1/2008 |
| WO | WO-2008028691 | 3/2008 |
| WO | WO-2008042639 | 4/2008 |
| WO | WO-2008070661 | 6/2008 |
| WO | WO-2008083346 | 7/2008 |
| WO | WO-2008092199 | 8/2008 |
| WO | WO-2008106202 | 9/2008 |
| WO | WO-2008115973 | 9/2008 |
| WO | WO-2008141065 | 11/2008 |
| WO | WO-2008144253 | 11/2008 |
| WO | WO-2008145616 | 12/2008 |
| WO | WO-2009004621 | 1/2009 |
| WO | WO-2009008991 | 1/2009 |
| WO | WO-2009016841 | 2/2009 |
| WO | WO-2009047359 | 4/2009 |
| WO | WO-2009105220 | 8/2009 |
| WO | WO-2009107391 | 9/2009 |
| WO | WO-2009109258 | 9/2009 |
| WO | WO-2009115517 | 9/2009 |
| WO | WO-2009152909 | 12/2009 |
| WO | WO-2010048149 | 4/2010 |
| WO | WO-2010064737 | 6/2010 |
| WO | WO-2010065899 | 6/2010 |
| WO | WO-2010093808 | 8/2010 |
| WO | 2011006074 | 1/2011 |
| WO | WO-2011022348 | 2/2011 |
| WO | WO-2011051535 | 5/2011 |
| WO | WO-2011113512 | 9/2011 |
| WO | WO-2012000632 | 1/2012 |
| WO | WO-2012028233 | 3/2012 |
| WO | 2012138938 | 10/2012 |
| WO | WO-2013024282 | 2/2013 |
| WO | WO-2013032951 | 3/2013 |
| WO | WO-2013040515 | 3/2013 |
| WO | WO-2013043935 | 3/2013 |
| WO | WO-2013049701 | 4/2013 |
| WO | WO-2013072015 | 5/2013 |
| WO | WO-2013083991 | 6/2013 |
| WO | WO-2013112950 | 8/2013 |
| WO | WO-2013163190 | 10/2013 |
| WO | WO-2014075077 | 5/2014 |

OTHER PUBLICATIONS

Davis et al., "Dynamics of the PI3K-like protein kinase members ATM and DNA-PKcs at DNA double strand breaks," Cell Cycle, vol. 9, No. 13, Jul. 2010 (pp. 2529-2536).

Edelman et al., "Targeted radiopharmaceutical therapy for advanced lung cancer: phase I trial of rhenium Re188 P2045, a somatostatin analog," Journal of Thoracic Cancer, vol. 4, No. 12, Dec. 2009 (pp. 1550-1554).

Goodwin et al., "Beyond DNA repair: DNA-PK function in cancer," Cancer Discovery, vol. 4, No. 10, Oct. 2014 (pp. 1126-1139).

Gura, "Systems for identifying new drugs are often faulty," Science, vol. 278, No. 5340, Nov. 1997 (pp. 1041-1042).

International Search Report and Written Opinion issued by the European Patent Office as International Searching Authority for International Application No. PCT/US2013/037811 dated Aug. 29, 2013 (10 pages).

(56) References Cited

OTHER PUBLICATIONS

International Search Report and Written Opinion issued by the European Patent Office as International Searching Authority for International Application No. PCT/US2014/024767 dated May 27, 2014 (10 pages).

International Search Report and Written Opinion issued by the European Patent Office as International Searching Authority for International Application No. PCT/US2014/061033 dated Dec. 22, 2014 (9 pages).

International Search Report and Written Opinion issued by the European Patent Office as International Searching Authority for International Application No. PCT/US2014/061102 dated Dec. 22, 2014 (10 pages).

Jordan, "Tamoxifen: a most unlikely pioneering medicine," Nature Reviews Drug Discovery, vol. 2, No. 3, Mar. 2003 (pp. 205-213).

Kashishian et al., "DNA-dependent protein kinase inhibitors as drug candidates for the treatment of cancer," Molecular Cancer Therapeutics, vol. 2, No. 12, Dec. 2003 (pp. 1257-1264).

Kuntziger et al., "Protein phosphatase 1 regulators in DNA damage signaling," Cell Cycle, vol. 10, No. 9, May 2011 (pp. 1356-1362).

Sporn et al., "Chemoprevention of cancer," Carcinogenesis, vol. 21, No. 3, Mar. 2000 (pp. 525-530).

Veuger et al., "Radiosensitization and DNA repair inhibition by the combined use of novel inhibitors of DNA-dependent protein kinase and poly(ADP-ribose) polymerase-1," Cancer Research, vol. 63, No. 18, Sep. 2003 (pp. 6008- 6015).

* cited by examiner

CO-CRYSTALS AND PHARMACEUTICAL COMPOSITIONS COMPRISING THE SAME

RELATED APPLICATIONS

This present application is a continuation of U.S. application Ser. No. 15/130,266, filed Apr. 15, 2016, which is a continuation of international PCT Application, PCT/US2014/061102, filed Oct. 17, 2014, which claims priority to U.S. Provisional Application No. 61/892,002 filed on Oct. 17, 2013, the entire contents of which are incorporated by reference herein.

TECHNICAL FIELD OF THE INVENTION

The present invention relates to co-crystals of DNA-dependent protein kinase (DNA-PK) inhibitors. The invention also provides pharmaceutical compositions thereof and methods of using the co-crystals and compositions in the treatment of cancer.

BACKGROUND OF THE INVENTION

Ionizing radiation (IR) induces a variety of DNA damage of which double strand breaks (DSBs) are the most cytotoxic. These DSBs can lead to cell death via apoptosis and/or mitotic catastrophe if not rapidly and completely repaired. In addition to IR, certain chemotherapeutic agents including topoisomerase II inhibitors, bleomycin, and doxorubicin also cause DSBs. These DNA lesions trigger a complex set of signals through the DNA damage response network that function to repair the damaged DNA and maintain cell viability and genomic stability. In mammalian cells, the predominant repair pathway for DSBs is the Non-Homologous End Joining Pathway (NHEJ). This pathway functions regardless of the phase of the cell cycle and does not require a template to re-ligate the broken DNA ends. NHEJ requires coordination of many proteins and signaling pathways. The core NHEJ machinery consists of the Ku70/80 heterodimer and the catalytic subunit of DNA-dependent protein kinase (DNA-PKcs), which together comprise the active DNA-PK enzyme complex. DNA-PKcs is a member of the phosphatidylinositol 3-kinase-related kinase (PIKK) family of serine/threonine protein kinases that also includes ataxia telangiectasia mutated (ATM), ataxia telangiectasia and Rad3-related (ATR), mTOR, and four PI3K isoforms. However, while DNA-PKcs is in the same protein kinase family as ATM and ATR, these latter kinases function to repair DNA damage through the Homologous Recombination (HR) pathway and are restricted to the S and $G_2$ phases of the cell cycle. While ATM is also recruited to sites of DSBs, ATR is recruited to sites of single stranded DNA breaks.

NHEJ is thought to proceed through three key steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-PKcs to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate re-ligation of the DNA ends.

It has been known for some time that DNA-PK$^{-/-}$ mice are hypersensitive to the effects of IR and that some non-selective small molecule inhibitors of DNA-PKcs can radiosensitize a variety of tumor cell types across a broad set of genetic backgrounds. While it is expected that inhibition of DNA-PK will radiosensitize normal cells to some extent, this has been observed to a lesser degree than with tumor cells likely due to the fact that tumor cells possess higher basal levels of endogenous replication stress and DNA damage (oncogene-induced replication stress) and DNA repair mechanisms are less efficient in tumor cells. Most importantly, an improved therapeutic window with greater sparing of normal tissue will be imparted from the combination of a DNA-PK inhibitor with recent advances in precision delivery of focused IR, including image-guide RT (IGRT) and intensity-modulated RT (IMRT).

Inhibition of DNA-PK activity induces effects in both cycling and non-cycling cells. This is highly significant since the majority of cells in a solid tumor are not actively replicating at any given moment, which limits the efficacy of many agents targeting the cell cycle. Equally intriguing are recent reports that suggest a strong connection between inhibition of the NHEJ pathway and the ability to kill radioresistant cancer stem cells (CSCs). It has been shown in some tumor cells that DSBs in dormant CSCs predominantly activate DNA repair through the NHEJ pathway; it is believed that CSCs are usually in the quiescent phase of the cell cycle. This may explain why half of cancer patients may experience local or distant tumor relapse despite treatment as current strategies are not able to effectively target CSCs. A DNA-PK inhibitor may have the ability to sensitize these potential metastatic progenitor cells to the effects of IR and select DSB-inducing chemotherapeutic agents.

Given the involvement of DNA-PK in DNA repair processes, DNA-PK inhibitory drugs may act as agents that enhance the efficacy of both cancer chemotherapy and radiotherapy. The present invention features crystalline compositions of DNA-PK inhibitors together with a co-crystal former (CCF), i.e., co-crystals. Compared to their free form(s), the co-crystals of the invention are advantageous as these compounds possess improved dissolution, higher aqueous solubility, and greater solid state physical stability than amorphous dispersions. The co-crystals described herein also provide a reduced volume of the dosage form and therefore lower pill burden since these co-crystals also exhibit higher bulk densities relative to amorphous forms. Further, the co-crystals of the invention provide manufacturing advantages relative to amorphous forms which require spray drying, lyophilization, or precipitation.

SUMMARY OF THE INVENTION

Figure 1:
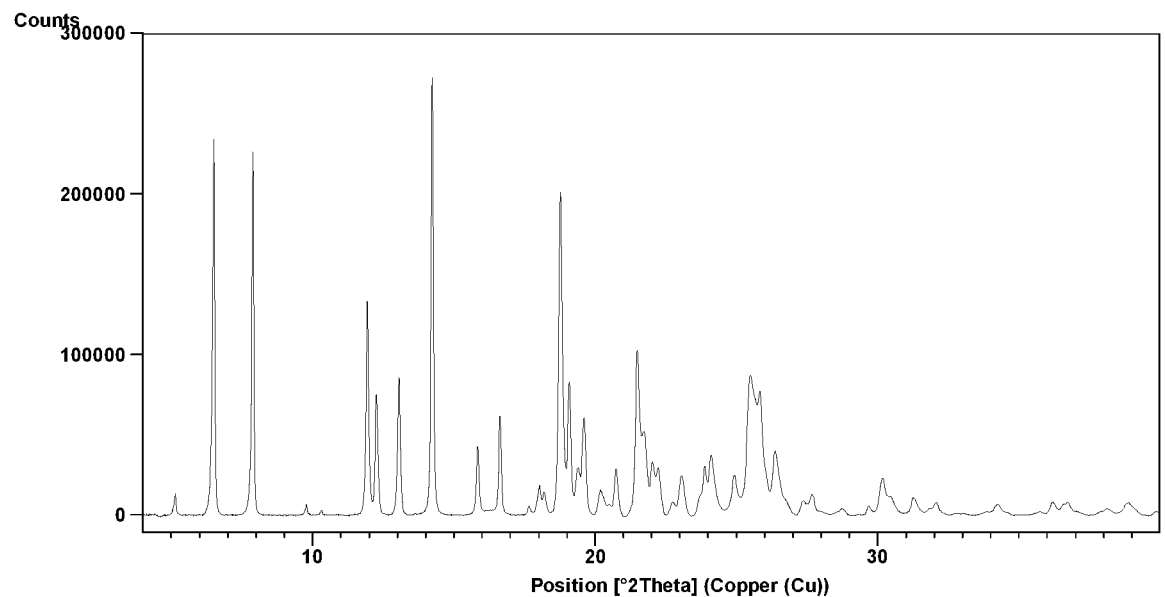
FIG. 1 shows an X-ray powder diffraction pattern of the co-crystal formed between Compound 1 with adipic acid.

In a first aspect, the invention features a co-crystal comprising a compound of formula I

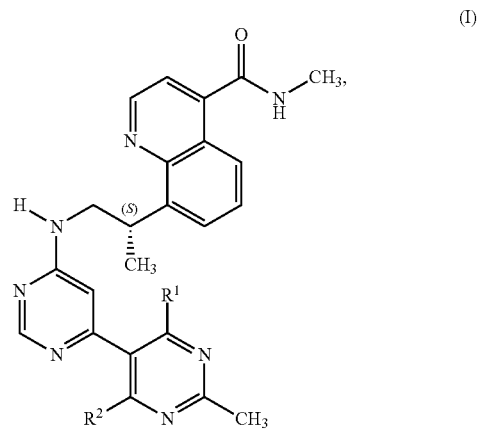

and a co-crystal former (CCF) selected from adipic acid, citric acid, fumaric acid, maleic acid, succinic acid, or benzoic acid, wherein each of $R^1$ and $R^2$ is hydrogen or deuterium.

In another aspect, the invention provides a pharmaceutical composition that includes a co-crystal of a compound of formula I described above. In one embodiment, the pharmaceutical composition further includes a diluent, solvent, excipient, or carrier.

In yet another aspect, the invention provides a eutectic solid composition comprising: (a) a co-crystal comprising a compound of formula (I) and a co-crystal former selected from adipic acid, wherein each of $R^1$ and $R^2$ is hydrogen or deuterium, and wherein the molar ratio of the compound of formula I to adipic acid is about 2 to 1; and (b) adipic acid. In yet another aspect, the invention provides a pharmaceutical composition comprising such a eutectic solid composition. In one embodiment, the pharmaceutical composition further includes a diluent, solvent, excipient, or carrier.

Another aspect of this invention provides a method of making a co-crystal of a compound of formula I and adipic acid, citric acid, fumaric acid, maleic acid, succinic acid, or benzoic acid. In one embodiment, the method comprises: providing the compound of formula I; providing the co-crystal former; grinding, heating, co-subliming, co-melting, or contacting in solution the compound of formula I with the co-crystal former under crystallization conditions so as to form the co-crystal in solid phase; and then optionally isolating the co-crystal formed thereby. In another embodiment, the method comprises mixing a compound of formula (I) with adipic acid, citric acid, fumaric acid, maleic acid, succinic acid, or benzoic acid at an elevated temperature to form the co-crystal. In some embodiments, the making a co-crystal of a compound of formula I and the CCF includes providing the compound of formula I and adipic acid, citric acid, fumaric acid, maleic acid, succinic acid, or benzoic acid in a molar ratio between about 1 to 1.2 to about 1 to 3.6, respectively.

In yet another aspect, the invention provides a method for modulating a chemical or physical property of interest (such as melting point, solubility, dissolution, hygroscopicity, and bioavailability) of a co-crystal containing a compound of formula I and adipic acid, citric acid, fumaric acid, maleic acid, succinic acid, or benzoic acid. The method includes the steps of measuring the chemical or physical property of interest for the compound of formula I and CCF; determining the mole fraction of the compound of formula I and CCF that will result in the desired modulation of the chemical or physical property of interest; and preparing the co-crystal with the molar fraction as determined.

The compositions and co-crystals of this invention can be used for treating diseases implicated by or associated with the inhibition of DNA-PK. In particular, the invention provides a method of sensitizing a cell to an agent that induces a DNA lesion comprising contacting the cell with a co-crystal of the invention or pharmaceutical composition thereof.

The invention further provides methods of potentiating a therapeutic regimen for treatment of cancer comprising administering to an individual in need thereof an effective amount of a co-crystal of the invention or pharmaceutical composition thereof. In one embodiment, the therapeutic regimen for treatment of cancer includes radiation therapy.

The present invention also provides methods of treating cancer in an animal that includes administering to the animal an effective amount of a co-crystal or pharmaceutical composition of the invention. The invention further is directed to methods of inhibiting cancer cell growth, including processes of cellular proliferation, invasiveness, and metastasis in biological systems. Methods include use of such a co-crystal or pharmaceutical composition to inhibit cancer cell growth.

The invention provides a method of inhibiting DNA-PK activity in a biological sample that includes contacting the biological sample with a co-crystal or pharmaceutical composition of the invention.

Also within the scope of this invention is a method of treating diseases described herein, such as cancer, which comprising administering to a subject in need thereof a therapeutically effective amount of a co-crystal of this invention or a composition of this invention.

DETAILED DESCRIPTION OF THE INVENTION

In one aspect, the invention is directed to co-crystals comprising a compound of formula I

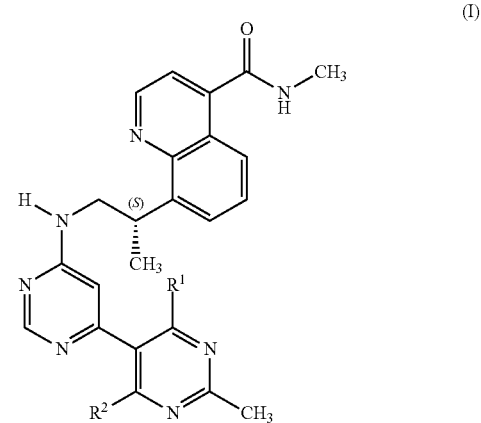

(I)

and a co-crystal former (CCF) selected from adipic acid, citric acid, fumaric acid, maleic acid, succinic acid, or benzoic acid, wherein each of $R^1$ and $R^2$ is hydrogen or deuterium.

In one embodiment, the compound of formula I is (S)—N-methyl-8-(1-((2'-methyl-[4,5'-bipyrimidin]-6-yl)amino)propan-2-yl)quinoline-4-carboxamide (Compound 1).

In another embodiment, the compound of formula I is (S)—N-methyl-8-(1-((2'-methyl-4',6'-dideutero-[4,5'-bipyrimidin]-6-yl)amino)propan-2-yl)quinoline-4-carboxamide (Compound 2).

Figure 2:
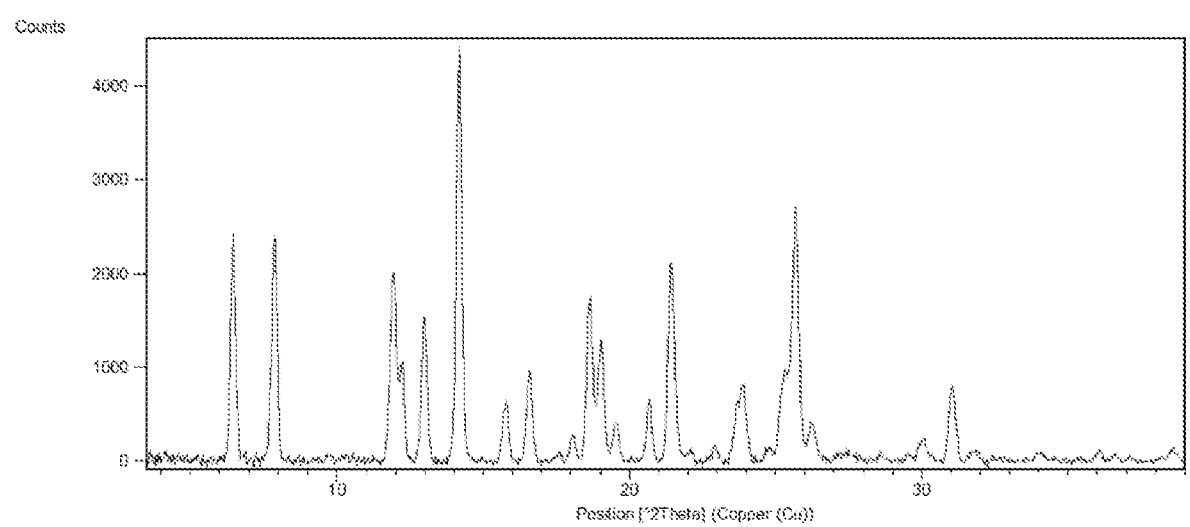
FIG. 2 shows an X-ray powder diffraction pattern of the co-crystal formed between Compound 2 with adipic acid.

In one embodiment, the invention provides a co-crystal that includes a compound of formula I and adipic acid as the CCF. In a further embodiment, the X-ray powder diffraction (XRPD) pattern of this co-crystal exhibits peaks at about 6.46, 7.91, 11.92, 12.26, 12.99, 14.19, 18.68, and 19.07-Theta. In another embodiment, the XRPD pattern of this co-crystal exhibits peaks as shown in FIG. 1. In yet another embodiment, the XRPD pattern of this co-crystal exhibits peaks as shown in FIG. 2. In yet another further embodiment, its differential scanning calorimetry (DSC) thermogram shows melting points at about 195° C. and about 245° C.

Figure 3:
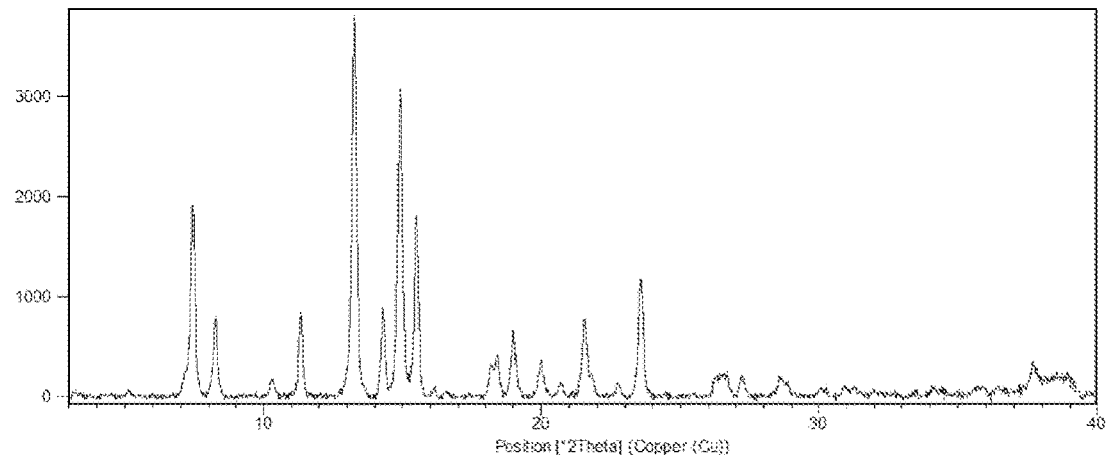
FIG. 3 shows an X-ray powder diffraction pattern of the co-crystal formed between Compound 1 with citric acid.

In one embodiment, the invention provides a co-crystal that includes a compound of formula I and citric acid as the CCF. In one embodiment, the XRPD pattern of this co-crystal exhibits peaks at about 7.44, 8.29, 11.35, 13.26, 15.49, 21.55, and 23.57-Theta. In another embodiment, the XRPD pattern of this co-crystal exhibits peaks as shown in FIG. 3. In yet another embodiment, a compound of formula I and the CCF are both in the solid state (e.g., crystalline) and are bonded non-covalently (i.e., by hydrogen bonding).

Figure 4:
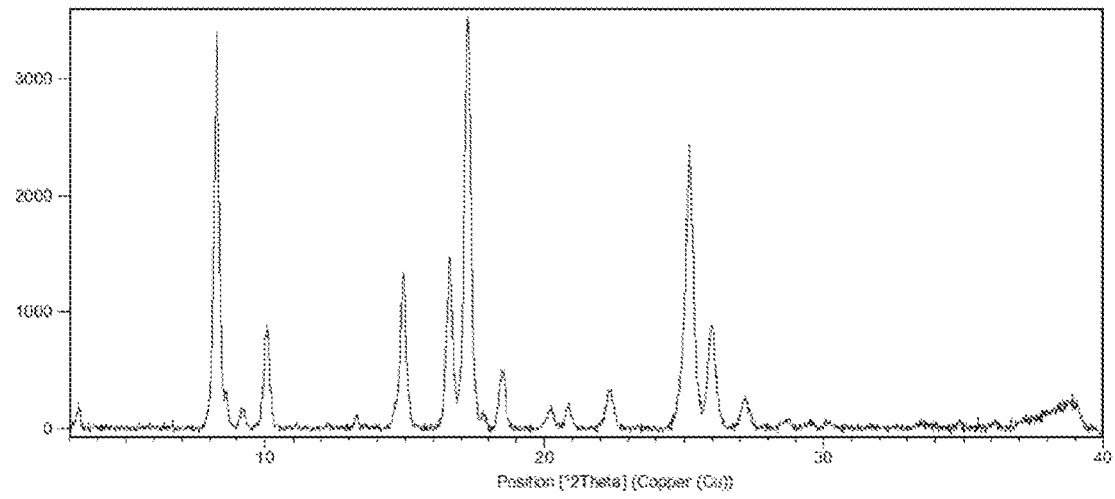
FIG. 4 shows an X-ray powder diffraction pattern of the co-crystal formed between Compound 1 and fumaric acid.

In one embodiment, the invention provides a co-crystal that includes a compound of formula I and fumaric acid as the CCF. In one embodiment, the XRPD pattern of this co-crystal exhibits peaks at about 8.26, 10.11, 14.97, 16.61, 17.22, 25.20, and 26.01-Theta. In another embodiment, the XRPD pattern of this co-crystal exhibits peaks as shown in FIG. 4. In yet another embodiment, a compound of formula I and the CCF are both in the solid state (e.g., crystalline) and are bonded non-covalently (i.e., by hydrogen bonding).

Figure 5:
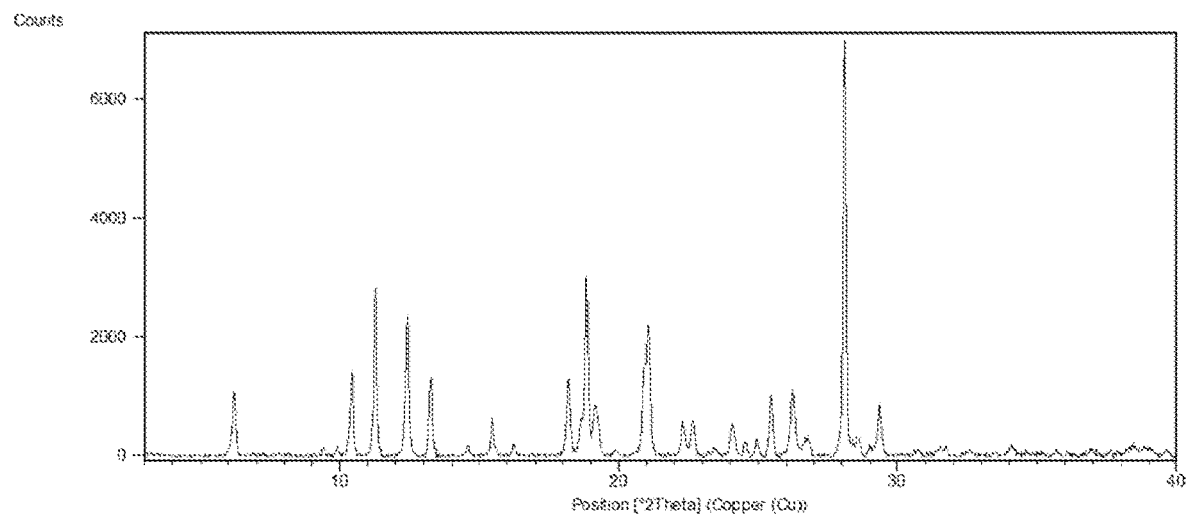
FIG. 5 shows an X-ray powder diffraction pattern of the co-crystal formed between Compound 1 and maleic acid.

In one embodiment, the invention provides a co-crystal that includes a compound of formula I and maleic acid as the CCF. In one embodiment, the XRPD pattern of this co-crystal exhibits peaks at about 6.21, 10.43, 11.28, 12.41, 13.26, 18.87, and 21.08-Theta. In another embodiment, the XRPD pattern of this co-crystal exhibits peaks as shown in FIG. 5. In yet another embodiment, a compound of formula I and the CCF are both in the solid state (e.g., crystalline) and are bonded non-covalently (i.e., by hydrogen bonding).

Figure 6:
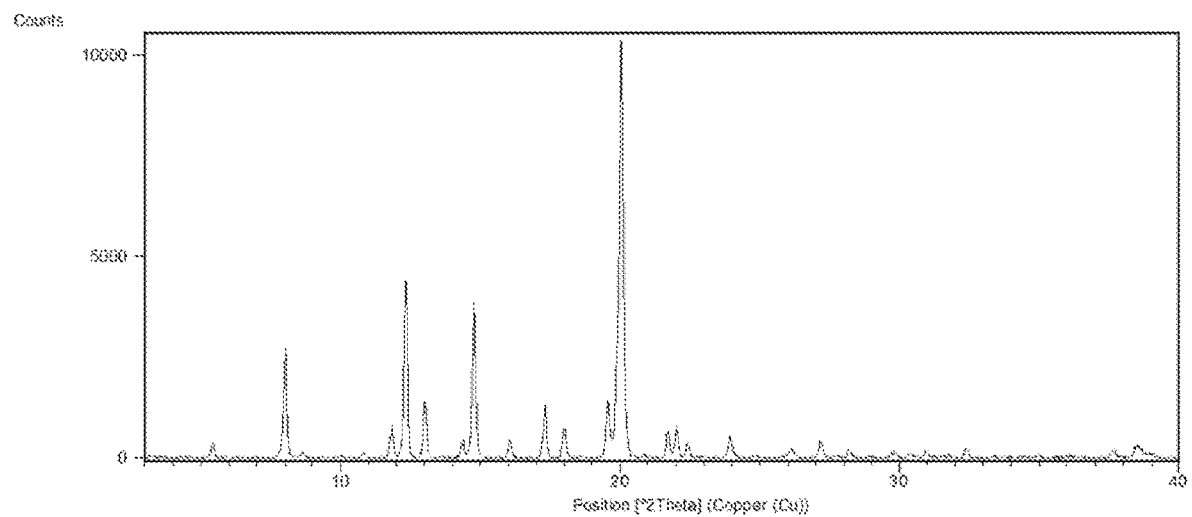
FIG. 6 shows an X-ray powder diffraction pattern of the co-crystal formed between Compound 1 and succinic acid.

In one embodiment, the invention provides a co-crystal that includes a compound of formula I and succinic acid as the CCF. In one embodiment, the XRPD pattern of this co-crystal exhibits peaks at about 8.02, 12.34, 14.78, 17.32, 19.56, and 20.06-Theta. In another embodiment, the XRPD pattern of this co-crystal exhibits peaks as shown in FIG. 6. In another embodiment, a compound of formula I and the CCF are both in the solid state (e.g., crystalline) and are bonded non-covalently (i.e., by hydrogen bonding).

Figure 7:
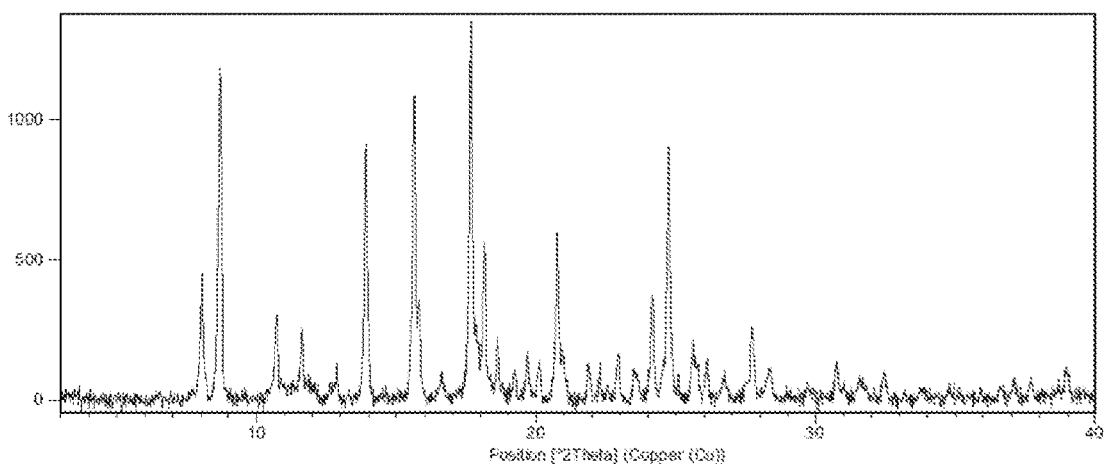
FIG. 7 shows an X-ray powder diffraction pattern of the co-crystal formed between Compound 1 and benzoic acid.

In yet another embodiment, the invention provides a co-crystal that includes a compound of formula I and benzoic acid as the CCF. In one embodiment, the XRPD pattern of this co-crystal exhibits peaks at 8.70, 13.90, 15.62, 17.65, 18.15, 20.77, and 24.72-Theta. In another embodiment, the XRPD pattern of this co-crystal exhibits peaks as shown in FIG. 7. In another embodiment, a compound of formula I and the CCF are both in the solid state (e.g., crystalline) and are bonded non-covalently).

In one embodiment, the invention provides co-crystals of the formula (Compound 1)$_n$:(AA)$_m$, wherein n is 1 and m is between 0.4 and 2.1. In one embodiment, n is 1 and m is between 0.9 and 3.1. In one embodiment for co-crystals comprising adipic acid, n is about 2 and m is about 1. In one embodiment for co-crystals comprising adipic acid, n is about 2 and m is about 1.

In another embodiment, the invention provides co-crystals of the formula (Compound 2)$_n$:(AA)$_m$, wherein n is 1 and m is between 0.4 and 2.1 In one embodiment for co-crystals comprising adipic acid, n is about 2 and m is about 1.

In another embodiment, the invention provides a co-crystal of a compound of formula I and CCF adipic acid, citric acid, fumaric acid, maleic acid, succinic acid, or benzoic acid, wherein the co-crystal is a solid at the room temperature and the compound of formula I and CCF interact by noncovalent bonds. In certain embodiments, the non-covalent bond interactions between the compound of formula I and CCF include hydrogen bonding and van der Waals interactions. In one embodiment, the CCF is adipic acid.

In one embodiment, the invention provides a co-crystal of Compound (1) and CCF adipic acid, wherein the molar ratio of Compound (1) to adipic acid is about 2:1.

In another embodiment, the invention provides a co-crystal of Compound (2) and CCF adipic acid, wherein the molar ratio of Compound (2) to adipic acid is about 2:1.

In another embodiment, the co-crystal of Compound (2) and CCF adipic acid (adipic acid co-crystal of Compound (2)) is in polymorphic Form A or B. Polymorphic Forms A and B are two conformational polymorphs of the adipic acid co-crystal of Compound (2). In yet another embodiment, the co-crystal of Compound (1) and CCF adipic acid (adipic acid co-crystal of Compound (1)) is in polymorphic Form A or B. Polymorphic Forms A and B are two conformational polymorphs of the adipic acid co-crystal of Compound (1), and their $^{13}$C solid state nuclear magnetic resonance spectroscopies are essentially the same as those for Polymorphic Forms A and B of Compound (2).

Figure 16:
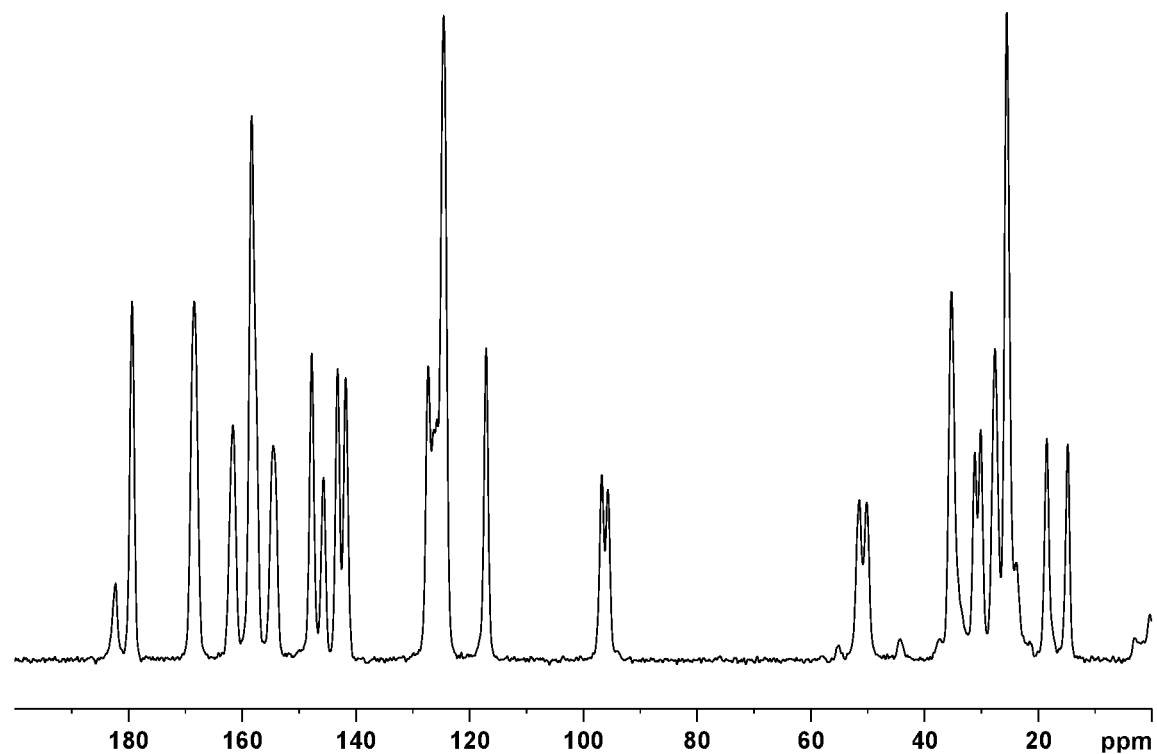
FIG. 16 shows a solid-state NMR spectrum of polymorphic Form A of the co-crystal formed between Compound 1 and adipic acid.
Figure 17:
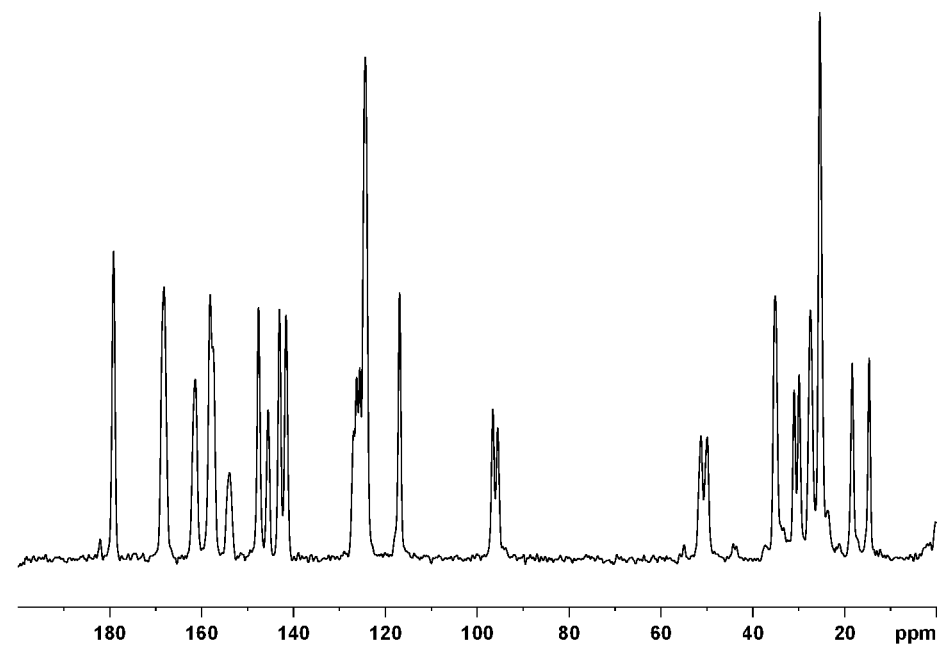
FIG. 17 shows a solid-state NMR spectrum of polymorphic Form A of the co-crystal formed between Compound 2 and adipic acid.

In a specific embodiment, the polymorphic Form A is characterized by $^{13}$C solid state nuclear magnetic resonance spectroscopy peaks at about 117.1, 96.8, 95.7, 27.6, 14.8 ppm. In another specific embodiment, the polymorphic Form A is characterized by $^{13}$C solid state nuclear magnetic resonance spectroscopy peaks at about 161.6, 154.5, 117.1, 96.8, 95.7, 51.5, 50.2, 27.6, 25.6, 18.5, and 14.8 ppm. In yet another specific embodiment, the polymorphic Form A is characterized by $^{13}$C solid state nuclear magnetic resonance spectroscopy peaks at about 179.4, 168.4, 161.6, 158.3, 154.5, 147.8, 145.7, 143.2, 141.8, 124.6, 117.1, 96.8, 95.7, 51.5, 50.2, 31.2, 30.1, 27.6, 25.6, 18.5, and 14.8 ppm. In yet another specific embodiment, the polymorphic Form A is characterized by $^{13}$C solid state nuclear magnetic resonance spectroscopy peaks as shown in FIG. 16 or 17.

In a specific embodiment, the polymorphic Form B is characterized by $^{13}$C solid state nuclear magnetic resonance spectroscopy peaks at about 117.9, 97.3, 94.0, 26.7, and 15.7 ppm. In another specific embodiment, the polymorphic Form B is characterized by $^{13}$C solid state nuclear magnetic resonance spectroscopy peaks at about 161.7, 153.8, 117.9, 97.3, 94.0, 50.7, 25.3, 26.7, 18.8, and 15.7 ppm. In yet another specific embodiment, the polymorphic Form B is characterized by $^{13}$C solid state nuclear magnetic resonance spectroscopy peaks at about 179.1, 168.3, 158.1, 147.2, 142.4, 125.8, 124.5, 117.9, 97.3, 94.0, 32.3, 30.1, 26.7, and 15.7 ppm. In yet another specific embodiment, the polymorphic Form B is characterized by $^{13}$C solid state nuclear magnetic resonance spectroscopy peaks as shown in FIG. 17.

In yet another embodiment, the co-crystal of Compound (2) and CCF adipic acid (adipic acid co-crystal of Compound (2)) is in a mixture of polymorphic Forms A and B. In yet another embodiment, the co-crystal of Compound (1) and CCF adipic acid (adipic acid co-crystal of Compound (1)) is in a mixture of polymorphic Forms A and B.

The present invention encompasses the co-crystals of a compound of formula I and CCF described above in isolated, pure form, or in a mixture as a solid composition when admixed with other materials, for example, free form of compound of formula I or free CCF. In one embodiment, the invention provides pharmaceutically acceptable compositions comprising the co-crystals of a compound of formula I and the CCF described above and an additional free CCF. In a specific embodiment, the compositions comprise the co-crystals of Compound (1) or (2) and CCF adipic acid described above and additional adipic acid. In some specific embodiments, the overall molar ratio of the compound of formula I to CCF (both part of the co-crystals and free CCF, e.g., adpic acid in the co-crystals and free adipic acid) in such compositions is in a range from about 1:0.55 to about 1:100. In other specific embodiments, the overall molar ratio of the compound of formula I to CCF in such compositions is in a range from about 1:0.55 to about 1:50. In other specific embodiments, the overall molar ratio of the compound of formula I to CCF in such compositions is in a range from about 1:0.55 to about 1:10. In some specific embodiments, the overall weight ratio of the compound of formula I to CCF in such compositions is in a range from about 85 wt %:15 wt % to about 60 wt %:40 wt %. In other specific embodiments, the overall weight ratio of the compound of formula I to CCF is in a range from about 70 wt %:30 wt % to about 60 wt %:40 wt %. In yet other embodiments, the overall weight ratio of the compound of formula I to CCF is about 65 wt %:35 wt %.

In another embodiment, the invention provides eutectic solid compositions comprising: (a) a co-crystal comprising a compound of formula (I), and a CCF selected from adipic acid, wherein each of $R^1$ and $R^2$ is hydrogen or deuterium, and wherein the molar ratio of the compound of formula I to adipic acid is about 2 to 1; and (b) adipic acid. As used herein, the term "eutectic solid" means a solid material resulting from a eutectic reaction known in the art. Without being bound to a particular theory, an eutectic reaction is defined as follows:

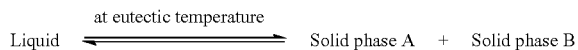

In the eutection reaction, a single liquid phase and two solid phases all co-exist at the same time and are in chemical equilibrium. It forms a super-lattice or microstructure on cooling which releases at once all its components into a liquid mixture (melts) at a specific temperature (the eutectic temperature).

In one embodiment, the overall weight ratio of the compound of formula I to adipic acid in the eutectic solid compositions is in a range from about 70 wt %:30 wt % to about 60 wt %:40 wt %. In yet another embodiment, the overall weight ratio of the compound of formula I to adipic acid is in a range from about 65 wt %:35 wt %. In yet another embodiment, the molar ratio of the co-crystal of a compound of formula I to adipic acid is about 1 to 1.03.

The pure form means that the particular co-crystal or polymorphic form comprises over 95% (w/w), for example, over 98% (w/w), over 99% (w/w %), over 99.5% (w/w), or over 99.9% (w/w).

More specifically, the present invention also provides pharmaceutically acceptable compositions where each of the co-crystals or polymorphic forms are in the form of a composition or a mixture of the polymorphic form with one or more other crystalline, solvate, amorphous, or other polymorphic forms or their combinations thereof. For example, in one embodiment, the compositions comprise Form A of the adipic acid co-crystal of Compound (2) along with one or more other polymorphic forms of Compound (2), such as amorphous form, hydrates, solvates, and/or other forms or their combinations thereof. In a specific embodiment, the compositions comprise Form A of the adipic acid co-crystal of Compound (2) along with Form B of the adipic acid co-crystal of Compound (2). More specifically, the composition may comprise from trace amounts up to 100% of the specific polymorphic form or any amount, for example, in a range of 0.1%-0.5%, 0.1%-1%, 0.1%-2%, 0.1%-5%, 0.1%-10%, 0.1%-20%, 0.1%-30%, 0.1%-40%, 0.1%-50%, 1%-50%, or 10%-50% by weight based on the total amount of the compound of formula I in the composition. Alternatively, the composition may comprise at least 50%, 60%, 70%, 80%, 90%, 95%, 97%, 98%, 99%, 99.5% or 99.9% by weight of specific polymorphic form based on the total amount of the compound of formula I in the composition.

In one embodiment, the compounds in accordance with the present invention are provided in the form of a single enantiomer at least 95%, at least 97% and at least 99% free of the corresponding enantiomer.

In a further embodiment, the compounds in accordance with the present invention are in the form of the (+) enantiomer at least 95% free of the corresponding (−) enantiomer.

In a further embodiment, the compounds in accordance with the present invention are in the form of the (+) enantiomer at least 97% free of the corresponding (−) enantiomer.

In a further embodiment, the compounds in accordance with the present invention are in the form of the (+) enantiomer at least 99% free of the corresponding (−) enantiomer.

In a further embodiment, the compounds in accordance with the present invention are in the form of the (−) enantiomer at least 95% free of the corresponding (+) enantiomer.

In a further embodiment, the compounds in accordance with the present invention are in the form of the (−) enantiomer at least 97% free of the corresponding (+) enantiomer.

In a further embodiment the compounds in accordance with the present invention are in the form of the (−) enantiomer at least 99% free of the corresponding (+) enantiomer.

The present invention also provides methods of making the co-crystals described above. In one embodiment, the methods comprises grinding, heating, co-subliming, co-melting, or contacting either (S)—N-methyl-8-(1-((2'-methyl-[4,5'-bipyrimidin]-6-yl)amino)propan-2-yl)quinoline-4-carboxamide or (S)—N-methyl-8-(1-((2'-methyl-4', 6'-dideutero-[4,5'-bipyrimidin]-6-yl)amino)propan-2-yl)quinoline-4-carboxamide with the co-crystal former under crystallization conditions so as to form the co-crystal in solid phase, wherein the co-crystal former is selected from adipic acid, citric acid, fumaric acid, maleic acid, succinic acid, or benzoic acid.

In another embodiment, the methods comprises mixing a compound of formula (I) with a CCF selected from adipic acid, citric acid, fumaric acid, maleic acid, succinic acid, or benzoic acid at an elevated temperature to form the co-crystal. The compound of formula (I) can be mixed with the CCF to generate a mixture of the compound and CCF, and then the mixture of the compound and CCF are heated at an elevated temperature to form the co-crystal. Alternatively, the mixing and heating steps can be performed at the same time.

In one specific embodiment, the CCF is adipic acid, and the compound of formula (I) is mixed with adipic acid at an elevated temperature in a range of about 110° C. and about 195° C. to form the co-crystal. In another specific embodiment, the elevated temperature is in a range of about 130° C. and about 180° C., or in a range of about 140° C. and about 160° C.

In another specific embodiment, the CCF is adipic acid, and 10 wt % to about 85 wt % of the compound (I) and about 90 wt % to 15 wt % of adipic acid are mixed. In yet another specific embodiment, about 30 wt % to about 80 wt % and the adipic acid is about 70 wt % to about 20 wt %. In yet another specific embodiment, the compound (I) is about 50 wt % to about 80 wt % and the adipic acid is about 50 wt % to about 20 wt %. In yet another specific embodiment, the compound (I) is about 60 wt % to 70 wt % and the adipic acid is about 40 wt % to about 30 wt %. In yet another specific embodiment, the compound (I) is about 65 wt % and the adipic acid is about 35 wt %.

In yet another embodiment, the methods include: providing the compound of formula I; providing the co-crystal former; grinding, heating, co-subliming, co-melting, or contacting in solution the compound of formula I with the co-crystal former under crystallization conditions so as to form the co-crystal in solid phase; and then optionally isolating the co-crystal formed thereby. In some specific embodiments, the making a co-crystal of a compound of formula I and the CCF includes providing the compound of formula I and adipic acid, citric acid, fumaric acid, maleic acid, succinic acid, or benzoic acid in a molar ratio between about 1 to 0.55 to about 1 to 3.6, respectively. In some specific embodiments, the making a co-crystal of a compound of formula I and the CCF includes providing the compound of formula I and adipic acid, citric acid, fumaric acid, maleic acid, succinic acid, or benzoic acid in a molar ratio between about 1 to 1.2 to about 1 to 3.6, respectively.

In yet another embodiment, the invention provides methods for modulating a chemical or physical property of interest (such as melting point, solubility, dissolution, hygroscopicity, and bioavailability) of a co-crystal containing a compound of formula I and adipic acid, citric acid, fumaric acid, maleic acid, succinic acid, or benzoic acid. The methods include: measuring the chemical or physical property of interest for the compound of formula I and CCF; determining the mole fraction of the compound of formula I and CCF that will result in the desired modulation of the chemical or physical property of interest; and preparing the co-crystal with the molar fraction as determined.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference/

For XRPD peak assignments, the term "about" means a range of +/−0.2 relative to the stated value. For $^{13}$C solid state NMR spectra, the term "about" means a range of +/−0.1 relative to the stated value. Otherwise, the term "about" means a value of +/−10% of the stated value. When this term is followed by a series of numbers it applies to each of the numbers in the series.

For compounds of the invention in which $R^1$ or $R^2$ is deuterium, the deuterium to hydrogen ratio is at least 5 to 1. In some embodiments, the deuterium to hydrogen ratio is at least 9 to 1. In other embodiments, the deuterium to hydrogen ratio is at least 19 to 1.

Methods for preparing and characterizing a co-crystal are well documented in the literature. See, e.g., Trask et al., *Chem. Commun.*, 2004, 890-891; and 0. Almarsson and M. J. Zaworotko, *Chem. Commun.*, 2004, 1889-1896. These methods in general are also suitable for preparing and characterizing co-crystals of this invention.

Examples of preparing co-crystals with an active pharmaceutical ingredient and a CCF include hot-melt extrusion, ball-milling, melting in a reaction block, evaporating solvent, slurry conversion, blending, sublimation, or modeling. In the ball-milling method, certain molar ratios of the components of the co-crystal (e.g., a compound of interest, such as a compound of formula I of this invention, and a CCF) are mixed and milled with balls. Optionally, a solvent such as methyl ethyl ketone, chloroform, and/or water can be added to the mixture being ball milled. After milling, the mixture can be dried under vacuum either at the room temperature or in the heated condition, which typically gives a powder product. In the melting method, the components of a co-crystal (e.g., a CCF and a compound of formula I) are mixed, optionally with a solvent such as acetonitrile. The mixture is then placed in a reaction block with the lid closed, and then heated to the endotherm. The resulting mixture is then cooled off and solvent, if used, removed. In the solvent-evaporation method, each component of a co-crystal is first dissolved in a solvent (e.g., a solvent mixture, such as methanol/dichloromethane azeotrope, or toluene/acetonitrile (e.g., 50/50 by volume)), and the solutions are then mixed together. The mixture is then allowed to sit and solvent to evaporate to dryness, to yield the co-crystal. In the hot-melt extrusion (HME) method, a new material (the extrudate) is formed by forcing it through an orifice or die (extruder) under controlled conditions, such as temperature, mixing, feed-rate and pressure. An extruder typically comprises a platform that supports a drive system, an extrusion barrel, a rotating screw arranged on a screw shaft and an extrusion die for defining product shape. Alternatively, the extrusion die can be removed and the product can be shaped by other means. Typically, process parameters are controlled via connection to a central electronic control unit. The extrusion drive system generally comprises motor, gearbox, linkage and thrust bearings, whereas the barrel and screw is commonly utilized in a modular configuration. Any suitable HME technologies known in the art, for example, Gavin P. Andrews et al., "Hot-melt extrusion: an emerging drug delivery technology", *Pharmaceutical Technology Europe*, volume 21, Issue 1 (2009), can be used in the invention. In one embodiment, the co-crystals of the invention are prepared by hot-melt extrusion.

Examples of characterization methods include thermogravimetric analysis (TGA), differential scanning calorimetry (DSC), X-ray powder diffraction (XRPD), solid-state nuclear magnetic resonance spectroscopy (ss-NMR), solubility analyses, dynamic vapor sorption, infrared off-gas analysis, and suspension stability. TGA can be used to investigate the presence of residual solvents in a co-crystal sample and to identify the temperature at which decomposition of each co-crystal sample occurs. DSC can be used to look for thermotransitions occurring in a co-crystal sample as a function of temperature and determine the melting point of each co-crystal sample. XRPD can be used for structural characterization of the co-crystal. Solubility analysis can be performed to reflect the changes in the physical state of each co-crystal sample. Suspension stability analysis can be used to determine the chemical stability of a co-crystal sample in a solvent.

Pharmaceutically Acceptable Salts

The present invention also covers co-crystals formed with pharmaceutically acceptable salts of the compounds of formula I. Also, the combination therapy of the invention discussed below includes administering the compounds of formula I and pharmaceutically acceptable salts thereof, and their co-crystals described herein. The compounds of formula I can exist in free form for treatment, or where appropriate, as a pharmaceutically acceptable salt.

A "pharmaceutically acceptable salt" means any non-toxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also a DNA-PK inhibitor.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference.

Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Uses of the Co-Crystals and Pharmaceutical Compositions of the Invention

An effective amount of a co-crystal or pharmaceutical composition of the invention can be used to treat diseases implicated or associated with the cancer. An effective amount is the amount which is required to confer a therapeutic effect on the treated subject, e.g. a patient. As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In one embodiment, the subject is a non-human animal such as a farm animal (e.g., a horse, cow, pig or sheep), or a pet (e.g., a dog, cat, guinea pig or rabbit). In a preferred embodiment, the subject is a "human".

The precise amount of compound administered to a subject will depend on the mode of administration, the type and severity of the cancer and on the characteristics of the subject, such as general health, age, sex, body weight and tolerance to drugs. The skilled artisan will be able to determine appropriate dosages depending on these and other factors. When co-administered with other agents, e.g., when co-administered with an anti-cancer medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compounds described herein required to treat, to prevent, inhibit (fully or partially) or arrest the progress of the disease.

The effective amount of a co-crystal or pharmaceutical composition of the invention is between about 0.1 to about 200 mg/kg body weight/day. In one embodiment, the effective amount of a co-crystal or pharmaceutical composition of the invention is between about 1 to about 50 mg/kg body weight/day. In another embodiment, the effective amount of a co-crystal or pharmaceutical composition of the invention is between about 2 to about 20 mg/kg body weight/day. Effective doses will also vary, as recognized by those skilled in the art, dependent on route of administration, excipient usage, and the possibility of co-usage with other therapeutic treatments including use of other therapeutic agents and/or therapy.

The co-crystals or pharmaceutical compositions of the invention can be administered to the subject in need thereof (e.g., cells, a tissue, or a patient (including an animal or a human) by any method that permits the delivery of a compound of formula I, e.g., orally, intravenously, or parenterally. For instance, they can be administered via pills, tablets, capsules, aerosols, suppositories, liquid formulations for ingestion or injection.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof.

Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In one specific example, the pharmaceutically acceptable compositions of the invention comprise methylcellulose, such as about 0.5 wt % methylcellulose. In another specific example, the pharmaceutically acceptable compositions of the invention comprise methylcellulose and benzoic acid, such as about 0.5 wt % methylcellulose and about 0.2 wt % benzoic acid. In another specific example, the pharmaceutically acceptable compositions comprise methylcellulose and benzoic acid, such as about 0.5 wt % methylcellulose, about 0.1 wt % benzoic acid about 0.1 wt % sodium benzoate. In some embodiments, the pharmaceutical compositions further comprise free adipic acid (free CCF that is not a CCF of the co-crystals of the invention). Such adipic acid is in a concentration of, for example, about 5 mg/[g vehicle] to about 10 mg/[g vehicle], such as about 8.8 mg/[g vehicle].

Any orally acceptable dosage form including, but not limited to, capsules, tablets, aqueous suspensions or solutions, can be used for the oral administration. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Microencapsulated forms with one or more excipients as noted above can also be used in the invention. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Sterile injectable forms may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

In order to prolong the effect of the active compounds administered, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the active compound in biodegradable polymers such as polylactide-polyglycolide. Depending upon the ratio of the active compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

When desired the above described formulations adapted to give sustained release of the active ingredient may be employed.

Compositions for rectal or vaginal administration are specifically suppositories which can be prepared by mixing the active compound with suitable non-irritating excipients or carriers such as cocoa butter, polyethylene glycol or a suppository wax which are solid at ambient temperature but liquid at body temperature and therefore melt in the rectum or vaginal cavity and release the active compound.

Dosage forms for topical or transdermal administration include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear-drops, and eye drops are also contemplated as being within the scope of this invention. Additionally, transdermal patches, which have the added advantage of providing controlled delivery of a compound to the body, can also be used. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Alternatively, the active compounds and pharmaceutically acceptable compositions thereof may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The co-crystals or pharmaceutical compositions of the invention also can be delivered by implantation (e.g., surgically) such with an implantable device. Examples of implantable devices include, but are not limited to, stents, delivery pumps, vascular filters, and implantable control release compositions. Any implantable device can be used to deliver a compound of formula I as the active ingredient in the co-crystals or pharmaceutical compositions of this invention, provided that 1) the device, compound of formula I, and any pharmaceutical composition including the compound are biocompatible, and 2) that the device can deliver or release an effective amount of the compound to confer a therapeutic effect on the treated patient.

Delivery of therapeutic agents via stents, delivery pumps (e g., mini-osmotic pumps), and other implantable devices is known in the art. See, e.g., "Recent Developments in Coated Stents" by Hofma et al., published in *Current Interventional Cardiology Reports,* 2001, 3: 28-36, the entire contents of which, including references cited therein, are incorporated herein. Other descriptions of implantable devices, such as stents, can be found in U.S. Pat. Nos. 6,569,195 and 6,322,847, and PCT International Publication Numbers WO 04/0044405, WO 04/0018228, WO 03/0229390, WO 03/0228346, WO 03/0225450, WO 03/0216699, and WO 03/0204168, each of which (as well as other publications cited herein) is incorporated herein in its entirety.

The active compounds and pharmaceutically acceptable compositions thereof can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose. The amount of the active compound in a unit dosage form will vary depending upon, for example, the host treated, and the particular mode of administration, for example, from about 0.1 to about 200 mg/kg body weight/day.

In one embodiment, the invention is directed to methods for potentiating a therapeutic regimen for treatment of cancer. The methods comprise the step of administering to an individual in need thereof an effective amount of a co-crystal of the invention or pharmaceutical composition thereof. The compounds of formula I and co-crystals thereof, without being bound to a particular theory, can inhibit DNA-PK. DNA-PK plays an important role in cellular survival, for example, of cancer cells, after DNA damage via its activity repairing double strand breaks (DSBs) by non-homologous end joining (NHEJ). Targeting DNA-PK therefore can improve cancer patient outcomes especially in cancer patients who receive therapies to induce DSBs in tumor cells since the DSBs in the tumor cells cannot be repaired and rapidly lead to cell death. In some embodiments, the methods of the invention potentiate therapeutic regimen to induce DSBs. Examples of such therapies include radiation therapy (RT) and certain chemotherapies such as topoisomerase I inhibitors (e.g., topotecan, irinotecan/SN38, rubitecan and other derivatives), topoisomerase II inhibitors (e.g., etoposide and doxil), DNA intercalators (e.g., doxorubicin or epirubicin), radiomimetics (e.g., bleomycin), PARP inhibitors (e.g., BMN-673), DNA-repair inhibitors (e.g., carboplatin), DNA cross-linkers (e.g., cisplatin), inhibitors of thymidylate synthase (e.g., fluorouracil (5-FU)), mitotic inhibitors (e.g., paclitaxel), EGFR inhibitors (e.g., erlotinib), and EGFR monoclonal antibodies (e.g., cetuximab).

In one specific embodiment, said potentiated therapeutic regimen for treatment cancer includes at least one chemotherapy selected from a topoisomerase I inhibitor, topoisomerase II inhibitor, DNA intercalator, radiomimetic, PARP inhibitor, DNA-repair inhibitor, DNA cross-linkers, inhibitor of thymidylate synthase, mitotic inhibitor, EGFR inhibitor, EGFR monoclonal antibody, or radiation. In another specific embodiment, the therapeutic regimen for treatment of cancer includes radiation therapy. The co-crystals or pharmaceutical compositions of the invention are useful in instances where radiation therapy is indicated to enhance the therapeutic benefit of such treatment. In addition, radiation therapy frequently is indicated as an adjuvant to surgery in the treatment of cancer. In general a goal of radiation therapy in the adjuvant setting is to reduce the risk of recurrence and enhance disease-free survival when the primary tumor has been controlled. For example, adjuvant radiation therapy is indicated in cancers, including but not limited to, breast cancer, colorectal cancer, gastric-esophageal cancer, fibrosarcoma, glioblastoma, hepatocellular carcinoma, head and neck squamous cell carcinoma, melanoma, lung cancer, pancreatic cancer, and prostate cancer as described below. In yet another specific embodiment, the therapeutic regimen for treatment of cancer includes both radiation therapy and a chemotherapy of at least one chemotherapy agents selected from topoisomerase I inhibitors, topoisomerase II inhibitors, DNA intercalators, radiomimetics, PARP inhibitors, DNA-repair inhibitors, DNA cross-linkerss, inhibitors of thymidylate synthase, mitotic inhibitors, EGFR inhibitors, or EGFR monoclonal antibodies.

In another embodiment, the invention provides methods of inhibiting or preventing repair of DNA-damage by homologous recombination in cancerous cells. Another embodiment provides methods of promoting cell death in cancerous cells. Yet another embodiment provides methods or preventing cell repair of DNA-damage in cancerous cells.

The invention further relates to sensitizing (e.g., radio-sensitizing) tumor cells by utilizing a co-crystal or pharmaceutical composition of the invention. Accordingly, such a co-crystal or pharmaceutical composition can "radiosensitize" a cell when administered to animals in therapeutically effective amount to increase the sensitivity of cells to electromagnetic radiation and/or to promote the treatment of diseases that are treatable with electromagnetic radiation (e.g., X-rays). Diseases that are treatable with electromagnetic radiation include neoplastic diseases, benign and malignant tumors, and cancerous cells. In some embodiments, the invention further relates to sensitizing tumor cells to DNA-damaging agents.

The present invention also provides methods of treating cancer in an animal that includes administering to the animal an effective amount of a compound of formula (I) or a co-crystal thereof, or a pharmaceutical composition of the invention. The invention further is directed to methods of inhibiting cancer cell growth, including processes of cellular proliferation, invasiveness, and metastasis in biological systems. Methods include use of such a co-crystal or pharmaceutical composition to inhibit cancer cell growth. Preferably, the methods are employed to inhibit or reduce cancer cell growth, invasiveness, metastasis, or tumor incidence in living animals, such as mammals. Methods of the invention also are readily adaptable for use in assay systems, e.g., assaying cancer cell growth and properties thereof, as well as identifying compounds that affect cancer cell growth.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The invention also enables treatment of cancers of the myeloid or lymphoid systems, including leukemias, lymphomas, and other cancers that typically do not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, non-small cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Thus, also within the scope of this invention is a method of treating such diseases, which comprising administering to a subject in need thereof a therapeutically effective amount of a co-crystal of this invention or a pharmaceutical composition of this invention.

In some embodiments, the invention is employed for treating lung cancer (e.g., non-small cell lung cancer (NSCLC), small cell lung cancer (SCLC), or extensive-disease small cell lung cancer (ED-SCLC)), breast cancer (e.g., triple negative breast cancer), prostate cancer, heme malignancies (e.g., acute myeloid leukemia (AML)), myeloma (e.g., plasma cell myeloma (PCM)), gastro-esophageal junction cancer (GEJ), ovarian cancer, colon cancer, pharynx cancer, pancreatic cancer, gastric cancer, esophageal cancer, lymphoma (e.g., diffuse large B-cell lymphoma (DLBL)), or lung fibroblast. In some specific embodiments, the invention is employed for treating lung cancer (e.g., non-small cell lung cancer (NSCLC), small cell lung cancer (SCLC), or extensive-disease small cell lung cancer (ED-SCLC)), breast cancer (e.g., triple negative breast cancer), prostate cancer, acute myeloid leukemia, myeloma, gastro-esophageal junction cancer (GEJ), or ovarian cancer. In some specific embodiments, the invention is employed for treating lung cancer such as non-small cell lung cancer (NSCLC) or small cell lung cancer, such as extensive-disease small cell lung cancer (ED-SCLC). In some specific embodiments, the invention is employed for treating breast cancer, such as triple negative breast cancer. In some specific embodiments, the invention is employed for treating gastro-esophageal junction cancer (GEJ). In some specific embodiments, the invention is employed for treating acute myeloid leukemia (AML).

The invention also provides a method of inhibiting DNA-PK activity in a biological sample that includes contacting the biological sample with a co-crystal or pharmaceutical composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly DNA-PK activity, in a biological sample is useful for a variety of purposes known to one of skill in the art. An example includes, but is not limited to, the inhibition of DNA-PK in a biological assay. In one embodiment, the method of inhibiting DNA-PK activity in a biological sample is limited to non-therapeutic methods.

The term "biological sample", as used herein, includes, without limitation, cell cultures or extracts thereof; biopsied material obtained from a mammal or extracts thereof; blood, saliva, urine, feces, semen, tears, or other body fluids or extracts thereof.

Combination Therapies

The present invention also provides combination of chemotherapy with a compound or composition of the invention, or with a combination of another anticancer therapy, such as anticancer agent or radiation therapy (or radiotherapy). In some embodiments, the compounds of formula I and co-crystals thereof are used in combination with another anticancer therapy, such as anticancer drug or radiation therapy. As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

In some embodiments, said another anticancer therapy is an anti-cancer agent. In other embodiments, said another anticancer therapy is a DNA-damaging agent. In yet other embodiments, said another anticancer therapy is selected from radiation therapy. In a specific embodiment, the radiation therapy is ionizing radiation.

Examples of DNA-damaging agents that may be used in combination with the compounds of formula I and co-crystals thereof include, but are not limited to platinating agents, such as carboplatin, nedaplatin, satraplatin and other derivatives; topoisomerase I inhibitors, such as topotecan, irinotecan/SN38, rubitecan and other derivatives; antimetabolites, such as folic family (methotrexate, pemetrexed and relatives); purine antagonists and pyrimidine antagonists (thioguanine, fludarabine, cladribine, cytarabine, gemcitabine, 6-mercaptopurine, 5-fluorouracil (5FU) and relatives); alkylating agents, such as nitrogen mustards (cyclophosphamide, melphalan, chlorambucil, mechlorethamine, ifosfamide and relatives); nitrosoureas (e.g. carmustine); triazenes (dacarbazine, temozolomide); alkyl sulphonates (eg busulfan); procarbazine and aziridines; antibiotics, such as hydroxyurea, anthracyclines (doxorubicin, daunorubicin, epirubicin and other derivatives); anthracenediones (mitoxantrone and relatives); *streptomyces* family (bleomycin, mitomycin C, actinomycin); and ultraviolet light.

Other therapies or anticancer agents that may be used in combination with the inventive agents of the present invention include surgery, radiotherapy (in but a few examples, ionizaing radiation (IR), gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (vinblastine, vincristine, vinorelbine, paclitaxel), podophyllotoxins (etoposide, irinotecan, vopotecan), nitrosoureas (varmustine, lomustine), inorganic ions (cisplatin, carboplatin), enzymes (vsparaginase), and hormones (tamoxifen, leuprolide, flutamide, and megestrol), Gleevec™, adriamycin, dexamethasone, and cyclophosphamide.

Additional examples of the therapeutic agents for the co-therapy of the invention include: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (masterone Injection®); Elliott's B Solution (Elliott's B Solution®); epirubicin (Ellence®); Epoetin alfa (Epogen®); erlotinib (Tarceva®); estramustine (EmcytR®); etoposide phosphate (Etopophos®); etoposide, VP-16 (Vepesid®); exemestane (Aromasin®); Filgrastim (Neupogen®); floxuridine (Intraarterial®) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, nci.nih.gov, a list of the FDA approved oncology drugs at fda.gov/cder/cancer/druglistframe.htm, and The Merck Manual, Seventeenth Ed. 1999.

Some embodiments comprising administering to said patient an additional therapeutic agent selected from a DNA-damaging agent, wherein said additional therapeutic agent is appropriate for the disease being treated, and said additional therapeutic agent is administered together with said compound as a single dosage form or separately from said compound as part of a multiple dosage form.

In some embodiments, said DNA-damaging agent is selected from at least one from radiation, (e.g., ionizing radiation), radiomimetic neocarzinostatin, a platinating agent, a topoisomerase I inhibitor, a topoisomerase II inhibitor, an antimetabolite, an alkylating agent, an alkyl sulphonates, an antimetabolite, a PARP inhibitor, or an antibiotic. In other embodiments, said DNA-damaging agent is selected from at least one from ionizing radiation, a platinating agent, a topoisomerase I inhibitor, a topoisomerase II inhibitor, a PARP inhibitor, or an antibiotic.

Examples of platinating agents include cisplatin, oxaliplatin, carboplatin, nedaplatin, satraplatin and other derivatives. Other platinating agents include lobaplatin, and triplatin. Other platinating agents include tetranitrate, picoplatin, satraplatin, proLindac and aroplatin.

Examples of topoisomerase I inhibitors include camptothecin, topotecan, irinotecan/SN38, rubitecan and other derivatives. Other topoisomerase I inhibitors include belotecan.

Examples of topoisomerase II inhibitors include etoposide, daunorubicin, doxorubicin, mitoxantrone, aclarubicin, epirubicin, idarubicin, amrubicin, amsacrine, pirarubicin, valrubicin, zorubicin and teniposide.

Examples of antimetabolites include members of the folic family, purine family (purine antagonists), or pyrimidine family (pyrimidine antagonists). Examples of the folic family include methotrexate, pemetrexed and relatives; examples of the purine family include thioguanine, fludarabine, cladribine, 6-mercaptopurine, and relatives; examples of the pyrimidine family include cytarabine, gemcitabine, 5-fluorouracil (5FU) and relatives.

Some other specific examples of antimetabolites include aminopterin, methotrexate, pemetrexed, raltitrexed, pentostatin, cladribine, clofarabine, fludarabine, thioguanine, mercaptopurine, fluorouracil, capecitabine, tegafur, carmofur, floxuridine, cytarabine, gemcitabine, azacitidine and hydroxyurea.

Examples of alkylating agents include nitrogen mustards, triazenes, alkyl sulphonates, procarbazine and aziridines. Examples of nitrogen mustards include cyclophosphamide, melphalan, chlorambucil and relatives; examples of nitrosoureas include carmustine; examples of triazenes include dacarbazine and temozolomide; examples of alkyl sulphonates include busulfan.

Other specific examples of alkylating agents include mechlorethamine, cyclophosphamide, ifosfamide, trofosfamide, chlorambucil, melphalan, prednimustine, bendamustine, uramustine, estramustine, carmustine, lomustine, semustine, fotemustine, nimustine, ranimustine, streptozocin, busulfan, mannosulfan, treosulfan, carboquone, thioTEPA, triaziquone, triethylenemelamine, procarbazine, dacarbazine, temozolomide, altretamine, mitobronitol, actinomycin, bleomycin, mitomycin and plicamycin.

Examples of antibiotics include mitomycin, hydroxyurea; anthracyclines, anthracenediones, *streptomyces* family. Examples of anthracyclines include doxorubicin, daunorubicin, epirubicin and other derivatives; examples of anthracenediones include mitoxantrone and relatives; examples of *streptomyces* family include bleomycin, mitomycin C, and actinomycin.

Examples of PARP inhibitors include inhibitors of PARP1 and PARP2. Specific examples include olaparib (also known as AZD2281 or KU-0059436), iniparib (also known as BSI-201 or SAR240550), veliparib (also known as ABT-888), rucaparib (also known as PF-01367338), CEP-9722, INO-1001, MK-4827, E7016, BMN-673, or AZD2461. In other embodiments, the agent that inhibits or modulates PARP1 or PARP2 is Veliparib (also known as ABT-888) or Rucaparib. In other embodiments, the agent that inhibits or modulates PARP1 or PARP2 is BMN-673.

In certain embodiments, said platinating agent is cisplatin or oxaliplatin; said topoisomerase I inhibitor is camptothecin; said topoisomerase II inhibitor is etoposide; and said antibiotic is mitomycin. In other embodiments, said platinating agent is selected from cisplatin, oxaliplatin, carboplatin, nedaplatin, or satraplatin; said topoisomerase I inhibitor is selected from camptothecin, topotecan, irinotecan/SN38, rubitecan; said topoisomerase II inhibitor is selected from etoposide; said antimetabolite is selected from a member of the folic family, the purine family, or the pyrimidine family; said alkylating agent is selected from nitrogen mustards, nitrosoureas, triazenes, alkyl sulfonates, procarbazine, or aziridines; and said antibiotic is selected from hydroxyurea, anthracyclines, anthracenediones, or *streptomyces* family.

In some embodiments, the additional therapeutic agent is radiation (e.g., ionizing radiation). In other embodiments, the additional therapeutic agent is cisplatin or carboplatin. In yet other embodiments, the additional therapeutic agent is etoposide. In yet other embodiments, the additional therapeutic agent is temozolomide.

In some embodiments, the additional therapeutic agents are selected from those that inhibit or modulate a base excision repair protein. In a specific embodiment, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin. In another specific embodiment, the base excision repair protein is selected from PARP1, PARP2, or PolB. In yet another embodiment, the base excision repair protein is selected from PARP1 or PARP2.

In some embodiments, the method is used on a cancer cell having defects in the ATM signaling cascade. In some embodiments, said defect is altered expression or activity of one or more of the following: ATM, p53, CHK2, MRE11, RAD50, NBS1, 53BP1, MDC1, H2AX, MCPH1/BRIT1, CTIP, or SMC1. In other embodiments, said defect is altered expression or activity of one or more of the following: ATM, p53, CHK2, MRE11, RAD50, NBS1, 53BP1, MDC1 or H2AX. In another embodiment, the cell is a cancer cell expressing DNA damaging oncogenes. In some embodiments, said cancer cell has altered expression or activity of one or more of the following: K-Ras, N-Ras, H-Ras, Raf, Myc, Mos, E2F, Cdc25A, CDC4, CDK2, Cyclin E, Cyclin A and Rb.

According to another embodiment, the method is used on a cancer, cancer cell, or cell has a defect in a protein involved in base excision repair ("base excision repair protein"). There are many methods known in the art for determining whether a tumor has a defect in base excision repair. For example, sequencing of either the genomic DNA or mRNA products of each base excision repair gene (e.g., UNG, PARP1, or LIG1) can be performed on a sample of the tumor to establish whether mutations expected to modulate the function or expression of the gene product are present (Wang et al., Cancer Research 52:4824 (1992)). In addition to the mutational inactivation, tumor cells can modulate a DNA repair gene by hypermethylating its promoter region, leading to reduced gene expression. This is most commonly assessed using methylation-specific polymerase chain reaction (PCR) to quantify methylation levels on the promoters of base excision repair genes of interest. Analysis of base excision repair gene promoter methylation is available commercially (e.g., sabiosciences.com/dna_methylation_product/HTML/MEAH-421A).

The expression levels of base excision repair genes can be assessed by directly quantifying levels of the mRNA and protein products of each gene using standard techniques such as quantitative reverse transcriptase-coupled polymerase chain reaction (RT-PCR) and immunohistochemistry (IHC), respectively (Shinmura et al., Carcinogenesis 25: 2311 (2004); Shinmura et al., Journal of Pathology 225:414 (2011)).

In some embodiments, the base excision repair protein is UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

In some embodiments, the base excision repair protein is PARP1, PARP2, or PolB. In other embodiments, the base excision repair protein is PARP1 or PARP2.

In certain embodiments, the additional therapeutic agent is selected from one or more of the following: cisplatin, carboplatin, gemcitabine, etoposide, temozolomide, or ionizing radiation.

In other embodiments, the additional therapeutic agents are selected from one or more of the following: gemcitabine, cisplatin or carboplatin, and etoposide. In yet other embodiments, the additional therapeutic agents are selected from one or more of the following: cisplatin or carboplatin, etoposide, and ionizing radiation. In some embodiments, the cancer is lung cancer. In some embodiments, the lung cancer is non-small cell lung cancer or small cell lung cancer.

In some embodiments, the anticancer therapies for the combination therapy of the invention include DNA-damaging agents, such as topoisomerase inhibitors (e.g. etoposide and doxil), DNA intercalators (e.g., doxorubicin, daunorubicin, and epirubicin), radiomimetics (e.g., bleomycin), PARP inhibitors (e.g., BMN-673), DNA-repair inhibitors (e.g., carboplatin), DNA cross-linkers (e.g., cisplatin), inhibitors of thymidylate synthase (e.g., fluorouracil (5-FU)), mitotic inhibitors (e.g., paclitaxel), EGFR inhibitors (e.g., erlotinib), EGFR monoclonal antibodies (e.g., cetuximab), and radiation (e.g., ionizing radiation). Specific examples include etoposide, doxil, gemcitabine, paclitaxel, cisplatin, carboplatin, 5-FU, etoposide, doxorubicin, daunorubicin, epirubicin, bleomycin, BMN-673, carboplatin, erlotinib, cisplatin, carboplatin, fluorouracil cetuximab, and radiation (e.g., ionizing radiation). In some embodiments, compounds of formula I and co-crystals thereof are used in combination with at least one anticancer drug selected from etoposide, doxil, gemcitabine, paclitaxel, cisplatin, carboplatin, 5-FU, etoposide, doxorubicin, daunorubicin, epirubicin, bleomycin, BMN-673, carboplatin, erlotinib, cisplatin, carboplatin, fluorouracil, or cetuximab, and with or without radiation. In some specific embodiments, compounds of formula I and co-crystals thereof are used in combination with etoposide and cisplatin, with or without radiation (e.g., ionizing radiation). In some specific embodiments, compounds of formula I and co-crystals thereof are used in combination with paclitaxel and cisplatin, with or without radiation (e.g., ionizing radiation). In some specific embodiments, compounds of formula I and co-crystals thereof are used in combination with paclitaxel and carboplatin, with or without radiation (e.g., ionizing radiation). In some specific embodiments, compounds of formula I and co-crystals thereof are used in combination with cisplatin and 5-Fu, with or without radiation (e.g., ionizing radiation).

Specific examples of cancers for the combination therapy are as described above. In some embodiments, the invention is employed for treating lung cancer (e.g., non-small cell lung cancer (NSCLC), extensive-disease small cell lung cancer (ED-SCLC)), breast cancer (e.g., triple negative breast cancer), prostate cancer, acute myeloid leukemia, myeloma, esophageal cancer (e.g., gastro-esophageal junction cancer (GEJ)), ovarian cancer, colon cancer, pharynx cancer, pancreatic cancer, lung fibroblast, and gastric cancer. In some specific embodiments, the invention is employed for treating lung cancer (e.g., non-small cell lung cancer (NSCLC), extensive-disease small cell lung cancer (ED-SCLC)), breast cancer (e.g., triple negative breast cancer), prostate cancer, acute myeloid leukemia, myeloma, gastro-esophageal junction cancer (GEJ), pancreatic cancer, and ovarian cancer.

In some specific embodiments, the invention provides co-therapy of the compounds of formula I and co-crystals thereof in combination with standard of care (e.g., doxorubicin, etoposide, paclitaxel, and/or carboplatin), with or without radiation (e.g., ionizing radiation), for treating lung cancer, such as non-small cell lung cancer (NSCLC) or extensive-disease small cell lung cancer (ED-SCLC).

In some specific embodiments, the invention provides co-therapy of the compounds of formula I and co-crystals thereof in combination with standard of care (e.g. cisplatin, 5-FU, carboplatin, paclitaxel, and/or etoposide), with or without radiation (e.g., ionizing radiation), is employed for treating gastro-esophageal junction cancer (GEJ).

In some specific embodiments, the invention provides co-therapy of the compounds of formula I and co-crystals thereof in combination with standard of care (e.g., doxorubicin and/or vincristine), with or without radiation (e.g., ionizing radiation), in acute myeloid leukemia or chronic lymphocytic leukemia.

In some specific embodiments, the invention provides co-therapy of the compounds of formula I and co-crystals thereof in combination with standard of care (e.g., doxorubicin and/or epirubicin), with or without radiation (e.g., ionizing radiation), in breast cancer, such as triple negative breast cancer.

In some specific embodiments, the invention provides combination therapy of the compounds of formula I and co-crystals thereof in combination with radiation (or ionizing radiation); cisplatin, etoposide, paclitaxel, doxorubicin or cetuximab, with or without radiation (e.g., ionizing radiation); cisplatin and etoposide, with or without radiation (e.g., ionizing radiation); or cisplatin and paclitaxel, with or without radiation (e.g., ionizing radiation), for lung cancer, such as non-small cell lung cancer (NSCLC), small cell lung cancer, or extensive-disease small cell lung cancer (ED-SCLC).

In some specific embodiments, the invention provides combination therapy of the compounds of formula I and co-crystals thereof in combination with radiation (e.g., ionizing radiation); cisplatin with or without radiation (e.g., ionizing radiation); etoposide with or without radiation (e.g., ionizing radiation); carboplatin with or without radiation (e.g., ionizing radiation); 5-FU with or without radiation (e.g., ionizing radiation); cisplatin and paclitaxel, with or without radiation (e.g., ionizing radiation); cisplatin and 5-FU, with or without radiation (e.g., ionizing radiation); or carboplatin and paclitaxel, with or without radiation (e.g., ionizing radiation), for gastro-esophageal junction cancer (GEJ).

In some specific embodiments, the invention provides combination therapy of the compounds of formula I and co-crystals thereof in combination with doxorubicin or epirubicin, with or without radiation (e.g., ionizing radiation), for breast cancer, such as triple negative breast cancer.

Another embodiment provides a method of treating breast cancer with the compounds of formula I and co-crystals thereof in combination with a platinating agent, with or without radiation (e.g., ionizing radiation). In some embodiments, the breast cancer is triple negative breast cancer. In other embodiments, the platinating agent is cisplatin.

In some specific embodiments, the invention provides combination therapy of the compounds of formula I and co-crystals thereof in combination with cetuximab, with or without radiation (e.g., ionizing radiation); or cisplatin with or without radiation (e.g., ionizing radiation), for pharynx cancer, for pharynx cancer.

In some specific embodiments, the invention provides combination therapy of the compounds of formula I and co-crystals thereof in combination with: cisplatin with or without radiation (e.g., ionizing radiation); etoposide with or without radiation (e.g., ionizing radiation); cisplatin and 5-FU, with or without radiation (e.g., ionizing radiation); or paclitaxel with or without radiation (e.g., ionizing radiation), for lung fibroblast.

In some specific embodiments, the invention provides combination therapy of the compounds of formula I and co-crystals thereof in combination with: radiation (e.g., ionizing radiation); bleomycin, doxorubicin, cisplatin, carboplatin, etoposide, paclitaxel or 5-FU, with or without radiation (e.g., ionizing radiation) for lung cancer, such as NSCLC, pancreatic cancer, esophageal cancer, or gastric cancer.

Another embodiment provides methods for treating pancreatic cancer by administering a compound described herein in combination with another known pancreatic cancer treatment. One aspect of the invention includes administering a compound described herein in combination with gemcitabine.

Co-administration in the combination therapies encompasses administration of the first and second amounts of the compounds/therapies of the co-administration in an essentially simultaneous manner (such as in a single pharmaceutical composition, for example, capsule or tablet having a fixed ratio of first and second amounts, or in multiple, separate capsules or tablets for each) or in a sequential manner in either order.

When co-administration involves the separate administration of the first amount of a compound of the invention and a second amount of an additional therapeutic agent/therapy, they are administered sufficiently close in time to have the desired therapeutic effect. The invention also can be practiced by including another anti-cancer chemotherapeutic agent in a therapeutic regimen for the treatment of cancer, with or without radiation therapy. The combination of a co-crystal or pharmaceutical composition of the invention with such other agents can potentiate the chemotherapeutic protocol. For example, the inhibitor compound of the invention can be administered with etoposide, bleomycin, doxorubicin, epirubicin, daunorubicin, or analogs thereof, agents known to cause DNA strand breakage.

In some embodiments, the compounds of formula I and co-crystals thereof used in combination with a DNA-damaging agent (e.g., etoposide, radiation), and the compounds of formula I and co-crystals thereof are administered after the administration of the DNA-damaging therapy. Specific examples of DNA-damaging agents are described above.

In some embodiments, the forementioned one or more additional anticancer agent or therapy is employed with Compound (1) or a pharmaceutically acceptable salt thereof. In some embodiments, the forementioned one or more additional anticancer agent or therapy is employed with Compound (2) or a pharmaceutically acceptable salt thereof. In some embodiments, the forementioned one or more additional anticancer agent or therapy is employed with the adipic acid co-crystal of Compound (1) (e.g., 2:1 Compound (1) to adipic acid). In some embodiments, the forementioned one or more additional anticancer agent or therapy is employed with the adipic co-crystal of Compound (2) (e.g., 2:1 Compound (2) to adipic acid).

In some embodiments, the forementioned one or more additional anticancer agent or therapy is employed with the pharmaceutical compositions of the invention described above.

Described below are examples of preparing and characterizing co-crystals of this invention, which are meant to be only illustrative and not to be limiting in any way.

Example 1: Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997. The following definitions describe terms and abbreviations used herein:

BPin pinacol boronate ester
Brine a saturated NaCl solution in water
DCM dichloromethane
DIEA diisopropylethylamine
DMA dimethylacetamide
DME dimethoxyethane
DMF dimethylformamide
DMSO methylsulfoxide
EtDuPhos (2R,5R)-1-[2-[(2R,5R)-2,5-diethylpholan-1-yl]phenyl]-2,5-diethylphospholane
ESMS electrospray mass spectrometry
$Et_2O$ ethyl ether
EtOAc ethyl acetate
EtOH ethyl alcohol
HPLC high performance liquid chromatography
IPA isopropanol
LC-MS liquid chromatography-mass spectrometry
Me methyl
MeOH methanol
MTBE methyl t-butyl ether
NMP N-methylpyrrolidine
$PdCl_2[P(cy)_3]_2$ dichloro-bis(tricyclohexylphosphoranyl)-palladium
Ph phenyl
RT or rt room temperature
TBME tert-butylmethyl ether
tBu tertiary butyl
THF tetrahydrofuran
TEA triethylamine
TMEDA tetramethylethylenediamine Example A. Preparation of 2-methyl-5-(4,4,5,5-tetramethyl-1,3,2-dioxaborolan-2-yl)pyrimidine-4,6-$d_2$ (Compound 1003)

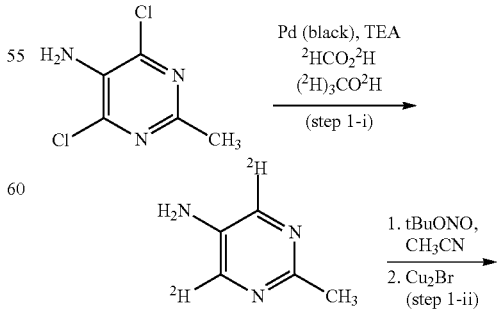

[1001]

-continued

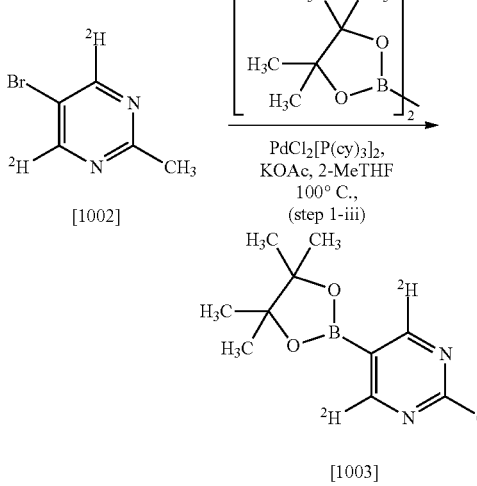

As shown in step 1-i of Scheme 1, to a solution of 4,6-dichloro-2-methyl-pyrimidin-5-amine (14.04 g, 78.88 mmol) stirred in methanol-$d_4$ (140.4 mL) was added formic acid-$d_2$ (7.77 g, 161.7 mmol) and Pd black (765 mg, 7.19 mmol, wetted in methanol-$d_4$), followed by triethylamine (16.36 g, 22.53 mL, 161.7 mmol). The reaction mixture was sealed in a tube and stirred at RT overnight. The mixture was then filtered and concentrated under reduced pressure. $Et_2O$ (250 mL) was added and the mixture stirred for 1 hour at RT. The resulting solids were filtered and washed with $Et_2O$ (×2). The filtrate was concentrated under reduced pressure to yield 4,6-dideutero-2-methyl-pyrimidin-5-amine (Compound 1001, 5.65 g, 65% yield) as a light yellow solid: $^1$H NMR (300 MHz, DMSO-$d_6$) δ 5.25 (s, 2H), 2.40 (s, 3H). This compound was used in subsequent steps without further purification.

As shown in step 1-ii of Scheme 1, to 4,6-dideutero-2-methyl-pyrimidin-5-amine (5.35 g, 48.14 mmol) in $CH_3CN$ (192.5 mL) was added dibromocopper (16.13 g, 3.38 mL, 72.21 mmol) followed by t-butylnitrite (8.274 g, 9.54 mL, 72.21 mmol). After 1 hour, the reaction was filtered through diatomaceous earth with dichloromethane. The filtrate was washed with water/brine (1:1), the organic layer separated, the aqueous layer extracted with dichloromethane (2×), and the combined organic layers filtered through diatomaceous earth and concentrated under reduced pressure. The crude product was purified by medium pressure silica gel column chromatography (0-10% EtOAc/hexanes) to yield 5-bromo-4,6-dideutero-2-methyl-pyrimidine (Compound 1002, 4.1 g, 49% yield): $^1$H NMR (300 MHz, methanol-$d_4$) δ 2.64 (s, 3H).

As shown in step 1-iii of Scheme 1, a mixture of 5-bromo-4,6-dideutero-2-methyl-pyrimidine (8.5 g, 48.57 mmol), bis(pinacolato)diboron (13.57 g, 53.43 mmol), and KOAc (14.30 g, 145.7 mmol) in 2-methyltetrahydrofuran (102.0 mL) was degassed by flushing with nitrogen. To this was added dichloro-bis(tricyclohexylphosphoranyl)-palladium ($PdCl_2[P(cy)_3]_2$, 1.01 g, 1.364 mmol) and the reaction mixture stirred in a sealed tube overnight at 100° C. The mixture was filtered and the filtrate stirred with Silabond® DMT silica (SiliCycle, Inc., 0.58 mmol/g, 3.53 g) for 1 hour. The mixture was filtered and concentrated under reduced pressure to yield 2-methyl-4,6-dideutero-5-(4,4,5,5-tetramethyl-1,3,2-dioxaborolan-2-yl)pyrimidine (Compound 1003, 13.6 g, 72% purity, the major contaminant being pinacol) as a light yellow oil: $^1$H NMR (300 MHz, $CDCl_3$) δ 2.75 (s, 3H), 1.30 (s, 12H). This compound was used in subsequent steps without further purification.

Example B. Preparation of (S)-8-(1-((6-chloropyrimidin-4-yl)amino)propan-2-yl)-N-methylquinoline-4-carboxamide (Compound 1013)

Scheme 2

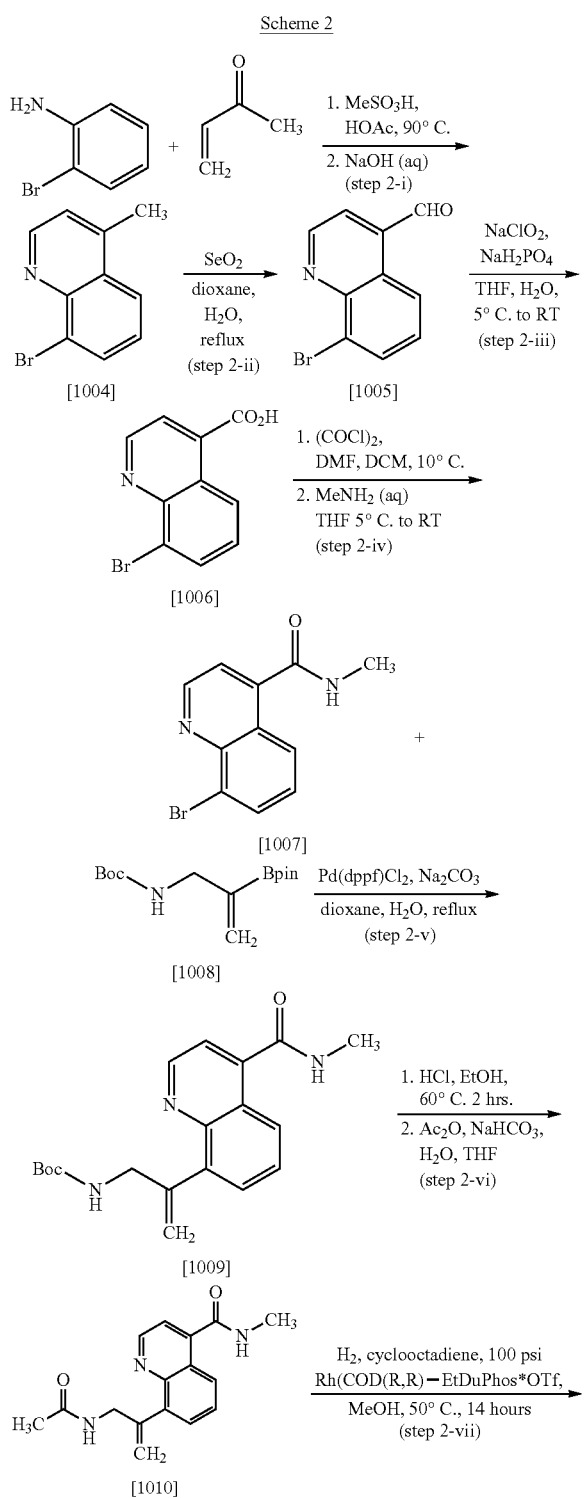

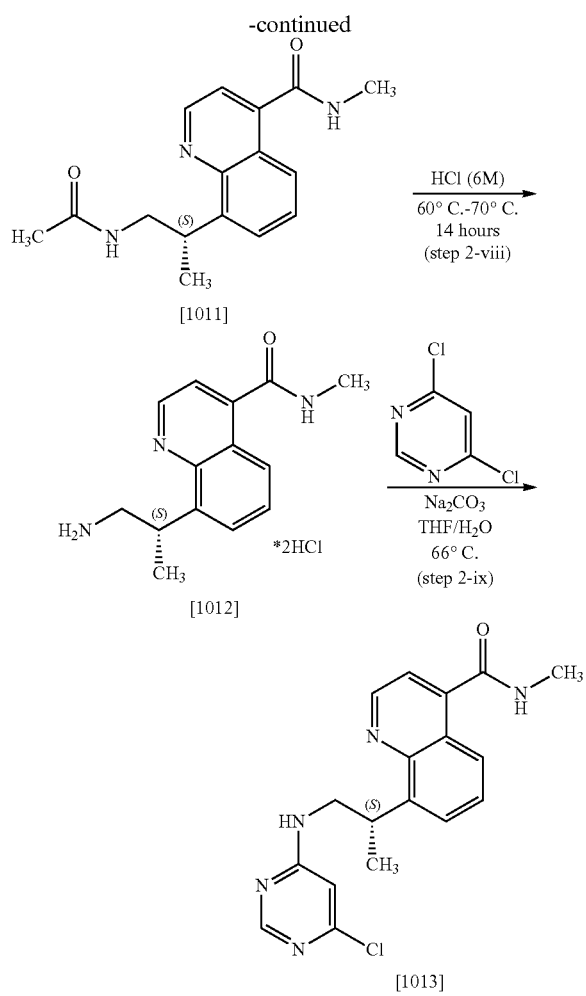

As shown in step 2-i of Scheme 2, 2-bromoaniline (520 g, 3.02 mol) was melted at 50° C. in an oven and then added to a reaction vessel containing stirring acetic acid (3.12 L). Methanesulfonic acid (871.6 g, 588.5 mL, 9.07 mol) was then added over 15 minutes. The reaction mixture was heated to 60° C. and methyl vinyl ketone (377 mL, 1.5 equiv.) was added over 5 minutes and the reaction mixture stirred for 1 hour at 90° C. After this time another 50 mL (0.2 equiv.) of methyl vinyl ketone was added and the reaction mixture stirred for an additional 16 hours. The resulting dark brown solution was cooled with an ice-water bath and poured portion-wise into a stirring solution of 50% w/w aq. NaOH (3.894 L, 73.76 mol) and ice (1 kg) also cooled with an ice-water bath. Additional ice was added as required during addition to maintain the reaction temperature below 25° C. After addition was complete the reaction mixture (pH>10) was stirred for 30 minutes whilst cooling in an ice/water bath. A precipitate formed which was collected by filtration, washed with water (2 L×3), and dissolved in DCM (4 L). The organics were washed with water (2 L) and the aqueous phase back-extracted with DCM (1 L). The combined organics were dried over $Na_2SO_4$, filtered through a pad of silica gel (about 2 L), eluted with DCM and then 3% EtOAc/DCM until all of the product came through the plug. The volatiles of the filtrate were removed at reduced pressure and the residue was triturated with hexanes (about 500 mL). The resulting solid was collected by filtration, washed with hexanes (4×500 mL), and dried under vacuum to yield 8-bromo-4-methylquinoline (Compound 1004, 363 g, 54% yield) as a light tan solid: LC-MS=222.17 (M+H); $^1$H NMR (300 MHz, $CDCl_3$) δ 8.91 (d, J=4.3 Hz, 1H), 8.06 (d, J=7.4 Hz, 1H), 7.99 (d, J=8.4 Hz, 1H), 7.42 (t, J=7.9 Hz, 1H), 7.30 (d, J=4.2 Hz, 1H), 2.73 (s, 3H).

As shown in step 2-ii of Scheme 2, selenium dioxide (764.7 g, 6.754 mol) was taken up in 3.25 L of dioxane and 500 mL of water. The stirred solution was heated to 77° C. and 8-bromo-4-methylquinoline (compound 1004, 500 g, 2.251 mol) was added in one portion. The reaction mixture was stirred at reflux for 30 minutes and then cooled with a water bath to about 45° C., at which temperature a precipitate was observed. The suspension was filtered through diatomaceous earth which was subsequently washed with the hot THF to dissolve any residual solids. The filtrate was concentrated to a minimum volume under reduced pressure and 2M NaOH (2.81 L, 5.63 mol) was added to achieve a pH of 8 to 9. The reaction mixture was stirred at this pH for 30 minutes. A precipitate resulted which was collected by filtration and air-dried overnight to produce 8-bromoquinoline-4-carbaldehyde (compound 1005) as an yellowish solid: MS=236.16 (M+H); $^1$H NMR (300 MHz, $CDCl_3$) δ 10.52 (s, 1H), 9.34 (d, J=4.2 Hz, 1H), 9.05 (dd, J=8.5, 1.2 Hz, 1H), 8.18 (dd, J=7.5, 1.3 Hz, 1H), 7.88 (d, J=4.2 Hz, 1H), 7.60 (dd, J=8.5, 7.5 Hz, 1H). This material was used as is in subsequent reactions.

As shown in step 2-iii of Scheme 2, to a stirred suspension of 8-bromoquinoline-4-carbaldehyde (531.4 g, 2.25 mol) in THF (4.8 L) was added water (4.8 L) and monosodium phosphate (491.1 g, 4.05 mol). The mixture was cooled to 5° C. and, keeping the reaction temperature below 15° C., sodium chlorite (534.4 g, 4.727 mol) was slowly added portionwise as a solid over about 1 hour. After addition was complete the reaction mixture was stirred at 10° C. for 1 hour followed by the portionwise addition of 1N $Na_2S_2O_3$ (1.18 L) whilst keeping the temperature below 20° C. The reaction mixture was stirred at RT followed by the removal of the THF under reduced pressure. The resulting aqueous solution containing a precipitate was treated with sat'd $NaHCO_3$ (about 1 L) until a pH of 3 to 4 was achieved. This mixture was stirred an additional 15 minutes and the solid was collected by filtration, washed with water (2×1 L), washed with tert-butyl methyl ether (2×500 mL), and dried in a convection oven at 60° C. for 48 hours. Additional drying under high vacuum provided 8-bromoquinoline-4-carboxylic acid (compound 1006, 530.7 g, 94% yield from compound 1004) as a yellowish tan solid: LC-MS=252.34 (M+H); $^1$H NMR (300 MHz, DMSO-$d_6$) δ 14.09 (s, 1H), 9.16 (d, J=4.4 Hz, 1H), 8.71 (dd, J=8.6, 1.2 Hz, 1H), 8.25 (dd, J=7.5, 1.2 Hz, 1H), 8.03 (d, J=4.4 Hz, 1H), 7.64 (dd, J=8.6, 7.5 Hz, 1H).

As shown in step 2-iv of Scheme 2, to a suspension of 8-bromoquinoline-4-carboxylic acid (compound 1006, 779.4 g, 3.092 mol) in DCM (11.7 L) was added anhydrous DMF (7.182 mL, 92.76 mmol). The reaction mixture was cooled to 10° C. and oxalyl chloride (413 mL, 4.638 mol) was added dropwise over 30 minutes. The reaction mixture was stirred an additional 30 minutes after addition was complete, transferred to an evaporation flask, and the volatiles removed under reduced pressure. Anhydrous THF (2 L) was added and the volatiles were once more removed under reduced pressure in order to remove any residual oxalyl chloride. Anhydrous THF was added to the residue under an atmosphere of nitrogen and the resulting suspension of intermediate 8-bromoquinoline-4-carboxylic acid chloride was stored for later use. Separately, the original reaction flask was thoroughly flushed with nitrogen gas to remove any residual oxalyl chloride and the flask charged with dry THF (1.16 L). After cooling to 5° C., aqueous methyl amine (2.14 L of 40% w/w MeNH$_2$/water, 24.74 mol) was added followed by the addition of additional THF (1.16 L). To this solution was added portionwise over 1 hour the intermediate acid chloride suspension, keeping the reaction mixture temperature below 20° C. during addition. The evaporation vessel used to store the acid chloride was rinsed with anhydrous THF and aqueous MeNH$_2$ (500 mL) and this added to the reaction mixture, which was allowed to come to room temperature over 16 hours. The organic volatiles were removed under reduced pressure and the remaining mostly aqueous suspension diluted with water (1.5 L). The solids were collected by filtration, washed with water until the filtrate had a pH of less than 11, washed with MTBE (2×800 mL), and dried in a convection oven at 60° C. to provide 8-bromo-N-methyl-quinoline-4-carboxamide (Compound 1007, 740.4 g, 90% yield) as a light brown solid: LC-MS=265.04 (M+H); $^1$H NMR (300 MHz, DMSO-d$_6$) δ 9.08 (d, J=4.3 Hz, 1H), 8.78 (d, J=4.7 Hz, 1H), 8.21 (dd, J=7.5, 1.2 Hz, 1H), 8.16 (dd, J=8.5, 1.3 Hz, 1H), 7.65 (d, J=4.3 Hz, 1H), 7.58 (dd, J=8.5, 7.5 Hz, 1H), 2.88 (d, J=4.6 Hz, 3H).

As shown in step 2-v of Scheme 2, 8-bromo-N-methyl-quinoline-4-carboxamide (Compound 1007, 722 g, 2.723 mol) and tert-butyl-N-[2-(4,4,5,5-tetramethyl-1,3,2-dioxaborolan-2-yl)allyl]carbamate (Compound 1008, 925.4 g, 3.268 mol) were combined in a reaction flask. Na$_2$CO$_3$ (577.2 g, 5.446 mol) was added followed by the addition of water (2.17 L). The mixture was stirred for 5 minutes, 1,4-dioxane (5.78 L) was added, and the mixture was deoxygenated by bubbling in a stream of nitrogen gas for 30 minutes. Pd(dppf) Cl$_2$/DCM (44.47 g, 54.46 mmol) was added and deoxygenation was continued as before for an additional 30 minutes. The reaction mixture was stirred at reflux for 16 hours, allowed to cool to 70° C., and water (5.42 L) was added. The mixture was cooled further with an ice-water bath and stirring continued at <10° C. for 2 hours. A precipitate resulted which was collected by filtration, washed with water (3×1 L), and washed with TBME (2×1 L). The resulting precipitate cake was split into two equal portions. Each portion was dissolved in THF/DCM (4 L) and poured onto a plug of Florisil® (3 L filtration funnel with about 1.5 L of Florisil, using DCM to wet plug). The plug was subsequently washed with MeTHF until it was determined by thin layer chromatography analysis that no product remained in the filtrate. The filtrates from both cake portions were combined and concentrated under reduced pressure to give an orange solid. TBME (1 L) was added and the resulting suspension was filtered. The collected solid was washed with 800 mL of TBME and dried under high vacuum overnight to provide tert-butyl (2-(4-(methylcarbamoyl)quinolin-8-yl)allyl)carbamate (Compound 1009, 653 g, 70% yield) as an off-white solid: LC-MS=342.31 (M+H); $^1$H NMR (300 MHz, CDCl$_3$) δ 8.93 (d, J=4.3 Hz, 1H), 8.17 (dd, J=8.4, 1.6 Hz, 1H), 7.68-7.53 (m, 2H), 7.41 (d, J=4.3 Hz, 1H), 6.09 (br. s, 1H), 5.54 (s, 1H), 5.28 (s, 1H), 5.10 (br. s, 1H), 4.33 (d, J=6.0 Hz, 2H), 3.11 (d, J=4.8 Hz, 3H), 1.38 (s, 9H). Additional product (34.9 g, 74% total yield) was obtained by concentrating the filtrate under reduced pressure, dissolving the residue in THF, filtering the solution through a plug of Florisil® as before, washing the plug with MeTHF, concentrating the filtrate under reduced pressure, adding 250 mL of TBME, stirring for 0.5 hours, collecting the resulting precipitate by filtration, washing the solid with EtOAc (40 mL), acetonitrile (50 mL), and drying the solid under high vacuum overnight.

As shown in step 2-vi of Scheme 2, to a stirring suspension of tert-butyl (2-(4-(methylcarbamoyl)quinolin-8-yl)allyl)carbamate (Compound 1009, 425 g, 1.245 mol) in EtOH (4.25 L) was added 5.5M HCl in iPrOH (1.132 L, 6.225 mol). The reaction mixture was stirred at reflux (76° C. internal temp) for 30 minutes and then over 90 minutes while it was allowed to cool to 40° C. EtOAc (2.1 L) was added and the mixture was stirred for an additional 2 hours. The solid was collected by filtration, washed with EtOAc, and dried under high vacuum to provide 8-(3-acetamidoprop-1-en-2-yl)-N-methylquinoline-4-carboxamide (Compound 1010, 357.9 g, 91% yield) as a tan solid: LC-MS=242.12 (M+H); $^1$H NMR (300 MHz, methanol-d$_4$) δ 9.07 (d, J=4.6 Hz, 1H), 8.27 (dd, J=8.5, 1.5 Hz, 1H), 7.89 (dd, J=7.2, 1.5 Hz, 1H), 7.81-7.72 (m, 2H), 5.85 (s, 1H), 5.75 (s, 1H), 4.05 (s, 2H), 3.04 (s, 3H).

As shown in step 2-vii of Scheme 2, under an atmosphere of nitrogen 8-(3-acetamidoprop-1-en-2-yl)-N-methylquinoline-4-carboxamide (12.4 g, 43.77 mmol) and cycloocta-1,5-diene/(2R,5R)-1-[2-[(2R,5R)-2,5-diethylpholan-1-yl]phenyl]-2,5-diethylpholane:rhodium(+1) cation-trifluoromethanesulfonate (Rh(COD)(R,R)-Et-DuPhos-OTf, 316.3 mg, 0.4377 mmol) in methanol (372.0 mL) were combined and warmed to 35-40° C. until the solids were solubilized. The reaction mixture was placed in a hydrogenation apparatus, the atmosphere replaced with hydrogen, and the mixture agitated under 100 p.s.i. of hydrogen at 50° C. for 14 hours. After cooling to RT, the mixture was filtered through a bed of Florisil®, which was subsequently washed with MeOH (2×50 mL). The filtrate was concentrated under reduced pressure and any trace water removed via a DCM azeotrope under reduced pressure. The residue was triturated with 20% DCM in MTBE (2×100 mL) to afford (S)-8-(1-acetamidopropan-2-yl)-N-methylquinoline-4-carboxamide (Compound 1011, 11.0 g, 88% yield, 96% e.e.) as an off-white solid: $^1$H-NMR (300 MHz, DMSO-d$_6$) δ 8.97 (d, J=4.3 Hz, 1H), 8.67 (d, J=4.7 Hz, 1H), 7.97 (dd, J=8.1, 1.5 Hz, 1H), 7.88 (t, J=5.6 Hz, 1H), 7.73-7.54 (m, 2H), 7.52 (d, J=4.3 Hz, 1H), 4.31 (dd, J=14.3, 7.1 Hz, 1H), 3.55-3.32 (m, 3H), 2.86 (d, J=4.6 Hz, 3H), 1.76 (s, 3H), 1.28 (d, J=7.0 Hz, 3H). The enantiomeric excess (e.e.) was determined by chiral HPLC (ChiralPac IC, 0.46 cm×25 cm], flow rate 1.0 mL/min for 20 min at 30° C. (20:30:50 methanol/ethanol/hexanes and 0.1% diethylamine) with a retention time for the (R)-enantiomer of 5.0 min, and for the (S)-enantiomer of 6.7 min.

As shown in step 2-viii of Scheme 2, (S)-8-(1-acetamidopropan-2-yl)-N-methylquinoline-4-carboxamide (11.0 g, 38.55 mmol) in 6M aqueous HCl (192.7 mL, 1.156 mol) was warmed to 60° C. After stirring for 2 days at this temperature, the reaction mixture was cooled and an additional 20 mL of 6M HCl was added. Stirring was continued for an additional 2 days at 70° C. The reaction mixture was cooled with an ice bath and the pH adjusted to about 11 with 6M NaOH (aq.). The aqueous mixture was extracted with 5% MeOH/DCM and the combined organic extracts washed with water (60 mL), brine (100 mL), dried over sodium sulfate, filtered, and concentrated under reduced pressure to afford crude product as a tan solid. This solid was suspended in EtOAc (200 mL), cooled to 3° C. with an ice bath, and 6M HCl/i-PrOH (30 mL) was added portionwise to produce a white precipitate which was collected by filtration. The solid was washed with EtOAc (100 mL) and dried under high vacuum to provide (S)-8-(1-aminopropan-2-yl)-N-methylquinoline-4-carboxamide, dihydrochloride [Compound 1012, 7.8 g, 61% yield, 95% purity (5% compound 1011)] as a white solid. This material was used as is in subsequent reactions.

As shown in step 2-ix of Scheme 2, 8-[(1S)-2-amino-1-methyl-ethyl]-N-methyl-quinoline-4-carboxamide, hydrochloride (compound 1012, 24.0 g, 72.86 mmol) was taken up in THF (230 mL) and water (40 mL) and stirred for 5 minutes. Sodium carbonate (15.44 g, 145.7 mmol) in 100 mL of water was added and the reaction mixture stirred for 10 minutes. 4,6-Dichloropyrimidine (12.18 g, 80.15 mmol) was added and the reaction mixture heated at reflux at 66° C. for 2 hours. The reaction mixture was cooled to RT, diluted with 200 mL of EtOAc, the organic layer separated, and the aqueous layer extracted with 100 mL EtOAc. The combined organics were washed with water (60 mL), brine (100 mL), dried over $Na_2SO_4$, filtered through a bed of silica gel (100 g), and concentrated under reduced pressure. The resulting crude product was triturated with 20% DCM in MBTE (200 mL) then MBTE (200 mL) to produce (S)-8-(1-((6-chloropyrimidin-4-yl)amino)propan-2-yl)-N-methylquinoline-4-carboxamide (Compound 1013, 23.15 g, 88% yield) as a white solid: $^1$H NMR (300 MHz, DMSO-$d_6$, 70° C.) δ 8.97 (d, J=4.3 Hz, 1H), 8.38 (s, 1H), 8.20 (s, 1H), 8.03 (d, J=8.5 Hz, 1H), 7.71 (d, J=6.8 Hz, 1H), 7.66-7.55 (m, 1H), 7.52 (d, J=4.2 Hz, 2H), 6.63 (s, 1H), 4.46 (dd, J=14.1, 7.1 Hz, 1H), 3.67 (s, 2H), 2.90 (d, J=4.6 Hz, 3H), 1.40 (d, J=7.0 Hz, 3H); $[α]_D^{24}$=44.77 (c=1.14, MeOH).

Example C. Preparation of (S)—N-methyl-8-(1-((2'-methyl-[4,5'-bipyrimidin]-6-yl-4',6'-$d_2$)amino)propan-2-yl)quinoline-4-carboxamide (Compound 2)

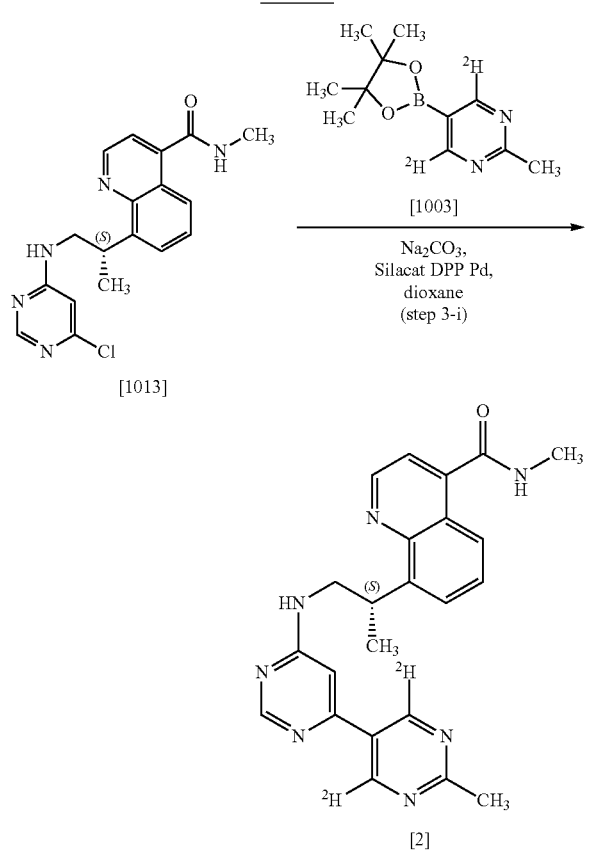

Scheme 3

[1013]

Na$_2$CO$_3$, Silacat DPP Pd, dioxane (step 3-i)

[2]

As shown in step 3-i of Scheme 3, (S)-8-(1-((6-chloropyrimidin-4-yl)amino)propan-2-yl)-N-methylquinoline-4-carboxamide (Compound 1013, 2.542 g, 7.146 mmol), 2-methyl-4,6-dideutero-5-(4,4,5,5-tetramethyl-1,3,2-dioxaborolan-2-yl)pyrimidine (Compound 1003, 2.204 g, 7.146 mmol, 72% by weight), Na$_2$CO$_3$ (10.72 mL of 2 M (aq.), 21.44 mmol), and Silacat® DPP Pd (SiliCycle, Inc., 1.429 g, 0.3573 mmol) were taken up in dioxane (30.00 mL), the solution flushed with nitrogen gas for 5 min, and the reaction mixture stirred at 90° C. for 16 hours. The mixture was filtered through diatomaceous earth, concentrated under reduced pressure, dissolved in DMSO, and purified by reversed-phase chromatography (10-40% CH$_3$CN/H$_2$O, 0.1% TFA). The product fractions were combined and DCM and MeOH were added, followed by the addition of 1N NaOH until a pH of greater than 7 was obtained. The product solution was extracted DCM (2×) and the combined extracts dried over Na$_2$SO$_4$, filtered, and concentrated under reduced pressure to yield (S)—N-methyl-8-(1-((2'-methyl-4',6'-dideutero-[4,5'-bipyrimidin]-6-yl)amino)propan-2-yl)quinoline-4-carboxamide (Compound 2, 181 mg, 28% yield) as an off-white solid: $^1$H NMR (300 MHz, DMSO-$d_6$, 70° C.) δ 8.95 (d, J=4.2 Hz, 1H), 8.47 (s, 1H), 8.01 (d, J=8.4 Hz, 1H), 7.74 (d, J=7.1 Hz, 1H), 7.59 (t, J=7.8 Hz, 1H), 7.50 (d, J=4.3 Hz, 1H), 7.30 (s, 1H), 7.03 (s, 1H), 4.51 (h, J=7.2 Hz, 1H), 3.78 (m, 2H), 2.88 (d, J=4.6 Hz, 3H), 2.68 (s, 3H), 1.41 (d, J=7.0 Hz, 3H). When 2-methyl-5-(4,4,5,5-tetramethyl-1,3,2-dioxaborolan-2-yl)pyrimidine was used in this reaction instead of deuterated Compound 1003, Compound 1 was produced: LCMS=414.40 (M+H); $^1$H NMR (300 MHz, DMSO-$d_6$, 70° C.) δ 9.14 (s, 2H), 8.95 (d, J=4.3 Hz, 1H), 8.47 (s, 1H), 8.34 (br. s, 1H), 8.02 (d, J=8.4 Hz, 1H), 7.74 (d, J=7.3 Hz, 1H), 7.59 (t, J=7.8 Hz, 1H), 7.50 (d, J=4.3 Hz, 1H), 7.28 (br. s, 1H), 7.04 (s, 1H), 4.52 (h, J=7.0 Hz, 1H), 3.83-3.66 (m, 2H), 2.88 (d, J=4.4 Hz, 3H), 2.68 (s, 3H), 1.42 (d, J=6.9 Hz, 3H).

Example 2: General Procedure for the Formation of Co-Crystals of a Compound of Formula I and a CCF Selected from Adipic Acid, Citric Acid, Fumaric Acid), Maleic Acid), Succinic Acid, or Benzoic Acid In general, the Co-crystals of the invention can be prepared by slurry crystallization or HME crystallization.

In one specific example, either Compound 1 or Compound 2 was weighed into vials and mixed with a CCF at a ratio of about 1:1.2, respectively, and stirred in a suitable solvent for 2 weeks. At the end of this time XRPD Analysis showed new crystalline patterns. Table 1 summarizes the compound ratios and concentrations for the formation of co-crystals of Compound 1.

TABLE 1

| Coformer | Weight CCF (mg) | Weight Compound 1 (mg) | Solvent | Volume (µL) |
|---|---|---|---|---|
| adipic acid | 6.12 | 14.0 | CH$_3$CN | 500 |
| succinic acid | 5.45 | 14.9 | CH$_3$CN | 500 |
| maleic acid | 5.14 | 15.0 | EtOAc | 500 |
| fumaric acid | 5.33 | 15.0 | CH$_3$CN | 500 |
| citric acid | 7.45 | 12.8 | EtOAc | 500 |
| benzoic acid | 5.25 | 14.8 | water | 500 |

Example 3: Preparation of Compounds 1 & 2/Adipic Acid Co-Crystal

A 1 liter jacketed vessel (with overhead stirring) was charged with Compound 1 (36.04 g, 0.087 mol, 1.000 equiv.), adipic acid (16.65 g, 0.114 mol, 2.614 equiv.), 1-propanol (321.00 g, 5.342 mol, 122.564 equiv.) and the slurry stirred at 750 rpm. A seed of the co-crystal (0.5% co-crystal seed) was added and the reaction mixture stirred at 25° C. Co-crystal formation was monitored by removing aliquots and analyzing by Raman spectroscopy. After 114 hours it was determined that co-crystal formation was complete. The slurry was filtered using a 600 mL Medium porosity fritted funnel until the solvent level was even with the wet cake. The mother liquor was isolated, labeled and analyzed for content. The wet cake was then washed with 1-propanol (270.0 mL, 7.49 vol.). The wet cake solids were weighed and dried in a vacuum oven at 50° C. The final yield of Compound 1/adipic acid co-crystal was 21.7 g. A similar procedure also produced a co-crystal of Compound 1 and adipic acid. HPLC analyses indicated a stoichiometry of about 2:1 for Compound 1 or Compound 2 to adipic acid.

Alternatively, the adipic acid co-crystals of Compound (1) was also prepared by HME crystallization. The HME crystallization proof-of-concept was made at the 20 g scale on a 16 mm extruder. Compound (1) freeform and neat adipic acid were extruded with high shear mixing and elevated temperatures (e.g., 144° C. or 155°) to generate cocrystal.

Certain physical properties of free base Compound (2) and its adipic co-crystal are summarized in Table 2 below.

TABLE 2

Material Properties of the Free Base and Adipic Acid Co-crystal of Compound (2)

| Material Assessment | Free Form | Adipic acid cocrystal Solvent crystallization process (80% Comp. 2:20% AA) (w/w) | Adipic acid cocrystal (80% Comp. 2:20% AA) (w/w) Hot melt extrusion process | Adipic acid cocrystal (75% Comp. 2:25% AA) (w/w) Hot melt extrusion process |
|---|---|---|---|---|
| Bulk Density | 0.33 g/cc | 0.14 g/cc | 0.43 g/cc | 0.62 g/cc |
| Tapped Density | 0.47 g/cc | 0.25 g/cc | 0.60 g/cc | 0.70 g/cc |

Example 4: X-Ray Powder Diffraction Characterization

The XRPD spectra for co-crystals of the invention (see FIGS. 1-7) were recorded at room temperature in reflection mode using a Bruker D8 Advance diffractometer equipped with a sealed tube Cu source and a Vantec PSD detector (Bruker AXS, Madison, Wis.). The X-ray generator was operating at a voltage of 40 kV and a current of 40 mA. The powder sample was placed in a silicon or PMM holder. The data were recorded over the range of 4°-45° 2 theta with a step size of 0.0140° and a dwell time of is per step. Fixed divergence slits of 0.2 mm were used.

The XRPD pattern for co-crystals Form A and Form B of the invention (see FIGS. 14 and 15) were recorded at room temperature in transmission mode using a PANanalytical Empyrean diffractometer equipped with a sealed tube Cu source and a PIXCel 1D detector. The X-ray generator was operating at a voltage of 45 kV and a current of 40 mA. The powder sample was placed in a transmission holder and held in place with Mylar thin films. The data were recorded over the range of 4°-40° 2-theta with a step size of 0.007° and a dwell time of 1549 s per step. The diffractometer was setup with 0.020 Solar slits, fixed ½° anti-scatter slits on the incident beam and ¼° anti-scatter slits on the diffracted side. Two scans were accumulated.

FIG. 1 shows an X-ray powder diffraction (XRPD) pattern of the co-crystal formed between Compound 1 with adipic acid. The XRPD pattern shows that the co-crystal is in a mixture of Forms A and B. Some specific XRPD peaks of the spectrum are summarized below.

TABLE 3

| No. | Pos. [°2Th.] | Rel. Int. [%] |
|---|---|---|
| 1 | 6.540282 | 61.33 |
| 2 | 7.858682 | 60.04 |
| 3 | 11.92977 | 52.67 |
| 4 | 12.2278 | 23.87 |
| 5 | 13.03317 | 29.49 |
| 6 | 14.22935 | 100 |
| 7 | 18.75679 | 59.81 |
| 8 | 19.0885 | 36.36 |

FIG. 2 shows an X-ray powder diffraction pattern of the co-crystal formed between Compound 2 with adipic acid. Some specific XRPD peaks of the pattern are summarized below.

TABLE 4

| No. | Pos. [°2Th.] | Rel. Int. [%] |
|---|---|---|
| 1 | 6.459033 | 55.29 |
| 2 | 7.911365 | 51.42 |
| 3 | 11.91567 | 45.41 |
| 4 | 12.25639 | 24.61 |
| 5 | 12.98715 | 34.47 |
| 6 | 14.19256 | 100 |
| 7 | 18.67692 | 38.85 |
| 8 | 19.06727 | 28.68 |

FIG. 3 shows an X-ray powder diffraction pattern of the co-crystal formed between Compound 1 with citric acid. Some specific XRPD peaks of the pattern are summarized below.

TABLE 5

| No. | Pos. [°2Th.] | Rel. Int. [%] |
|---|---|---|
| 1 | 7.435926 | 50.1 |
| 2 | 8.291282 | 19.41 |
| 3 | 11.35154 | 21.73 |
| 4 | 13.26446 | 100 |
| 5 | 15.49248 | 47.42 |
| 6 | 21.55281 | 20.72 |
| 7 | 23.57031 | 30.18 |

FIG. 4 shows an X-ray powder diffraction pattern of the co-crystal formed between Compound 1 and fumaric acid. Some specific XRPD peaks of the pattern are summarized below.

TABLE 6

| No. | Pos. [°2Th.] | Rel. Int. [%] |
|---|---|---|
| 1 | 8.264997 | 97.26 |
| 2 | 10.1077 | 23.4 |
| 3 | 14.97012 | 35.06 |
| 4 | 16.60917 | 41.79 |

TABLE 6-continued

| No. | Pos. [°2Th.] | Rel. Int. [%] |
|---|---|---|
| 5 | 17.21781 | 100 |
| 6 | 25.1975 | 67.75 |
| 7 | 26.01104 | 24.39 |

FIG. 5 shows an X-ray powder diffraction pattern of the co-crystal formed between Compound 1 and maleic acid. Some specific XRPD peaks of the pattern are summarized below.

TABLE 7

| No. | Pos. [°2Th.] | Rel. Int. [%] |
|---|---|---|
| 1 | 6.205335 | 15.27 |
| 2 | 10.43158 | 20.84 |
| 3 | 11.28478 | 40.95 |
| 4 | 12.41363 | 34.13 |
| 5 | 13.26101 | 19 |
| 6 | 18.86924 | 43.52 |
| 7 | 21.08017 | 31.35 |

FIG. 6 shows an X-ray powder diffraction pattern of the co-crystal formed between Compound 1 and succinic acid. Some specific XRPD peaks of the pattern are summarized below.

TABLE 8

| No. | Pos. [°2Th.] | Rel. Int. [%] |
|---|---|---|
| 1 | 8.01725 | 26.29 |
| 2 | 12.33839 | 42.72 |
| 3 | 14.77709 | 37.21 |
| 4 | 17.31539 | 12.09 |
| 5 | 19.56132 | 13.66 |
| 6 | 20.05503 | 100 |

FIG. 7 shows an X-ray powder diffraction pattern of the co-crystal formed between Compound 1 and benzoic acid. Some specific XRPD peaks of the pattern are summarized below.

TABLE 9

| No. | Pos. [°2Th.] | Rel. Int. [%] |
|---|---|---|
| 1 | 8.699594 | 88.63 |
| 2 | 13.90495 | 68.65 |
| 3 | 15.6186 | 80.96 |
| 4 | 17.6481 | 100 |
| 5 | 18.15049 | 41.75 |
| 6 | 20.76838 | 39 |
| 7 | 24.72293 | 67.36 |

Example 5: Thermogravimetric Analysis

Thermogravimetric Analyses (TGA) were conducted on a TA Instruments model Q5000 thermogravimetric analyzer. Approximately 1-4 mg of solid sample was placed in a platinum sample pan and heated in a 90 mL/min nitrogen stream at 10° C./min to 300° C. All thermograms were analyzed using TA Instruments Universal Analysis 2000 software V4.4A.

Figure 8:
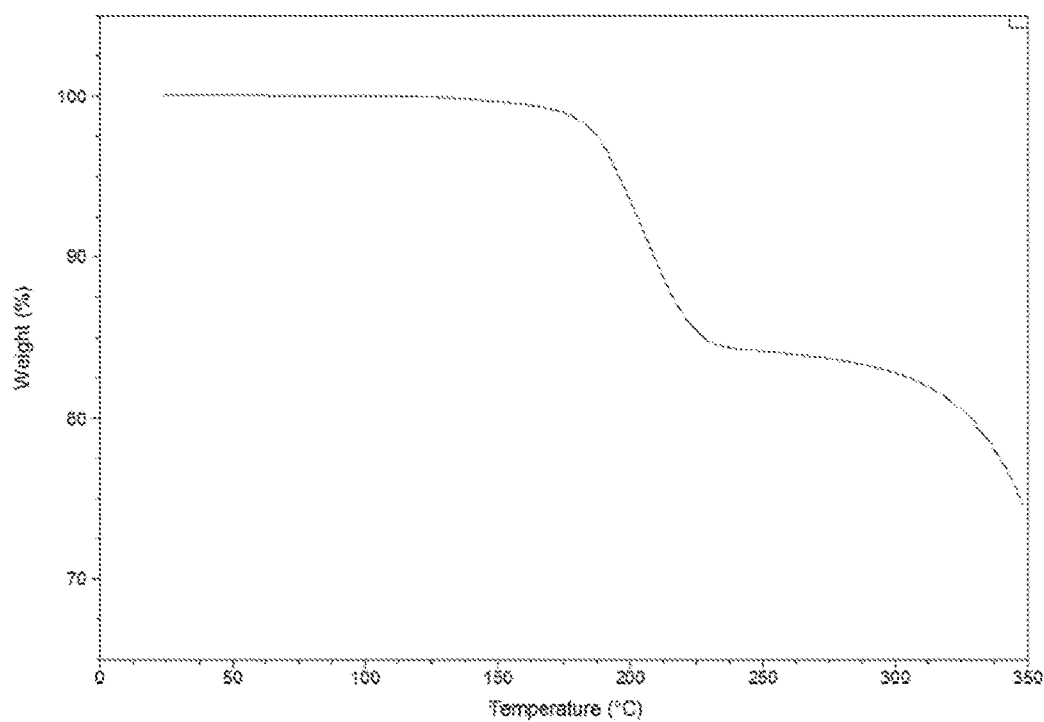
FIG. 8 shows a thermogravimetric analysis thermogram of the co-crystal formed between Compound 1 and adipic acid.
Figure 9:
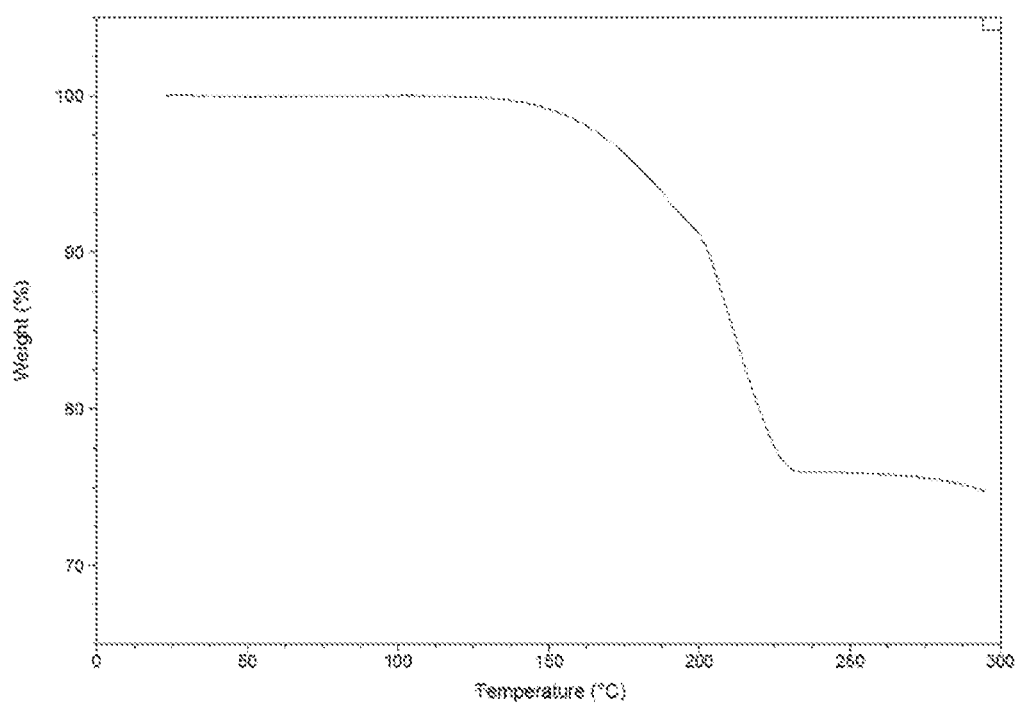
FIG. 9 shows a thermogravimetric analysis thermogram of the co-crystal formed between Compound 2 and adipic acid.

The thermo gravimetric analysis curves for the co-crystals of Compound (1) and adipic acid and for the co-crystals of Compound (2) and adipic acid are shown in FIGS. 8 and 9, respectively. The figures show loss of adipic acid starting at about 150° C. in both co-crystals.

Example 6: Differential Scanning Calorimetry

Differential Scanning Calorimetry (DSC) was conducted on a TA Instruments model Q2000 calorimetric analyzer. About 1-4 mg of solid sample was placed in a crimped aluminum pinhole pan and heated in a 50 mL/min nitrogen stream at 10° C./min to 300° C. All data were analyzed using TA Instruments Universal Analysis 2000 software V4.4A.

Figure 10:
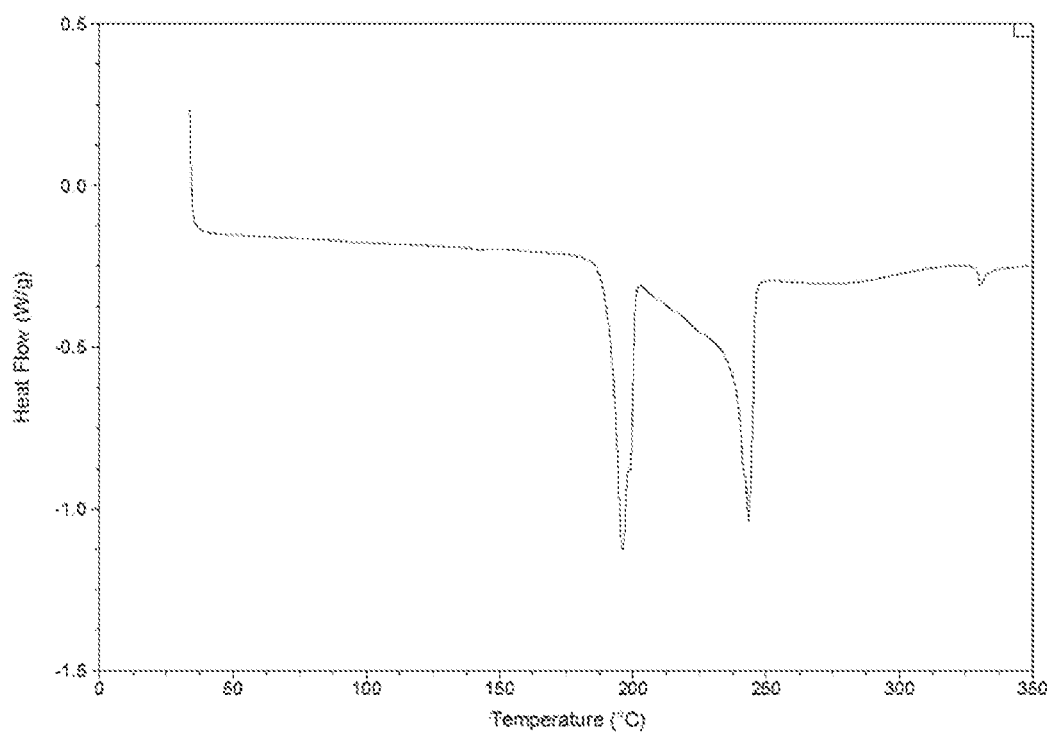
FIG. 10 shows a differential scanning calorimetry thermogram of the co-crystal formed between Compound 1 and adipic acid.
Figure 11:
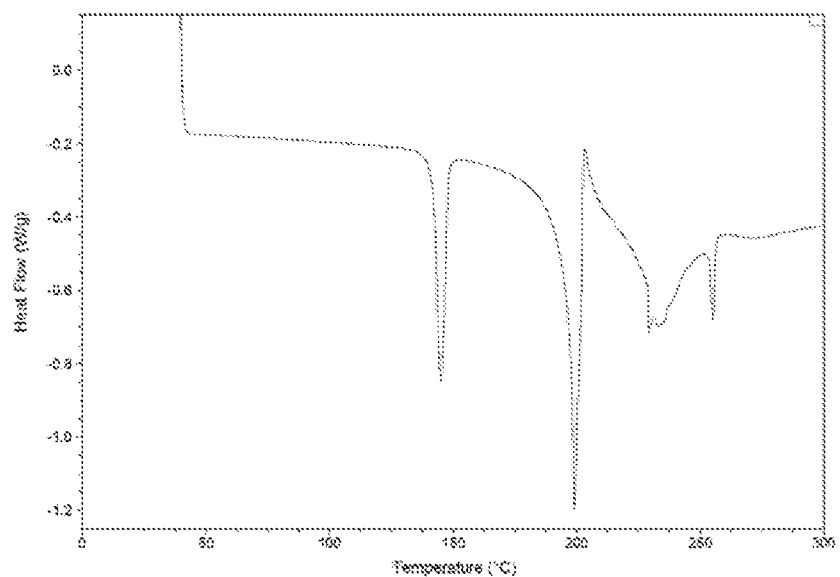
FIG. 11 shows a differential scanning calorimetry thermogram of the co-crystal formed between Compound 2 with adipic acid.

Representative differential scanning calorimetry thermograms are shown in FIG. 10 and FIG. 11 for the co-crystals of Compound (1) and adipic acid and for the co-crystals of Compound (2) and adipic acid, respectively.

Example 7: Solid State Nuclear Magnetic Resonance Spectroscopy

Solid state NMR spectra (ss-NMR) were acquired on the Bruker-Biospin 400 MHz Advance III wide-bore spectrometer equipped with Bruker-Biospin 4 mm HFX probe. Approximately 70 mg of each sample was packed into full volume Bruker-Biospin 4 mm ZrO2 rotors. A magic angle spinning (MAS) speed of typically 12.5 kHz was applied. The temperature of the probe head was set to 275° K to minimize the effect of frictional heating during spinning. A relaxation delay of 30 s seconds was used for all experiments. The CP contact time of $^{13}$C CPMAS experiment was set to 2 ms. A CP proton pulse with linear ramp (from 50% to 100%) was employed. The Hartmann-Hahn match was optimized on external reference sample (glycine). SPINAL 64 decoupling was used with the field strength of approximately 100 kHz. The chemical shift was referenced against external standard of adamantane with its upfield resonance set to 29.5 ppm.

Figure 12:
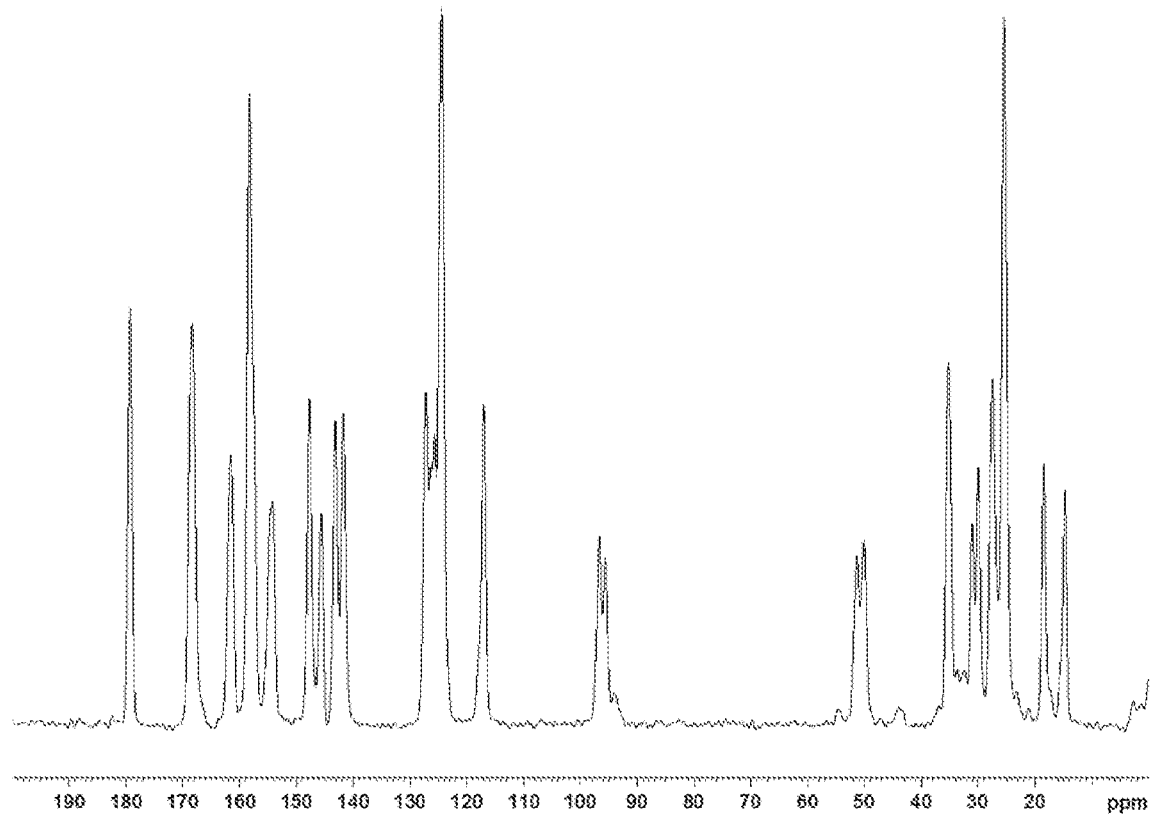
FIG. 12 shows a solid-state NMR spectrum of the co-crystal formed between Compound 1 and adipic acid.
Figure 13:
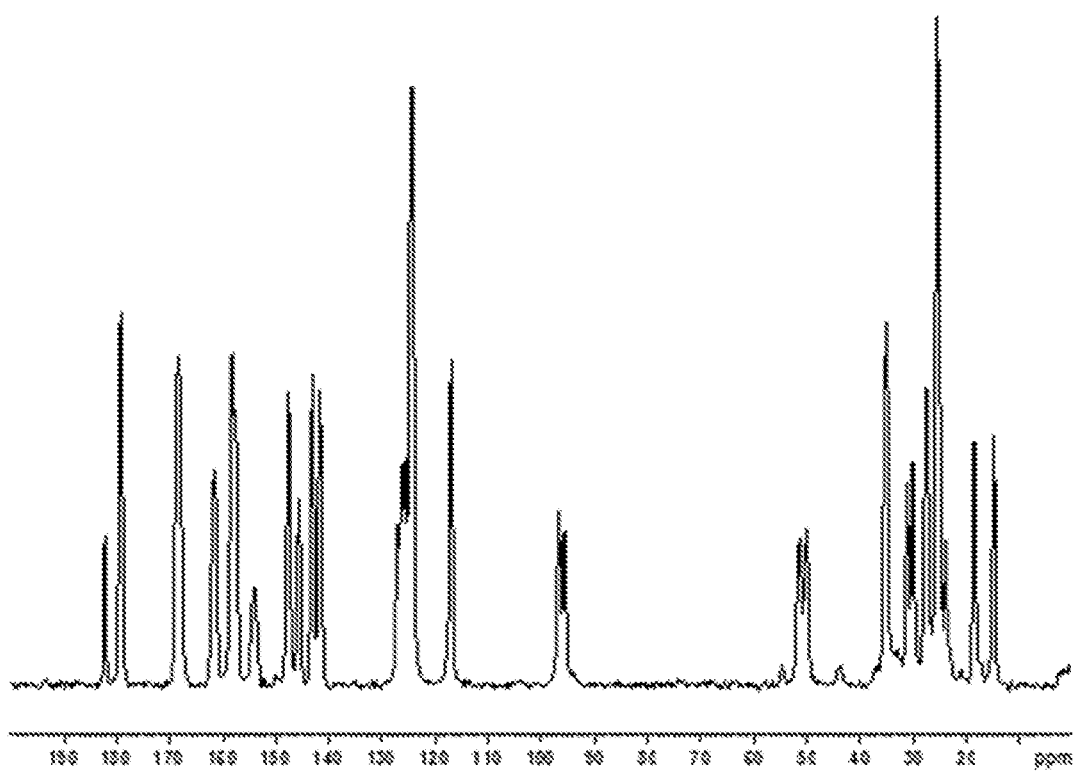
FIG. 13 shows a solid-state NMR spectrum of the co-crystal formed between Compound 2 and adipic acid.

Following washing with solvent, ss-NMR was used to investigate the co-crystal complexes of Compound 1 or Compound 2 with adipic acid. See FIGS. 12 and 13, respectively. The absence of peaks characteristic of free Compound 1, Compound 2, or adipic acid indicated pure cocrystal.

Example 8: Preparation of Polymorphic Forms A and B of Adipic Acid Co-Crystals of Compounds (1) and (2)

A. Preparation of Polymorphic Form A of Adipic Acid Co-Crystal of Compound (1)

Polymorphic Form A of adipic acid co-crystal of Compound (1) can be obtained by hot-melt crystallization of Compound (1) and adipic acid. A specific example of the preparation of Form A by hot melt extrusion is described below.

Adipic acid was jet milled using a Fluid Energy Model 00 Jet-O-Mizer using following settings:

| Parameter | Pressure [PSI] |
|---|---|
| Air Supply | 100 |
| Grinding nozzle | 60 |
| Pusher nozzle | 80 |

Compound (1) was screened through a #18 mesh screen. Compound (1) and jet milled adipic acid were weighed to prepare binary blends at about 80, 75 and 65% weight:weight Compound (1). The initial blends were prepared by passed through a #30 screen and subsequent mixing in a turbular mixer for 5 minutes.

The blends were extruded using a Leistritz Nano 16 twin screw extruder with three temperature zones and equipped with a plunger feeder. The screw design contained conveying, pumping and 30° and 60° kneading elements. All experiments were performed without a die installed on the extruder. Temperature, screw speed and temperature were set as listed in the Table below. The temperature was set and controlled to the same value for all three heating elements. During the extrusion the torque was monitored and the screw speed was increased when the screw was at risk of seizing.

| Parameter | Setting |
| --- | --- |
| Feed Rate [ml/min] | 1.5 3.755 |
| Screw speed [rpm] | 20 to 150 |
| Temperature [° C.] | 110 130 144 155 |

Figure 14:
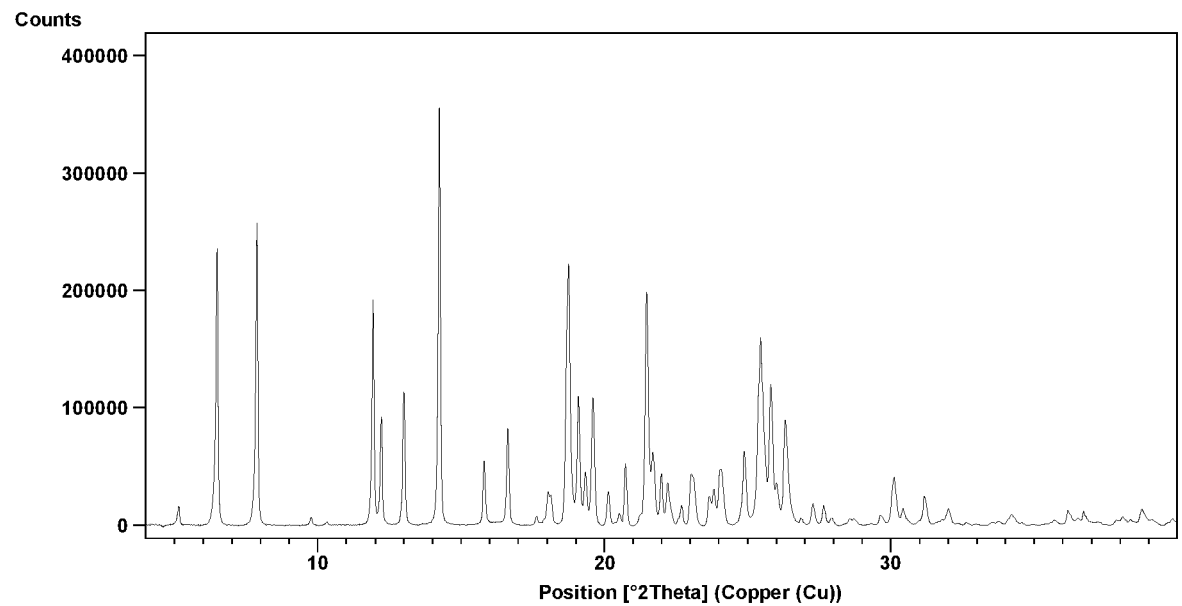
FIG. 14 shows an X-ray powder diffraction pattern of polymorphic Form A of the co-crystal formed between Compound 1 with adipic acid.

The transmission XRPD pattern and $^{13}$C NMR spectrum of Form A of adipic acid co-crystal of Compound (1) are shown in FIGS. 14 and 16, respectively. Certain peaks observed in the $^{13}$C NMR spectrum are summarized below.

TABLE 10

| Peak | Shift ±0.1 [ppm] | Intensity [% of max] |
| --- | --- | --- |
| 1 | 117.1 | 47.6 |
| 2 | 96.8 | 28.2 |
| 3 | 95.7 | 26.2 |
| 4 | 27.6 | 48.1 |
| 5 | 14.8 | 32.7 |
| 6 | 161.6 | 36.5 |
| 7 | 154.5 | 33.4 |
| 8 | 51.5 | 24.7 |
| 9 | 50.2 | 24.3 |
| 10 | 25.6 | 99.2 |
| 11 | 18.5 | 33.7 |
| 12 | 179.4 | 54.4 |
| 13 | 168.4 | 55.9 |
| 14 | 158.3 | 83.5 |
| 15 | 147.8 | 46.5 |
| 16 | 145.7 | 27.9 |
| 17 | 143.2 | 44.1 |
| 18 | 141.8 | 43.2 |
| 19 | 124.6 | 100.0 |
| 20 | 31.2 | 31.7 |
| 21 | 30.1 | 35.2 |

B. Preparation of Polymorphic Form A of Adipic Acid Co-Crystal of Compound (2)

Form A of adipic acid co-crystal of Compound (2) was prepared by acetone slurry. 322 mg of a mixture of Form A and Form B compound 2:adipic acid co-crystal prepared as described in Example 3 and 221 mg of adipic acid were stirred in 9.8 g of acetone at 20 to 30° C. for 30 days. Approximately 50 mg of solid was isolated by filter centrifugation through a 0.45 μm membrane filter using a centrifugal filter device and dried in vacuum at 20 to 30° C. for approximately 2 hours. Solid state NMR spectra were collected as described in Example 7 with the exception that the sample amount was approximately 50 mg and the relaxation delay was set to 5 s. The $^{13}$C NMR spectrum of Form A of adipic acid co-crystal of Compound (2) (see FIG. 17) is essentially the same as that of Form A of adipic acid co-crystal of Compound (1). Certain peaks observed in the $^{13}$C NMR spectrum are summarized below.

TABLE 11

| Peak | Shift ±0.1 [ppm] | Intensity [% of max] |
| --- | --- | --- |
| 1 | 116.9 | 48.3 |
| 2 | 96.6 | 27.4 |
| 3 | 95.6 | 23.9 |
| 4 | 27.5 | 45.6 |
| 5 | 14.7 | 36.7 |
| 6 | 161.4 | 32.9 |
| 7 | 153.9 | 15.9 |
| 8 | 51.3 | 22.5 |
| 9 | 49.9 | 22.2 |
| 10 | 25.4 | 100.0 |
| 11 | 18.3 | 35.8 |
| 12 | 179.2 | 55.6 |
| 13 | 168.2 | 49.5 |
| 14 | 158.2 | 48.2 |
| 15 | 147.6 | 46.0 |
| 16 | 145.5 | 27.1 |
| 17 | 143.1 | 45.7 |
| 18 | 141.6 | 44.6 |
| 19 | 124.4 | 91.9 |
| 20 | 31.0 | 30.9 |
| 21 | 29.9 | 33.4 |

C. Preparation of Polymorphic Form B of Adipic Acid Co-Crystal of Compound (2)

Polymorphic Form B of adipic acid co-crystal of Compound (2) can be obtained by employing spray drying. A specific example is described below.

A solvent mixture for spray drying was prepared by weighing out 50 g of methanol and 117.5 g dichloromehane into a glass bottle and shaking. 500 mg of Compound (2), 176.2 mg of adipic acid and 19.3 g of the methanol dichloromethane mixture were weighed into a clear glass vial and stirred until all solids were dissolved. This solution was spray dried using a Buchi mini spray drier B-290 using following setting:

| Parameter | Setting |
| --- | --- |
| Inlet Temp | 99° C. |
| Aspirator | 100% |
| Pump | 40% |
| Condenser | −5° C. |
| Nozzle | 1 mm |
| Atomizer | 35 mm |
| Filter Pressure | −60 mbar |

The isolated material completely recrystallized at room temperature to Compound (2):adipic acid co-crystal Form B over 2 months.

Figure 15:
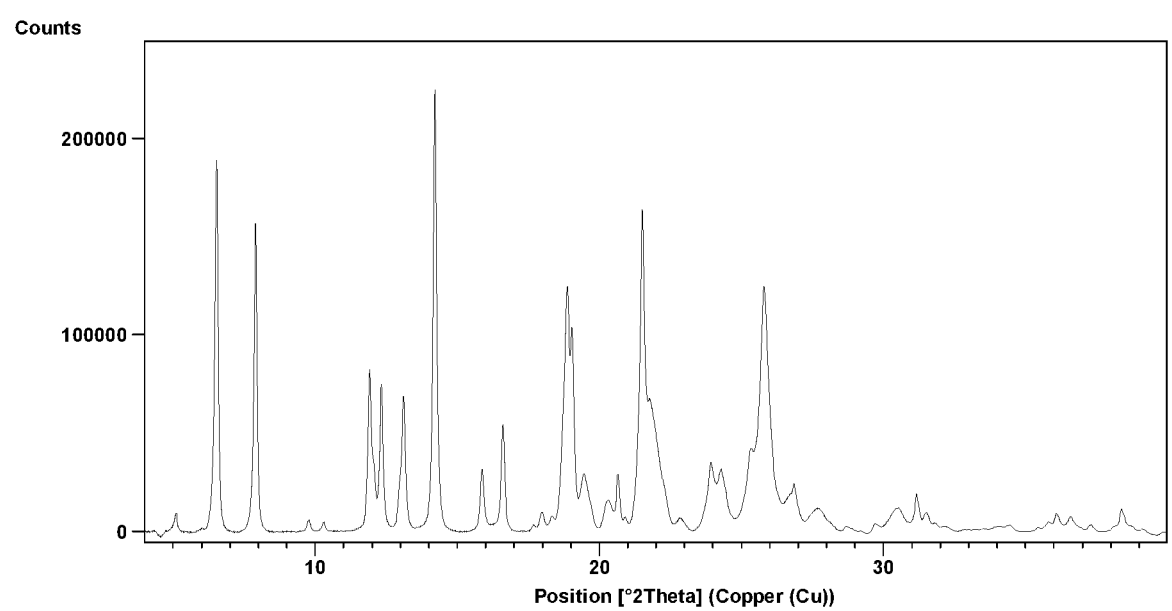
FIG. 15 shows an X-ray powder diffraction pattern of polymorphic Form B of the co-crystal formed between Compound 2 with adipic acid.
Figure 18:
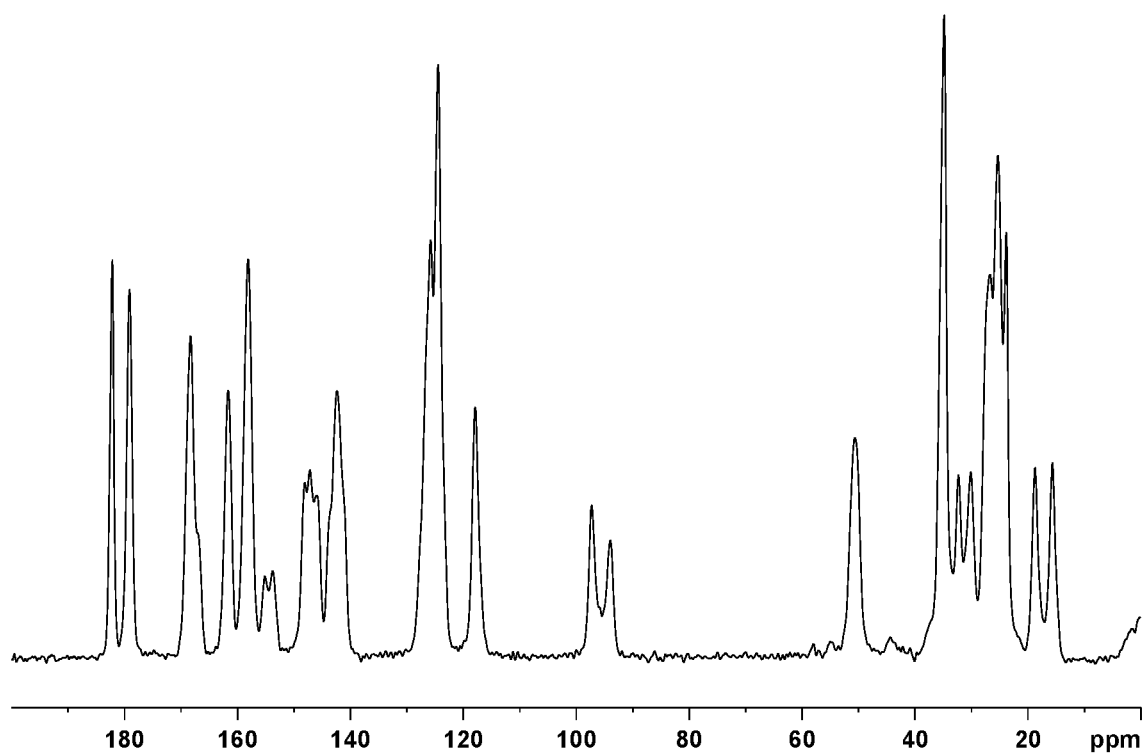
FIG. 18 shows a solid-state NMR spectrum of polymorphic Form B of the co-crystal formed between Compound 2 and adipic acid.

The XRPD pattern and $^{13}$C NMR spectrum of Form B of adipic acid co-crystal of Compound (2) are shown in FIGS. 15 and 18, respectively. Certain peaks observed in the $^{13}$C NMR spectrum are summarized below.

TABLE 12

| Peak | Shift ±0.1 [ppm] | Intensity [% of max] |
| --- | --- | --- |
| 1 | 117.9 | 42.2 |
| 2 | 97.3 | 25.6 |
| 3 | 94.0 | 19.6 |
| 4 | 26.7 | 64.6 |
| 5 | 15.7 | 32.7 |
| 6 | 161.7 | 45.0 |
| 7 | 153.8 | 14.5 |
| 8 | 50.7 | 37.0 |
| 9 | 25.3 | 84.7 |
| 10 | 18.8 | 31.8 |
| 11 | 179.1 | 61.6 |
| 12 | 168.3 | 54.1 |
| 13 | 158.1 | 67.2 |
| 14 | 147.2 | 31.5 |
| 15 | 142.4 | 44.9 |
| 16 | 124.5 | 100.0 |
| 17 | 32.3 | 30.7 |
| 18 | 30.1 | 31.2 |
| 19 | 125.8 | 70.3 |

Example 9: Binary Phase Diagram of Compound (2) Adipic Acid Co-Crystal

FIG. 18 is a depiction of an approximate phase diagram consistent with the measured thermal data $T_{AA}$: Melting temperature of adipic acid, $T_{CoX}$ melting temperature of the Compound (2): adipic acid co-crystal, $T_P$: peritectic temperature, $T_{CMPD2}$: Melting temperature of Compound (2), $T_{E1}$: Eutectic melt temperature, P peritectic point, E1 eutectic point, $S_{AA}$: Solid adipic acid, L liquid, $S_{CoX}$: Solid Compound (2):Adipic Acid co-crystal, $S_{CMPD2}$:Solid Compound (2), $T_{m-E}$: metastable Eutectic melt temperature, m-E: metastable Eutectic point.

The binary phase diagram was explored using differential scanning calorimetry on mixtures of Compound (2) and adipic acid and mixtures of Compound (2):Adipic acid and co-crystal. The stoichiometric composition of the co-crystal in % w:w Compound (2) was calculated from the molar stoichiometry. A representative differential scanning calorimetry thermogram is shown FIG. 11. The thermogram of Compound (2):adipic acid co-crystal shows a melting endotherm at 196° C.±2° C. followed by a recrystallization exotherm which is followed by a broad dissolution endotherm. Melting of Compound (2) is observed at 256° C.±2° C. when the adipic acid is allowed to fully decompose and evaporate. The observed differential scanning calorimetry thermogram depends on the composition i.e., the solid phases that are present in the material and is explained by the binary phase diagram. Furthermore, it depends on other experimental details. A eutectic melt endotherm was observed when excess adipic acid was present in addition to the co-crystal at 138° C.±2° C. The binary phase diagram of Compound (2) and adipic acid is consistent with the observed differential scanning calorimetry curves on compound 1:adipic acid co-crystal and compound 1:adipic acid, adipic acid mixtures; an example is given in FIG. 10.

Figure 19:
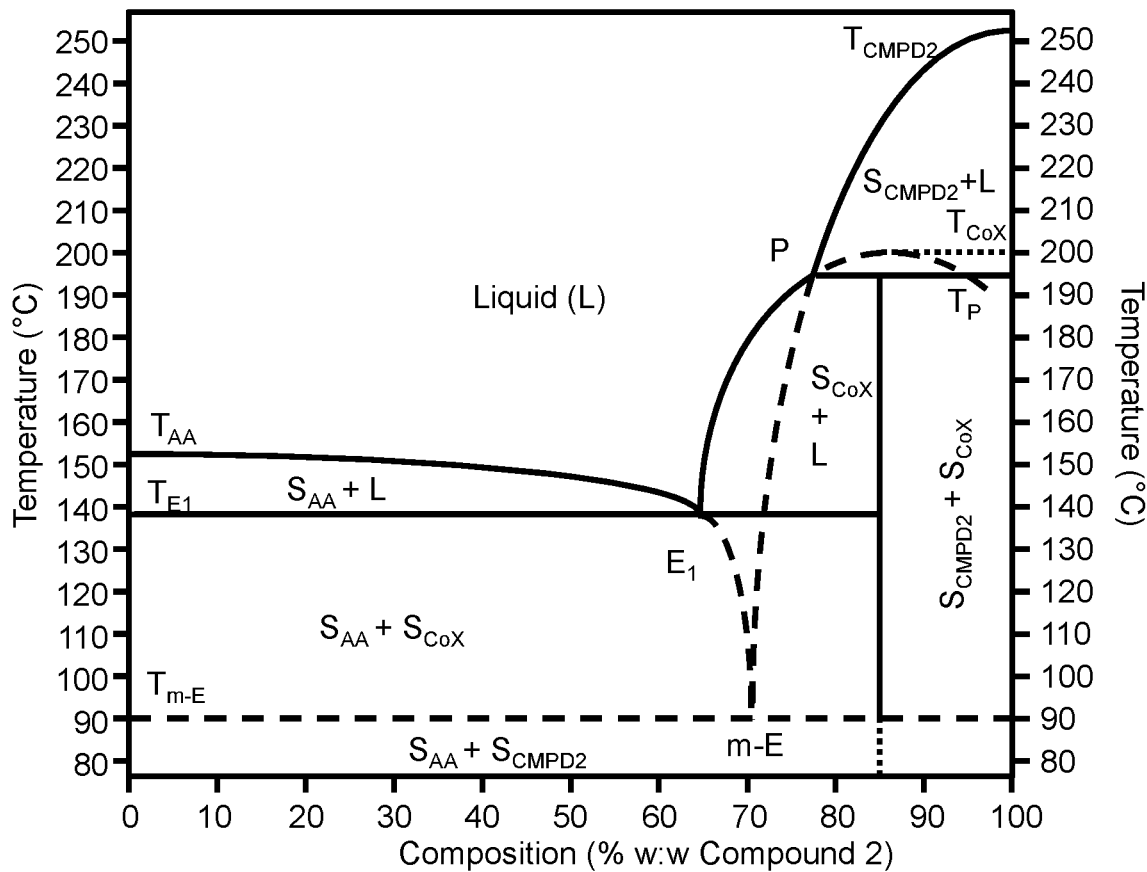
FIG. 19 shows a binary phase diagram of Compound 2 and adipic acid.

Certain measured points of the phase diagram of FIG. 19 are summarized below:

TABLE 13

| Point | Tempereature [° C.] ± 2 | Composition [% w:w] compound 2 |
| --- | --- | --- |
| E1 | $T_{E1}$ = 138 | 65 ± 5 |
| P or E2 | $T_P$ or $T_{E2}$ = 196 | Not known |
| $T_{AA}$ | 153 | 0 |
| $T_{CMPD1}$ | 256 | 100 |

Example 9. Biopharmaceutical Analysis

Figure 20:
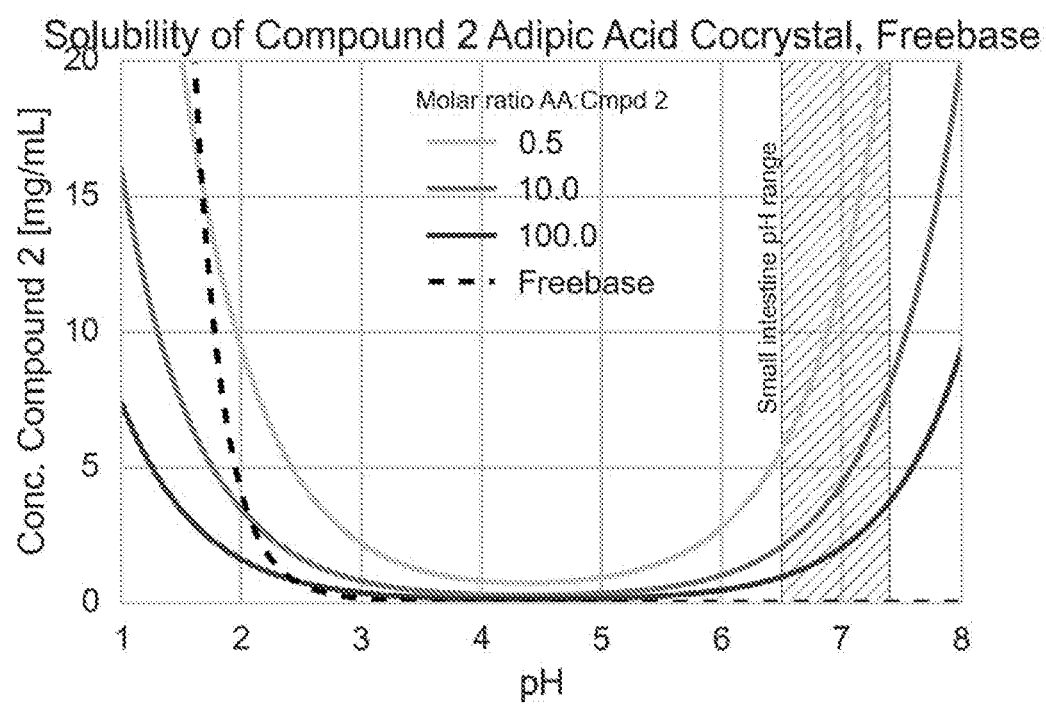
FIG. 20 shows a diagram of the calculated pH solubility of the co-crystal formed between Compound 2 with adipic acid (by excess adipic acid content) and free form Compound 2.

The pH solubility curve for Compound (2), Compound (2): adipic acid co-crystal, and Compound (2): adipic acid co-crystal in the presence of excess adipic acid were calculated from the $pK_a$ values of Compound (2) and adipic acid, Compound (2):adipic acid co-crystal $K_{sp}$ value, the binding constant of Compound (2) and adipic acid in aqueous buffer and the Compound (1) self association constant in aqueous buffer and the solubility of Compound (2) free form. The solubility of the adipic acid cocrystal of Compound (2) was dependent on pH and the concentration of excess adipic acid. In general, as the concentration of adipic acid increased the apparent solubility of the cocrystal decreased. At low pH the solubility of the cocrystal was less than the freebase Compound (2), but within the pH range of the fasted human small intestine the cocrystal was much more soluble than the free form (or free base) Compound (2), as shown in FIG. 20. Simulations of oral dosing showed the adipic acid cocrystal drived nearly complete absorption at doses up to 1.5 g, and at doses exceeding 800 mg the negative impact of adipic acid on cocrystal solubility decreased exposure slightly (data not shown).

Example 10. Dissolution Analysis

Figure 21:
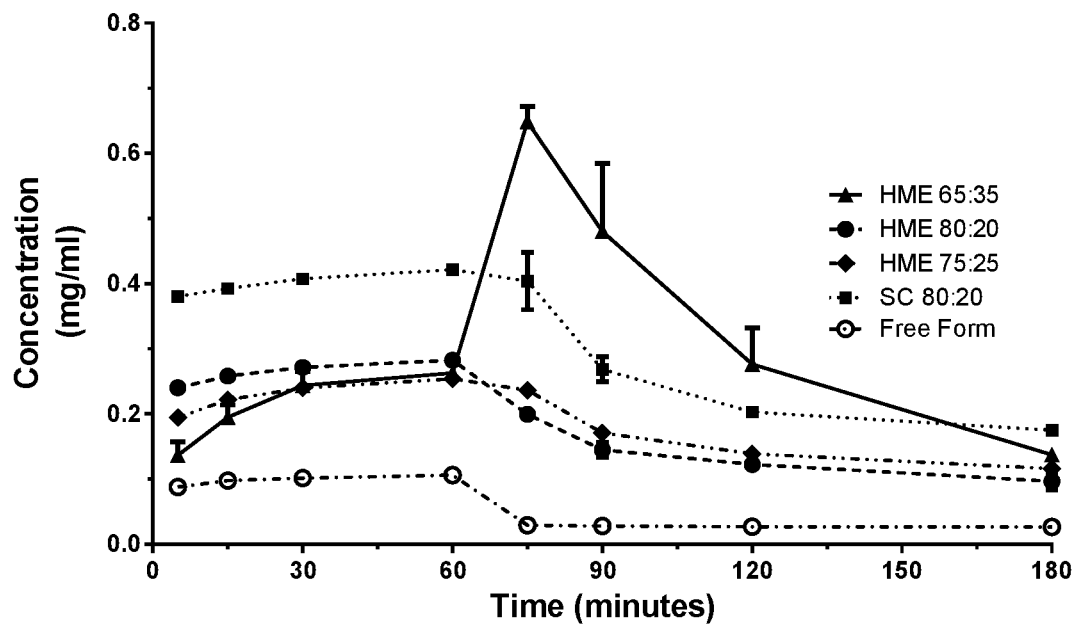
FIG. 21 shows two stage dissolution profiles for: i) Compound 1:adipic acid co-crystal prepared by hot melt extrusion and slurry crystallization; ii) HME 65:35: Compound 1:adipic acid co-crystal manufactured using hot melt extrusion with 65% w:w Compound 1 and 35% w:w adipic acid; iii) HME 75:25: Compound 1:adipic acid co-crystal manufactured using hot melt extrusion with 75% w:w Compound 1 and 25% w:w adipic acid; iv) HME 80:20: Compound 1:adipic acid co-crystal manufactured using hot melt extrusion with 80% w:w Compound 1 and 20% w:w adipic acid; v) SC 80:20: slurry crystallized Compound 2:adipic acid co-crystal with final Compound 2 content of 79% w:w Compound 2 and 21% w:w adipic acid; and vi) Free Form: Compound 2 free form.

In-vitro two stage dissolution experiments using simulated intestinal and gastric fluids were used to evaluate and predict Compounds (1) and (2) and their co-crystals with adipic acid in-vivo performance. Most commonly drug absorption can occur in the upper intestine and high solubility generally indicates high in-vivo bioavailability after simulated intestinal fluid is added in two stage dissolution experiments for drugs with solubility limited bioavailability. FIG. 21 shows two stage dissolution profiles for: i) Compound 1:adipic acid co-crystal prepared by hot melt extrusion and slurry crystallization; ii) HME 65:35: Compound 1:adipic acid co-crystal manufactured using hot melt extrusion with 65% w:w Compound 1 and 35% w:w adipic acid; iii) HME 75:25: Compound 1:adipic acid co-crystal manufactured using hot melt extrusion with 75% w:w Compound 1 and 25% w:w adipic acid; iv) HME 80:20: Compound 1:adipic acid co-crystal manufactured using hot melt extrusion with 80% w:w Compound 1 and 20% w:w adipic acid; v) SC 80:20: slurry crystallized Compound 2:adipic acid co-crystal with final Compound 2 content of 79% w:w Compound 2 and 21% w:w adipic acid; and vi) Free Form: Compound 2 free form. As shown in FIG. 21, the two stage dissolution data on Compound 1:adipic acid co-crystal and Compound 2:adipic acid co-crystal showed higher Compound 1 and Compound 2 concentrations than Compound 1 or Compound 2 free form, respectively. Also, the concentration of Compound 1 for Compound 1:adipic acid co-crystal prepared by hot melt extrusion from Compound 1 and adipic acid at 65% w:w and 35% w:w performed better than slurry crystallized Compound 2:adipic acid co-crystal or Compound 1:adipic acid co-crystal prepared by hot melt extrusion from Compound 1 and adipic acid at 75% w:w and 25% w:w and Compound 1:adipic acid co-crystal prepared by hot melt extrusion from Compound c and adipic acid at 80% w:w and 20% w:w, respectively. Without being bound to a particular theory, this is potentially due to the microstructure that was obtained for the eutectic solid.

Two stage dissolution experiments were performed at least in duplicate. Fasted state simulated gastric fluid (FaSSGF) was equilibrated for 30 minutes under stirring to 37° C. in a 100 ml clear class vial using a water bath consisting of a temperature controlled jacketed vessel. The compound 1:adipic acid co-crystal and compound 2:adipic acid co-crystal was added and the suspension was stirred at about 130 rpm and 37° C., respectively. Aliquots (0.5 ml) were taken at 5, 15, 30, and 60 minutes. Solids were separated by filter centrifugation using centrifuge filter units with a 0.45 μm membrane and spinning at 5000 rpm for 5 minutes on an Eppendorff Model 5418 centrifuge. The pH of the dissolution samples was measured after sampling at 15 and 60 minute time points. The supernatants of the filtered samples were 10 fold diluted of with diluent for HPLC Analysis. At the 65 minute timepoint fasted state simulated intestinal fluid FaSSIF equilibrated at 37° C. was added to the suspension and the suspension was continued to stir at 130 rpm. Aliquots (0.5 ml) were taken at 75, 90, 120 and 180 minute timepoints. Solids were separated by filter centrifugation using centrifuge filter units with a 0.45 μm membrane and spinning at 5000 rpm for 5 minutes on an Eppendorff Model 5418 centrifuge. The pH of the dissolution samples was measured after sampling at 75, 90 and 180 minute time points. The supernatants of the filtered samples were 10 fold diluted of with diluent for HPLC Analysis. The amounts of material and simulated fluids used are summarized below:

| Material | Weight [mg] | Volume FaSSGF | Volume FaSSIF |
| --- | --- | --- | --- |
| HME 65:35 | 43.5, 44.5 | 10 | 16 |
| HME 75:25 | 40.8, 40.3 | 10 | 16 |
| HME 80:20 | 38.3, 38.1 | 10 | 16 |
| SC 80:20 | 31.7, 32.0, 31.6 | 8 | 12 |
| Free Form | 24.7, 25.1, 26.6 | 8 | 12 |

The concentrations of Compounds 1 and 2 were measured using following HPLC method, respectively:

| | |
| --- | --- |
| Column | "Xterra Phenyl 4.6 × 50 mm, 5.0 um" |
| Column Temperature | 30° C. |
| Flow Rate | 1.5 ml/min |
| Injector Volume | 10 ul |
| Auto-sampler Temperature | 25 C. |
| Total Run Time | 3.0 mins |
| Detector Wavelength | 240 nm |
| Needle Wash Solution | Methanol |
| Sampling Rate | 1 per sample |
| Data Acquisition Time | 3 |
| Mobile Phase A | 0.1% TFA in Water |
| Mobile Phase B | 0.1% TFA in Acetonitrile |
| Gradient | 85% Mobile Phase A 15% Mobile Phase B |

Typical simulated fluid preparations were used for 2 stage dissolution experiments: FaSSIF was prepared by adding about 1.80 g of Sodium Hydroxide Pellets, 2.45 g of Maleic Anhydride, 6.37 g of Sodium Chloride, 1.61 g of Sodium Taurocholate and 618.8 mg of Lecithin to 800 ml water. The solution was stirred until all materials were completely dissolved. Then the pH was adjusted to 6.5 using 1.0N HCl and 50% NaOH Solution while the solution was being stirred. Water was added to a final volume of 1 l. FaSSGF was prepared by adding 50.0 mL of 1.0N HCl, about 1.0 g of "800-2500 U/mg" pepsin, 43 mg of Sodium Taurocholate, 2.0 g of Sodium Chloride (NaCl) to 800 ml water. Water was added to a final volume of 1 l. The final pH was typically 1-2.

Example 12. Bioavailability of the Co-Crystals of the Invention

Figure 22:
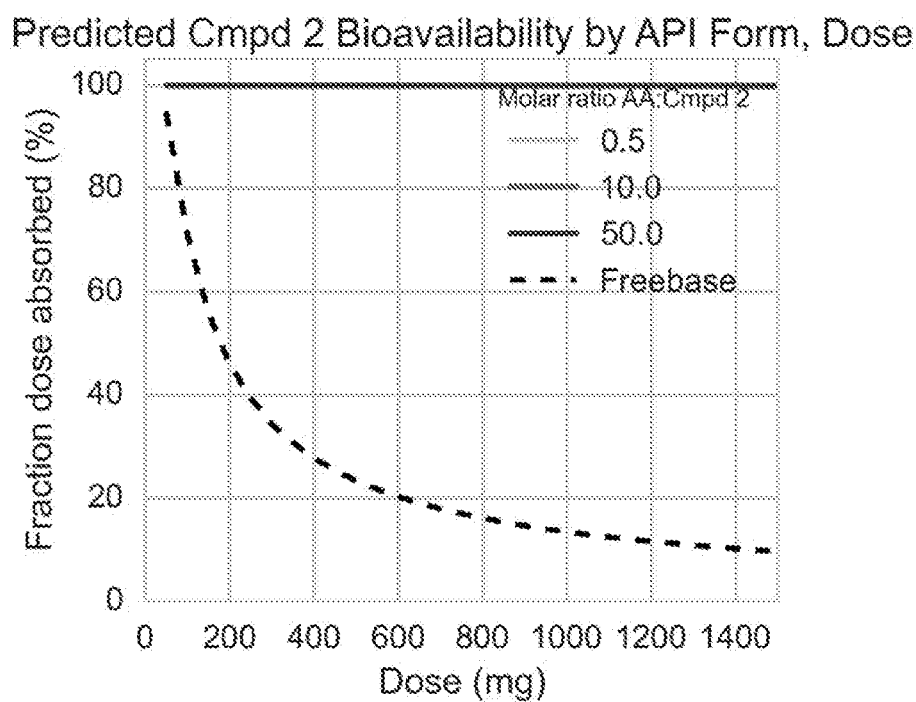
FIG. 22 shows a predicted fraction absorbed for the co-crystal formed between Compound 2 and adipic acid, and Compound 2 free form.

The oral bioavailability of Compound 2:adipic acid co-crystal and Compound 2 free form in humans was predicted based on the calculated pH solubility curves in FIG. 20 using GastroPlus, version 8.5.0002 Simulations Plus, Inc. A jejunum permeability of 1.67e-4 cm/s and particle radius of 10 microns was used. All other parameters were the default settings of the software. The simulations predict 100% fraction absorbed for oral doses up to 1500 mg Compound 2:adipic acid co-crystal and Compound 2; adipic acid co-crystal with additional adipic acid present whereas the predicted Compound 2 oral fraction absorbed steeply decreases with increasing doses. As shown in FIG. 22, the simulations indicate that the compound 2:adipic acid co-crystal has superior oral bioavailability when compared to Compound 2 free form to give sufficient exposure for human safety studies for doses up to but not limited to 1500 mg and can result in larger safety margins for Compound 2. Furthermore, high oral bioavailability will reduce the oral dose that is needed to reach efficacious blood levels. Similar results are expected for Compound 1 based on the similarity in the observed physical properties of Compound 1 and Compound 2.

Example 13. Biological Efficacy of Compound 2/Adipic Acid Co-Crystal

Example A. DNA-PK Kinase Inhibition Assay

The adipic acid co-crystal of Compound 2 was screened for its ability to inhibit DNA-PK kinase using a standard radiometric assay. Briefly, in this kinase assay the transfer of the terminal $^{33}$P-phosphate in $^{33}$P-ATP to a peptide substrate is interrogated. The assay was carried out in 384-well plates to a final volume of 50 μL per well containing approximately 6 nM DNA-PK, 50 mM HEPES (pH 7.5), 10 mM MgCl$_2$, 25 mM NaCl, 0.01% BSA, 1 mM DTT, 10 μg/mL sheared double-stranded DNA (obtained from Sigma), 0.8 mg/mL DNA-PK peptide (Glu-Pro-Pro-Leu-Ser-Gln-Glu-Ala-Phe-Ala-Asp-Leu-Trp-Lys-Lys-Lys, obtained from American Peptide), and 100 μM ATP. Accordingly, compounds of the invention were dissolved in DMSO to make 10 mM initial stock solutions. Serial dilutions in DMSO were then made to obtain the final solutions for the assay. A 0.75 μL aliquot of DMSO or inhibitor in DMSO was added to each well, followed by the addition of ATP substrate solution containing $^{33}$P-ATP (obtained from Perkin Elmer). The reaction was started by the addition of DNA-PK, peptide and ds-DNA. After 45 min, the reaction was quenched with 25 μL of 5% phosphoric acid. The reaction mixture was transferred to MultiScreen HTS 384-well PH plates (obtained from Millipore), allowed to bind for one hour, and washed three times with 1% phosphoric acid. Following the addition of 50 μL of Ultima Gold™ high efficiency scintillant (obtained from Perkin Elmer), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition. The adipic acid co-crystal of Compound (2) had a Ki of about 2 nM.

Example B: Efficacy of Compounds (1) and (2) in Combination with Whole Body IR The in vivo efficacies of Compounds (1) and (2) in combination with whole body IR were examined in the OD26749 primary NSCLC (non-small cell lung cancer) and the OE-19 GEJ cell line xenograft models. The results are summarized in Tables 14 and 15. In these studies, Compounds (1) and (2) were formulated with 16% captisol/1% PVP/1% HPMC E5 pH2.

B.1. Efficacy of Compound (1) in Combination with IR in the OD26749 NSCLC Xenograft Model The in vivo efficacy of Compound (1) was evaluated in the primary OD26749 NSCLC subcutaneous xenograft model. Compound (1) administered at 100 mg/kg tid on a single day significantly enhanced the radiation effect of a single 2 Gy dose of whole body IR in this model (% T/C 26 for the combination compared to % T/C of 80 for radiation alone, P<0.001). Efficacy was evaluated using a regimen in which 2-Gy whole body IR was administered twice, one week apart. Compound (1) was administered PO (tid at 0, 3, and 7 h) at 100 mg/kg alone or with a single 2 Gy dose of whole body IR at 3.25 h. Seven days later, the same regimens were repeated. Compound (1) in combination with 2 Gy whole body IR induced significant tumor regression (% T/Ti of −75; P<0.01) compared to IR alone.

Compound (1) alone and IR alone did not induce significant (P>0.05) tumor growth inhibition compared to vehicle controls (% T/C of 74 and 64, respectively). In this primary tumor model, both groups exhibited some degree of body weight loss (6.7% and 8.7% maximal loss on Day 2 or Day 9 for the IR alone and combination group, respectively) that recovered over the course of the study. The addition of a second administration of 2 Gy IR in combination with Compound (1) resulted in a significant increase in time to tumor doubling (TTD) with a 33.4 day TTD in the combination group compared to only 2 to 3 days for the vehicle, IR and Compound (1) single agent groups.

B.2. Bridging Study: Compounds (1) and (2) in Combination with Two Cycles of Whole Body IR in a Primary NSCLC Xenograft Model (OD26749) in Nude Mice The efficacies of Compounds (1) and (2) in combination with whole body IR (2 Gy) were evaluated in the OD26749 primary NSCLC xenograft model at a Compound (1) dose level of 100 mg/kg PO bid (0 and 4 h) and Compound (2) dose levels of 50 mg/kg and 100 mg/kg PO bid (0 and 4 h). Two cycles of whole body IR (2 Gy) were given 15 min after the first compound administration (0.25 hour). Control animals were administered vehicle PO bid (0 and 4 h). Two cycles of treatment were performed on Day 0 and Day 7.

Two cycles of whole body radiation (2 Gy) alone did not inhibit tumor growth compared to vehicle treated tumors (% T/C=106). However, efficacy was significantly enhanced when Compounds (1) and (2) were combined with IR, as average tumor volumes in all combination groups were significantly smaller than those in the IR only group (P<0.001). In addition, the Compounds (1) and (2) (100 mg/kg bid) combination groups demonstrated very similar anti-tumor activity (% T/C=4.80 and 7.80 respectively), blood exposure (AUC 65.8 and 58.2 µg*h/mL), and tolerability (maximum body weight change −2.40% and 2.70%). In addition, the average tumor volume in the 50-mg/kg combination group was statistically different than those in the Compounds (1) and (2) 100 mg/kg combination groups (P<0.001).

B.3. Efficacy of Compounds (1) and (2) in Combination with IR in the OE-19 Gastro-Esophageal Junction (GEJ) Cancer Xenograft Model The OE-19 cell line xenograft model was used to evaluate the efficacy of Compounds (1) and (2) alone and in combination with IR. Two cycles of treatment were administered (Day 0 and Day 7) as performed in the OD26749 model above. Two cycles of whole body IR (2 Gy) alone exhibited minimal effect on tumor growth compared to vehicle control (% T/C=60.0) indicating that this tumor model is relatively resistant to IR. In contrast, the combination of Compound (2) and 2 Gy whole body IR resulted in significant tumor growth inhibition compared to the vehicle control with a % T/C of 8.00 (P<0.001). The combination group also showed significant tumor growth inhibition compared to the IR only group (P<0.001). Compound (1) in combination with 2 Gy whole body IR also significantly inhibited tumor growth in this model.

B.4. Efficacy of Compounds (1) and (2) in a Primary NSCLC Xenograft Model

The in vivo efficacies of Compounds (1) and (2) were evaluated alone and in combination with three consecutive days of focused IR in the primary LU-01-0030 NSCLC subcutaneous xenograft model. The dose-dependent anti-tumor activity of Compound (2) alone and in combination with focused beam IR was evaluated in the LU-01-0030 model. In this model, IR treatment alone resulted in significant tumor regression; however tumor re-growth was observed approximately 20 days after the last day of treatment. On Day 34, Compound (2) combination groups demonstrated statistically significant (P<0.001) anti-tumor activity when compared to the vehicle and IR only groups, with % T/Ti values of −96.3, −67.1, −96.9, and 1.6% for the 50 and 25 mg/kg bid and 50 and 25 mg/kg qd groups, respectively. Mice in the combination treatment groups were monitored (without treatment) for up to 90 days as some mice had no evidence of tumor burden. In all experimental groups, treatments were generally well tolerated as evidenced by maximum body weight losses ranging from −1.11% to −6.93% 1 to 9 days after treatment initiation B.5. Efficacy of Compounds (1) and (2) in Combination with IR in a Primary GEJ Cancer Xenograft Model The in vivo activities of Compounds (1) and (2) were compared in combination with focused beam IR in a primary gastric cancer subcutaneous xenograft model. In the ST 02 0004 model, focused IR was administered on three consecutive days alone and in combination with Compound (1) or Compound (2). IR treatment alone resulted in a slight delay in tumor growth of approximately 7 days after the last day of treatment. Compounds (1) and (2) combination groups demonstrated statistically significant (P<0.001) anti tumor activity when compared to the vehicle and IR only groups with a % T/Ti value of −2.8% for the 100 mg/kg Compound (1) combination group and % T/C values of 9.2 and 17.4 for the 100 and 25 mg/kg Compound (2) combination groups, respectively. For all experimental groups, treatment was generally well tolerated as evidenced by maximum body weight losses ranging from −8.06% to −10.0% 10 to 48 days after treatment initiation The anti-tumor activity of Compound (2) in combination with focused-beam IR and the standard of care agents, paclitaxel and carboplatin, was also evaluated in the ST 02 0004 model. Treatment with paclitaxel, carboplatin, and IR was administered once per week for three weeks alone or in combination with Compound (2). Paclitaxel/carboplatin treatment did not impact tumor growth nor did the combination of paclitaxel/carboplatin and 50 mg/kg Compound (2). However, on Day 45, 25 and 50 mg/kg Compound (2) in combination with paclitaxel/carboplatin and IR demonstrated a statistically significant difference (P<0.001) in anti-tumor activity when compared to the vehicle group with % T/C values of 2.5 and 11.1 for the 50 and 25 mg/kg Compound (2), paclitaxel/carboplatin, IR combination groups, respectively. Further, the 50 and 25 mg/kg Compound (2), paclitaxel/carboplatin, IR combination groups were statistically different (P<0.05) from the paclitaxel/carboplatin, paclitaxel/carboplatin/50 mg/kg Compound (2), and paclitaxel/carboplatin/IR groups. Compound (2) blood exposures were 9.3 and 27 μg*h/mL for the 25 and 50 mg/kg Compound (2) bid groups, respectively.

In Tables 14 and 15, for example, PO bid (0, 4 h) indicates Compound (2) is administered twice (bid) at time point 0 and then 4 hours after; IR (0.25 h) qdx3 indicates radiation is administered 15 minutes (0.25 h) after the administration of Compound (2) (0 h), and once a day for 3 days (qdx3); q7dx2 indicates once a week for two weeks; qod indicates every other day twice (e.g., Day 1 and Day 3); and paclitaxel q7d x3 (−0.25 h), carboplatin q7dx3 (−0.25 h) indicates administration of paclitaxel and carboplatin 15 minutes prior to the administration of Compound (2), followed by additional administration of Compound (2) after 4 hours after the first administration of Compound (2). In one specific example, "5 mg/kg paclitaxel q7dx3 (−0.25 h), 25 mg/kg carboplatin q7dx3 (−0.25 h), 2 Gy IR qdx3 (0.25 h), PO 50 mg/kg bid (0, 4 h) qdx3" indicates that 5 mg/kg of paclitaxel and 25 mg/kg of carboplatin are administered 15 minutes prior to the first administration of Compound (2); the first administration of Compound (2) is given; radiation is administered 15 minutes after the first administration of Compound (2); and then the second administration of Compound (2) is provided 4 hours after the first administration of Compound (2).

TABLE 14

Summary of In Vivo Efficacy Studies with Compound (1)

| Tumor Model, DNA Damaging Agent | Study Groups | Results | | |
|---|---|---|---|---|
| | | % T/C (Day 20) | % T/Ti (Day 20) | Max. body wt loss (%) |
| OD26749 (Primary NSCLC) Whole Body IR | 2 Gy Radiation qd × 1 | 80 | — | −6.90 (Day 2) |
| | PO 100 mg/kg tid (0, 3, 7 h) qd × 1 | 101 | — | −2.40 (Day 2) |
| | PO 100 mg/kg tid (0, 3, 7 h) qd × 1, 2 Gy qd × 1 (3.25 h) | 26.0 | — | −9.70 (Day 2) |
| | | % T/C (Day 16) | % T/Ti (Day 16) | Max. body wt loss (%) |
| OD26749 (Primary NSCLC) Whole Body IR | 2 Gy Radiation q7d × 2 | 64 | — | −6.7 (Day 2) |
| | PO 100 mg/kg tid (0, 3, 7 h) q7d × 2 | 74 | — | weight gain |
| | PO 100 mg/kg tid (0, 3, 7 h) q7d × 2, 2 Gy q7d × 2 (3.25 h) | — | −75 | −8.7 (Day 9) |
| | | % T/C (Day 22) | % T/Ti (Day 22) | Max. body wt loss (%) |
| OD26749 (Primary NSCLC bridging study)* Whole Body IR | 2 Gy Radiation qd × 3 | 106 | — | −0.90 (Day 1) |
| | PO 100 mg/kg bid (0, 4 h), 2 Gy (0.25 h) qd × 3 | 4.8 | — | −2.40 (Day 1) |
| | | % T/C (Day 29) | % T/Ti (Day 29) | Max. body wt loss (%) |
| OD26749 (Primary NSCLC) Whole Body IR | 2 Gy Radiation q7d × 2 | 42 | — | −3.50 (Day 1) |
| | PO 200 mg/kg qd, 2 Gy IR (0.25 h) q7d × 2 | 6.5 | — | −6.10 (Day 1) |
| | PO 100 mg/kg bid (0, 4 h), 2 Gy IR (0.25 h) q7d × 2 | — | −3.1 | −3.70 (Day 8) |
| | PO 50 mg/kg bid (0, 4 h), 2 Gy IR (0.25 h) q7d × 2 | 11.7 | — | −5.50 (Day 8) |
| | PO 25 mg/kg bid (0, 4 h), 2 Gy IR (0.25 h) q7d × 2 | 25.6 | — | −7.70 (Day 8) |
| | | % T/C (Day 30) | % T/Ti (Day 30) | Max. body wt loss (%) |
| LU-01-0030 (Primary NSCLC) | 2 Gy Radiation qd × 3 | 14.8 | — | −4.0 (Day 4) |
| | PO 100 mg/kg tid (0, 3, 7 h) qd × 5 | 79.1 | — | −0.63 (Day 6) |
| | PO 100 mg/kg tid (0, 3, 7 h) qd × 3, 2 Gy IR (0.25 h) qd × 3 | — | −90.6 | −1.58 (Day 4) |

TABLE 14-continued

Summary of In Vivo Efficacy Studies with Compound (1)

| Tumor Model, DNA Damaging Agent | Study Groups | | Results | |
|---|---|---|---|---|
| Focused IR | PO 100 mg/kg tid (0, 3, 7 h) qd × 5, 2 Gy IR (0.25 h) qd × 3 | — | −91.6 | −1.68 (Day 4) |
| | PO 100 mg/kg bid (0, 4 h) qd × 3, 2 Gy IR (0.25 h) qd × 3 | — | −85.6 | −1.42 (Day 4) |

| | | % T/C (Day 27) | % T/Ti (Day 27) | Max. body wt loss (%) |
|---|---|---|---|---|
| LU-01-0030 (Primary NSCLC) Focused IR | 2 Gy Radiation qd × 3 | 16.1 | — | −7.44 (Day 3) |
| | PO 100 mg/kg qd × 3, 2 Gy (0.25 h) IR qd × 3 | — | −76.5 | −3.68 (Day 2) |
| | PO 100 mg/kg bid (0, 4 h) qd × 3, 2 Gy (0.25 h) IR qd × 3 | — | −90.1 | −2.87 (Day 3) |
| | PO 50 mg/kg bid (0, 4 h) qd × 3, 2 Gy (0.25 h) IR qd × 3 | — | −87.8 | −5.70 (Day 3) |
| | PO 25 mg/kg bid (0, 4 h) qd × 3, 2 Gy (0.25 h) IR qd × 3 | — | −80.3 | −5.81 (Day 2) |

| | | % T/C (Day 27) | % T/Ti (Day 27) | Max. body wt loss (%) |
|---|---|---|---|---|
| LU-01-0030 (Primary NSCLC) Focused IR | 2 Gy Radiation qd × 3 | 16.1 | — | −7.44 (Day 3) |
| | PO 50 mg/kg bid (0, 4 h) qd × 3, 2 Gy (0.25 h) IR qd × 3 | — | −76.5 | −3.68 (Day 2) |
| | PO 50 mg/kg bid (0, 4 h) qd × 2, 2 Gy (0.25 h) IR qd × 3 | — | −90.1 | −2.87 (Day 3) |
| | PO 25 mg/kg bid (0, 4 h) qd × 3, 2 Gy (0.25 h) IR qd × 3 | — | −87.8 | −5.70 (Day 3) |
| | PO 10 mg/kg bid (0, 4 h) qd × 3, 2 Gy (0.25 h) IR qd × 3 | — | −80.3 | −5.81 (Day 2) |

| | | % T/C (Day 31) | % T/Ti (Day 31) | Max. body wt loss (%) |
|---|---|---|---|---|
| LU-01-0030 (Primary NSCLC) Focused IR | 2 Gy Radiation qd × 3 | 49.3 | — | −4.46 (Day 2) |
| | PO 10 mg.kg bid (0, 4 h) qd × 3, 2 Gy IR (0.25 h) | — | −5.3 | −3.33 (Day 3) |
| | PO 50 mg/kg qd × 3, 2 Gy IR (0.25 h) | 4.5 | — | −2.07 (Day 1) |
| | PO 50 mg/kg bid (0, 4 h) qd × 1, 2 Gy IR (0.25 h) | 7.2 | — | −0.59 (Day 1) |
| | PO 50 mg/kg bid (0, 4 h) qd × 2, 2 Gy IR (0.25 h) | — | −1.7 | −2.11 (Day 1) |
| | PO 50 mg/kg bid (0, 4 h) qd × 3, 2 Gy IR (0.25 h) | — | −14.1 | −0.94 (Day 3) |

| | | % T/C (Day 24) | % T/Ti (Day 24) | Max. body wt loss (%) |
|---|---|---|---|---|
| LU-01-0030 (Primary NSCLC) Focused IR | 2 Gy Radiation qd × 3 | 26.7 | — | −0.40 (Day 2) |
| | PO 10 mg/kg bid (0, 4 h) qd × 3, 2 Gy IR qd × 3 (0.25 h) | — | −29.8 | −1.46 (Day 4) |
| | PO 25 mg/kg bid (0, 4 h) qd × 3, 2 Gy IR qd × 3 (0.25 h) | — | −75.2 | −2.03 (Day 4) |
| | PO 50 mg/kg bid (0, 4 h) qd × 3, 2 Gy IR qd × 3 (0.25 h) | — | −87.6 | −1.19 (Day 4) |
| | PO 50 mg/kg bid (0, 4 h) qod × 2, 2 Gy IR qd × 3 (0.25 h) | — | −79.9 | −1.59 (Day 4) |

| | | % T/C (Day 18) | % T/Ti (Day 18) | Max. body weight loss (%) |
|---|---|---|---|---|
| OE-19 (GEJ cell line) Whole Body IR | 2 Gy Radiation qd7 × 2 | 86.0 | — | −1.9 (Day 1) |
| | PO 100 mg/kg bid (0, 4 h) qd7 × 2 | 79.0 | — | −1.70 (Day 8) |
| | PO 100 mg/kg bid (0, 4 h) qd7 × 2, 2 Gy IR qd7 × 2 (0.25 h) | 24.0 | — | −3.50 (Day 1) |

TABLE 14-continued

Summary of In Vivo Efficacy Studies with Compound (1)

| Tumor Model, DNA Damaging Agent | Study Groups | Results | | |
|---|---|---|---|---|
| | | % T/C (Day 34) | % T/Ti (Day 34) | Max. body weight loss (%) |
| ST-02-0004 (Primary GEJ tumor - bridging study)* Focused IR | 2 Gy Radiation qd × 3 | 59.6 | — | −8.06 (Day 48) |
| | PO 100 mg/kg qd × 3 | 95.6 | — | −6.31 (Day 14) |
| | PO 100 mg/kg bid (0, 4 h) qd × 3, 2 Gy IR (0.25 h) | — | −2.8 | −10.0 (Day 10) |

TABLE 15

Summary of In Vivo Efficacy Studies with Compound (2)

| Tumor Model, DNA Damaging Agent | Study Groups | Results | | |
|---|---|---|---|---|
| | | % T/C (Day 22) | % T/Ti (Day 22) | Max. body wt loss (%) |
| OD26749 (Primary NSCLC-- bridging study) | 2 Gy Radiation qdx3 | 106 | — | −0.90 (Day 1) |
| | PO 100 mg/kg bid (0, 4 h), 2 Gy (0.25 h) qdx3 | 7.8 | — | −2.70 (Day 1) |
| | PO 50 mg/kg bid (0, 4 h), 2 Gy (0.25 h) qdx3 | 27.2 | — | −2.10 (Day 1) |
| | | % T/C (Day 34) | % T/Ti (Day 34) | Max. body wt loss (%) |
| LU-01-0030 (Primary NSCLC) | 2 Gy Radiation qdx3 | 16.9 | — | −4.93 (Day 3) |
| | PO 50 mg/kg bid (0, 4 h) qdx3 | 98.3 | — | −1.11 (Day 9) |
| | PO 50 mg/kg bid (0, 4 h) qdx3, 2 Gy IR (0.25 h) qdx3 | — | −96.3 | −6.93 (Day 3) |
| | PO 25 mg/kg bid (0, 4 h) qdx3, 2 Gy IR (0.25 h) qdx3 | — | −67.1 | −6.59 (Day 3) |
| | PO 50 mg/kg qdx3, 2 Gy IR (0.25 h) qdx3 | — | −96.9 | −4.66 (Day 3) |
| | PO 25 mg/kg qdx3, 2 Gy IR (0.25 h) qdx3 | — | −1.6 | −4.62 (Day 1) |
| | | % T/C (Day 21) | % T/Ti (Day 21) | Max. body wt loss (%) |
| OE-19 (GEJ cell line-- bridging study) | 2 Gy Radiation q7dx2 | 60.0 | — | −0.80 (Day 1) |
| | PO 100 mg/kg bid (0, 4 h) q7dx2, 2 Gy IR q7dx2 (0.25 h) | 8.0 | — | −6.50 (Day 7) |
| | | % T/C (Day 34) | % T/Ti (Day 34) | Max. body wt loss (%) |
| ST-02-0004 (Primary GEJ tumor) | 2 Gy Radiation qdx3 | 56.9 | — | −8.06 (Day 48) |
| | PO 100 mg/kg bid (0, 4 h) qdx3 | 67.6 | — | −7.61 (Day 34) |
| | PO 100 mg/kg bid (0, 4 h) qdx3, 2 Gy IR qdx3 (0.25 h) | 9.2 | — | −9.15 (Day 14) |
| | PO 25 mg/kg bid (0, 4 h) qdx3, 2 Gy IR qdx3 (0.25 h) | 17.4 | — | −6.73 (Day 48) |
| | | % T/C (Day 45) | % T/Ti (Day 45) | Max. body wt loss (%) |
| ST-02-0004 (Primary GEJ tumor- with SOC) | 5 mg/kg paclitaxel q7dx3 (0 h), 25 mg/kg carboplatin q7dx3 (0 h) | 98.0 | — | −8.93 (Day 45) |
| | 5 mg/kg paclitaxel q7dx3 (−0.25 h), 25 mg/kg carboplatin q7dx3 (−0.25 h), PO 50 mg/kg bid (0, 4 h) qdx3 | 95.4 | — | −10.1 (Day 45) |
| | 5 mg/kg paclitaxel q7dx3, 25 mg/kg (−0.25 h), carboplatin q7dx3 (−0.25 h), 2 Gy IR qdx3 (0 h) | 34.9 | — | −10.0 (Day 3) |

TABLE 15-continued

Summary of In Vivo Efficacy Studies with Compound (2)

| Tumor Model, DNA Damaging Agent | Study Groups | | Results | |
|---|---|---|---|---|
| | 5 mg/kg paclitaxel q7dx3 (−0.25 h), 25 mg/kg carboplatin q7dx3 (−0.25 h), 2 Gy IR qdx3 (0.25 h), PO 50 mg/kg bid (0, 4 h) qdx3 | 2.5 | — | −9.20 (Day 10) |
| | 5 mg/kg paclitaxel q7dx3 (−0.25 h), 25 mg/kg carboplatin q7dx3 (−0.25 h), 2 Gy IR qdx3 (0.25 h), PO 25 mg/kg bid (0, 4 h) qdx3 | 11.1 | — | −8.21 (Day 3) |

Example 11. The Combination of Compound (1) or Compound (2) with Standard of Care Drugs or Radiation in Cancer Cell Lines The cell-based experiments and assays were performed with either molecule but not always with both. Compounds (1) and (2) were generally very similar in those assays and experiments. Analysis of the combination experiments was performed using two methods: the Bliss Additivity model and the Mixtures Blend method to determine the degree of synergy, additivity, or antagonism. In the Bliss method, a matrix of Bliss scores was generated for each cell line and treatment, and a sum of the Bliss values over the range of combination concentrations tested was calculated. The average Bliss score (sum of Bliss divided by the number of total data points) was then used to categorize the cell line and treatment as follows: greater than 10 indicates strong synergy, greater than 5 indicates synergy, between 5 and −5 indicates additivity, less than −5 indicates antagonism, and less than −10 indicates strong antagonism. Larger average Bliss values indicate greater confidence in reporting synergy, and smaller scores indicate greater confidence in reporting antagonism. In the Mixtures Blend method combinants were added in a range of optimal ratios using design of experiment (DOE) software (DX-8 from STAT-EASE); the cells were irradiated with 2 Gy as required. Synergy was determined using statistical analysis of the data (ANOVA) to indicate linear (additivity) or statistically significant ($p<0.1$) non-linear (antagonism or synergy) mixes of the combinants.

Certain cancer cell lines and their tumor types are listed in Table 16.

TABLE 16

Cancer cell line list

| CELL LINE | TUMOR TYPE |
|---|---|
| DOHH-2 | Lymphoma- B cell |
| DU-4475 | Breast |
| EOL-1 | Leukemia |
| Farage | Lymphoma- non-hodgkins B cell |
| GRANTA-519 | Lymphoma- mantle cell |
| HBL-1 | Lymphoma-B cell |
| HCC2935 | Lung-NSCLC |
| HCC95 | Lung-NSCLC |
| HH | Lymphoma-T cell |
| HT-115 | Colorectal |
| JHH-2 | Liver |
| KARPAS-299 | Lymphoma- non-hodgkins B cell |
| KARPAS-422 | Lymphoma- non-hodgkins B cell |
| KARPAS-620 | Multiple Myeloma |
| KASUMI-1 | Leukemia, AML |
| KE-97 | Gastric |
| KELLY | Neuroblastoma |
| KG-1 | Leukemia, AML |
| KG-1a | Leukemia, AML |
| KMS-20 | Multiple Myeloma |
| KMS-21-BM | Multiple Myeloma |
| KMS-34 | Multiple Myeloma |
| LC-1F | Lung-NSCLC |
| LCLC-103H | Lung-NSCLC |
| LU-134-A | Lung--SCLC |
| LU-139 | Lung--SCLC |
| MDST8 | Colorectal |
| ML-1 | Thyroid |
| MOLM-13 | Leukemia-CML |
| MV-4-11 | Leukemia |
| NCI-H1048 | Lung--SCLC |
| NCI-H1650 | Lung-NSCLC |
| NCI-H1694 | Lung--SCLC |
| NCI-H1944 | Lung-NSCLC |
| NCI-H1993 | Lung-NSCLC |
| NCI-H2126 | Lung-NSCLC |
| NCI-H2141 | Lung--SCLC |
| NCI-H2171 | Lung--SCLC |
| NCI-H2228 | Lung-NSCLC |
| NCI-H446 | Lung--SCLC |
| NCI-H820 | Lung-NSCLC |
| NCI-H841 | Lung--SCLC |
| NCI-H929 | Multiple Myeloma |
| NOMO-1 | Leukemia, AML |
| OCI-Ly3 | Lymphoma- B cell |
| OCI-Ly7 | Lymphoma- B cell |
| OPM-2 | Lymphoma- B cell |
| OVK18 | Lymphoma- B cell |
| PC-3 | Prostate |
| PC-9 | Lung-NSCLC |
| RL | Lymphoma- B cell |
| RPMI-8226 | Lymphoma- B cell |
| SU-DHL-10-epst | Lymphoma- B cell |
| TE-1 | Esophageal |
| TE-14 | Esophageal |
| THP-1 | Leukemia, AML |
| U-2932 | Lymphoma- B cell |
| WM-266-4 | Skin |
| WSU-NHL | Lymphoma- B cell |
| ZR-75-1 | Breast |

A. Double Combinations

Compound (2) was tested against a panel of 60 cancer cell lines (see Table 16) alone and in combination with a panel of cytotoxic and non-cytotoxic SOC agents. The 60 cancer cell lines represent lines derived from breast cancer, prostate cancer, lung cancer, acute myeloid leukemia (AML), myeloma and other cancers. Cells were removed from liquid nitrogen storage, thawed and expanded in appropriate growth media. Once expanded, cells were seeded in 384- well tissue culture treated plates at 500 cells per well. After 24 hours, cells were treated for either 0 hours or treated for 144 hours with Compound (2) in combination with genotoxin: bleomycin (radio mimetic), doxorubicin (topoisomerase II inhibitor), etoposide (topoisomerase II inhibitor), carboplatin (DNA crosslinker), BMN-673 (PARP inhibitor), and tarceva (EGFR inhibitor)). At the end of either 0 hours or 144 hours, cell status was analyzed using ATPLite (Perkin Elmer) to assess the biological response of cells to drug combinations.

Figure 23:
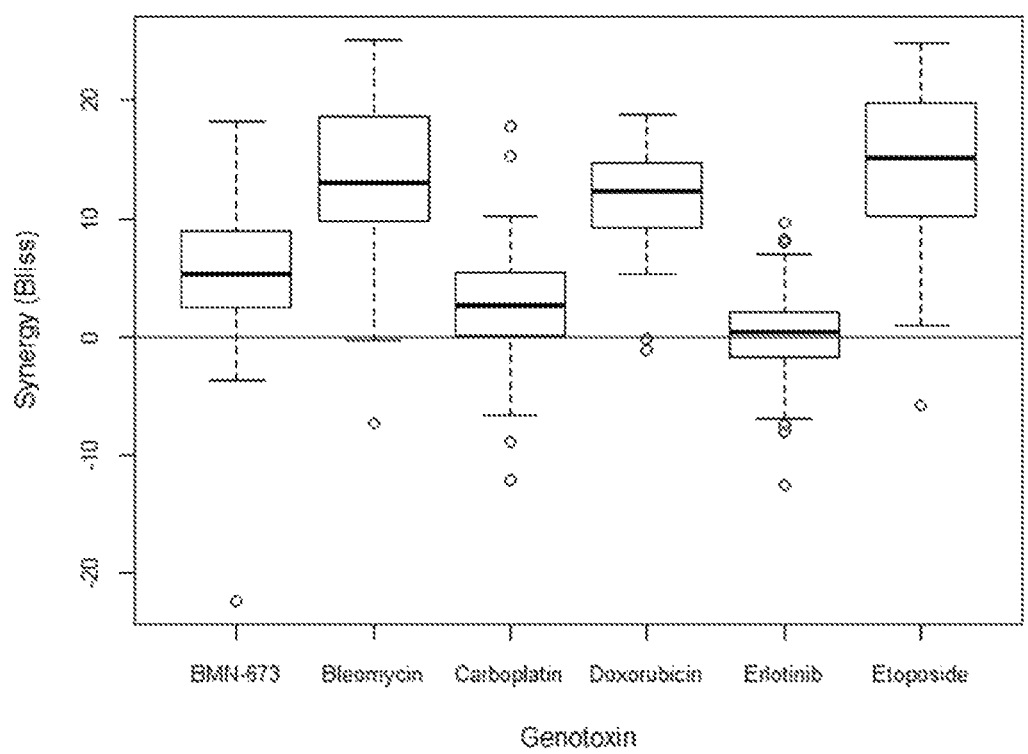
FIG. 23 shows a diagram summarizing Bliss analysis of Compound (2) in combination with a panel of cytotoxic and non-cytotoxic agents.
Figure 24:
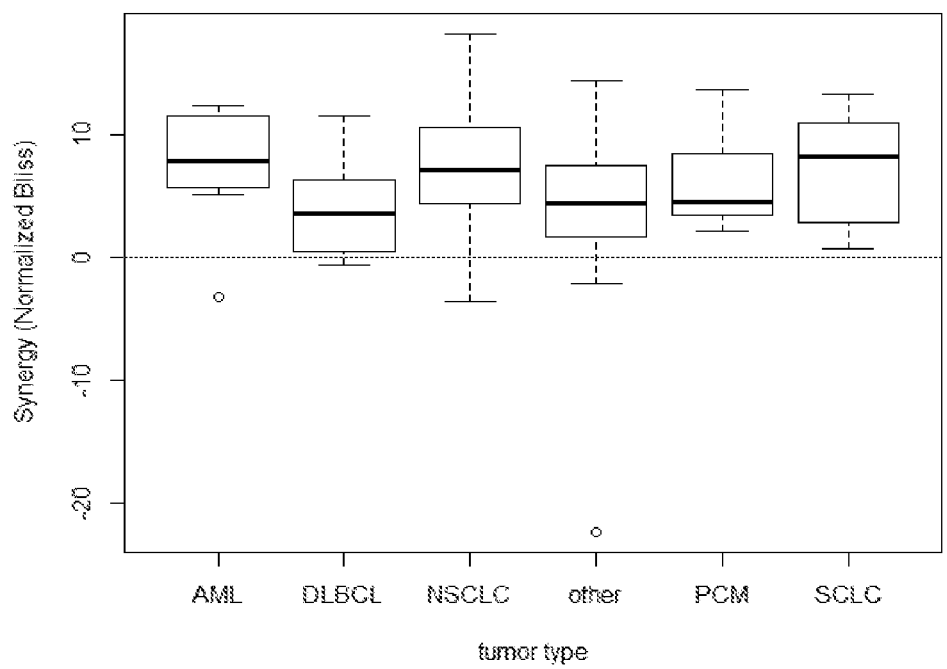
FIG. 24 shows a diagram summarizing Bliss analysis of Compound (2) in combination with BMN-673 by tumor type.
Figure 25:
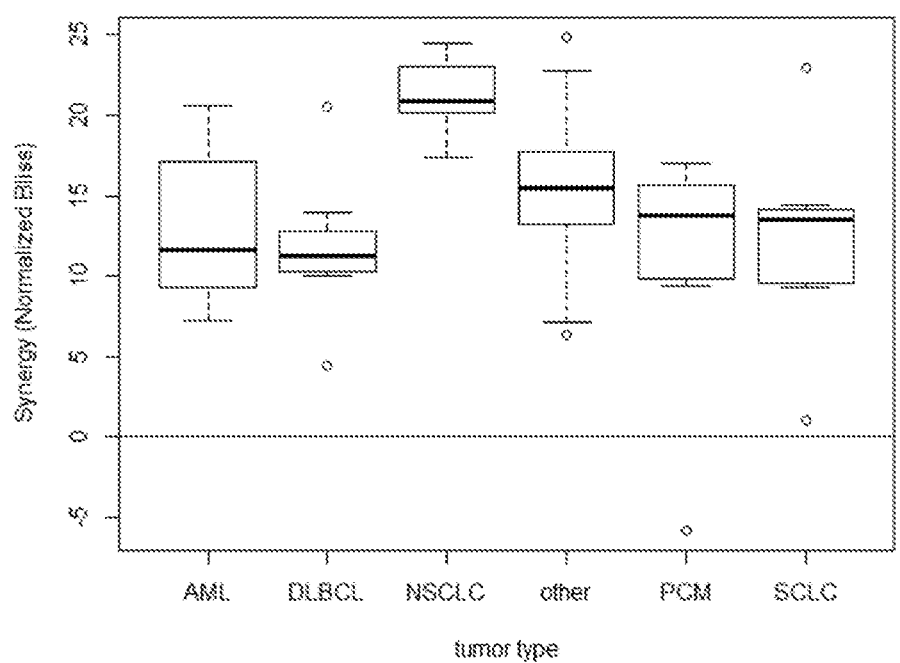
FIG. 25 shows a diagram summarizing Bliss analysis of Compound (2) in combination with etoposide by tumor type.
Figure 26:
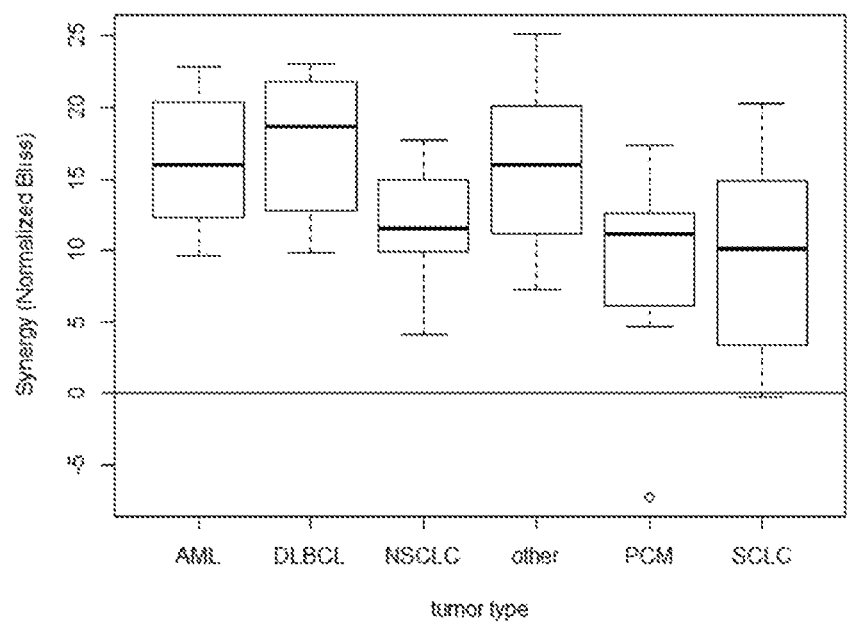
FIG. 26 shows a diagram summarizing Bliss analysis of Compound (2) in combination with bleomycin by tumor type.
Figure 27:
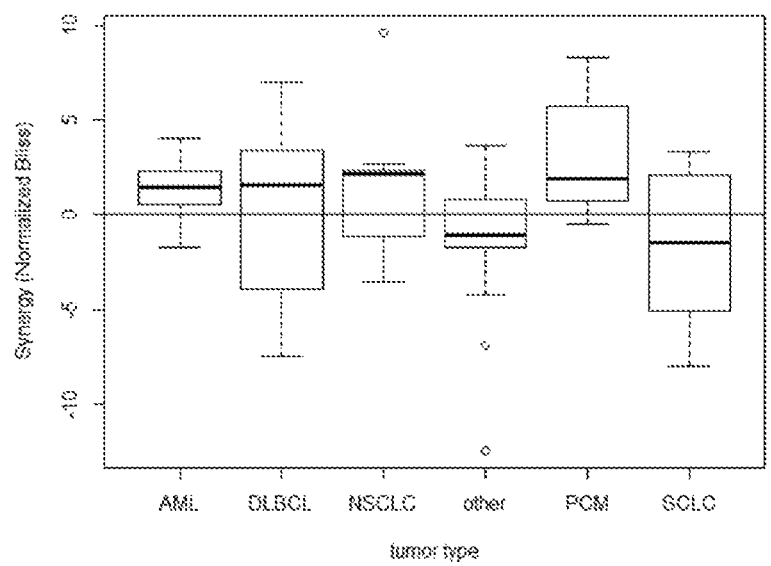
FIG. 27 shows a diagram summarizing Bliss analysis of Compound (2) in combination with erlotinib by tumor type.
Figure 28:
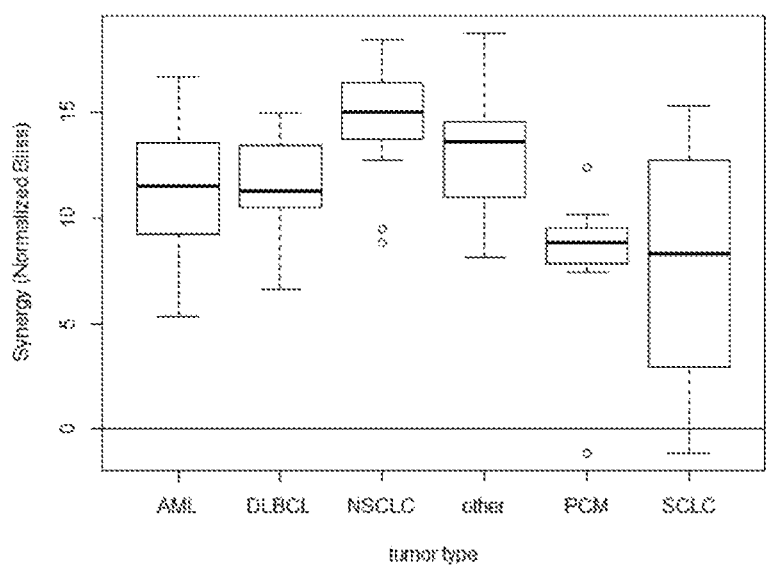
FIG. 28 shows a diagram summarizing Bliss analysis of Compound (2) in combination with doxorubicin by tumor type.
Figure 29:
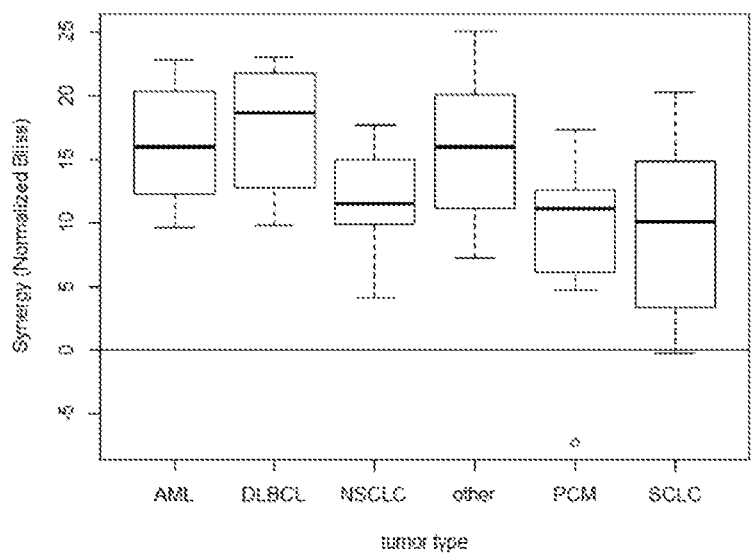
FIG. 29 shows a diagram summarizing Bliss analysis of Compound (2) in combination with bleomycin by tumor type.
Figure 30:
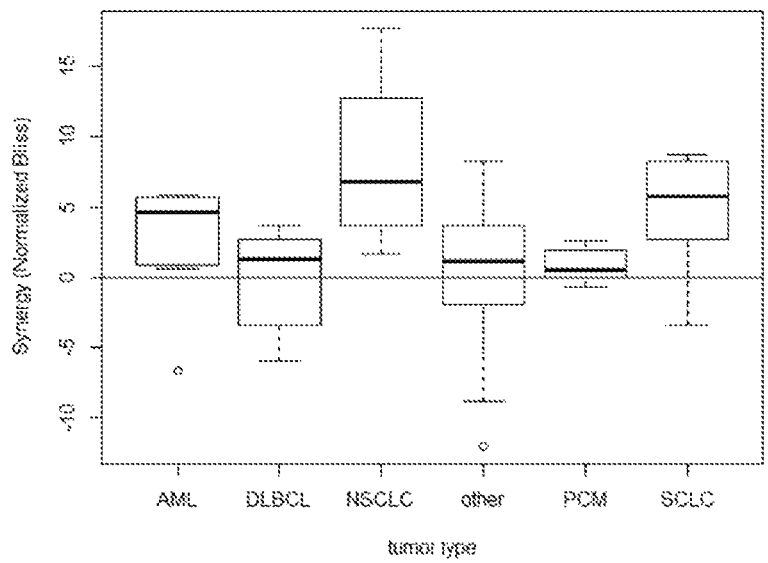
FIG. 30 shows a diagram summarizing Bliss analysis of Compound (2) in Combination with carboplatin by tumor type.

Compound (2) demonstrated strong synergy with several agents tested: etoposide (topoisomerase inhibitor), doxorubicin (DNA intercalator), and bleomycin (radiomimetic) (FIG. 23). Some synergy was seen in combination with BMN-673 (PARP inhibitor) and carboplatin DNA-repair inhibitor). Additivity was seen with erlotinib (EGFR inhibitor) (FIG. 23). When analyzed by cancer cell line type, Compound (2) and BMN-673 demonstrated greatest activity against AML. Compound (2) and etoposide, while highly active against most lines, was particularly active against non-small cell lung cancer lines as was Compound (2) and doxorubicin (see below). Bliss synergy data of Compound (2) in various tumor types (acute myeloid leukemia (AML), diffuse large B-cell lymphoma (DLBCL), non-small cell lung cancer (NSCLC), plasma cell myeloma (PCM), small cell lung cancer (SCLC)) are shown in FIGS. 24-30: combination of Compound (2) with BMN-673 in FIG. 24; combination of Compound (2) with etoposide in FIG. 25; combination of Compound (2) with bleomycin in FIG. 26; combination of Compound (2) with erlotinib in FIG. 27; combination of Compound (2) with doxorubicin in FIG. 28; combination of Compound (2) with bleomycin in FIG. 29; combination of Compound (2) with carboplatin in FIG. 30.

Combinations of Compound (2) and doxorubicin or epirubicin (DNA intercalator) were tested against breast cancer cell lines (Tables 17 and 18), with a comparison between wild-type and mutant lines being a focus of the study. Independent of plating density, sensitivity to doxorubicin alone, or BRCA status, the combination of doxorubicin and Compound (2) was strongly synergistic in all five cell lines and at both Compound (2) concentrations tested (Bliss analysis). The >3-fold shift in IC50 of the combination of doxorubicin and Compound (2) compared to doxorubicin alone also indicates a high degree of synergy. A similar experiment using Doxorubicin or epirubicin in combination with Compound (2) in the DU4475 breast cancer line demonstrated strong synergy (Bliss analysis) (Table 18).

The combination of the Compound (2) and doxorubicin or epirubicin was strongly synergistic in all triple-negative breast cancer cell lines evaluated, independent of BRCA status or plating density.

TABLE 17

Summary of Combinations with Compound (2) and Doxorubicin in Triple Negative Breast Cancer Cell Lines

| Cell Line | Plating Density | BRCA status | Average Bliss score | Doxorubicin IC50 (μM) | Maximum IC50 Shift (fold) |
|---|---|---|---|---|---|
| HCC-1395 | 5000 | Mutant | 11.1 | 0.5 | 4.6 |
| HCC-1599 | Unknown | Mutant | 14.3 | 0.2 | 4.3 |
| HCC-1937 | 5000 | Mutant | 16.6 | 0.2 | 3.7 |
| HCC-1937 | 20000 | Mutant | 15.6 | 0.6 | 3.9 |
| MDA-MB-436 | 5000 | Mutant | 14.5 | 0.7 | 9.1 |
| MDA-MB-436 | 20000 | Mutant | 14.4 | 0.3 | 4.7 |
| MDA-MB-468 | 5000 | Wild-type | 23.1 | 0.02 | 19 |
| MDA-MB-468 | 20000 | Wild-type | 24.7 | 0.04 | 13 |

TABLE 18

Summary of Combinations with Compound (2) and Doxorubicin or Epirubicin in DU4475 Cells

| Drug | Average Bliss score |
|---|---|
| Doxorubicin | 31.9 |
| Epirubicin | 33.3 |

B. Double and Triple Combinations with and without Radiation (2 Gy)

The following SOC agents were tested in double combinations with Compound (1): etoposide (a topoisomerase inhibitor that induces DSBs), cisplatin (DNA cross-linker), carboplatin (DNA cross-linker), fluorouracil (5-FU, antimetabolite that inhibits thymidylate synthase), paclitaxel (mitotic inhibitor that binds to tubulin), cetuximab (EGFR monoclonal antibody), and radiation. Other than the combination of radiation and Compound (1), the strongest interaction for the double combination studies was etoposide and Compound (1) in A549 cells (Table 19) and Compound (1) and etoposide in ESO26 (Table 20). These findings were confirmed using the Bliss Additivity model (Table 21). Other combinations demonstrated additivity with rare examples of antagonism. While there is not total agreement in the various lines tested, (as detailed in the other sections) the majority agree and the conclusions arrived at are common to each. The same experiment performed using OE19 cells showed a more complex interaction pattern in the absence of radiation. A significantly enhanced effect was seen when radiation was added to the combinations, reinforcing the strong relationship between DNA damage (DSB and SSB) and DNA-PK inhibition. The cancer cell lines in Table 19 indicate: ESO26—gastroesophageal junction cancer, OE19—gastroesophageal junction cancer, DMS-53—SCLC, A549—lung cancer, colo205—colon cancer, H460—lung cancer, H2009—lung cancer, FaDu—pharynx cancer, Miapaca2—pancreatic cancer, HFL1—human fetal lung fibroblast.

The combination of the Compound (2) and doxorubicin or epirubicin was strongly synergistic in all triple-negative breast cancer cell lines evaluated, independent of BRCA status or plating density.

In the triple SOC combination experiments, synergy was demonstrated with the combination of etoposide, cisplatin, and Compound (1) in the DMS-53 and A549 cell lines. The major driver for this synergy was the combination of etoposide with Compound (1). Paclitaxel, cisplatin, and Compound (1) was additive in the A549 cell line, while cisplatin, 5-FU and Compound (1) were synergistic in the Colo205 cell line. A highly significant reduction in cell viability was observed upon the addition of radiation to these combinations, principally driven by the contribution of Compound (1). Compound (2) demonstrated the same combination outcomes on cell viability with SOC combinants (using a smaller set of cancer cell lines) when compared to Compound (1).

Primary human tumors tested in vitro may provide a better indicator of efficacy of DNA PK inhibition than immortalized cancer cell lines due to their increased heterogeneity and closer proximity to the patient tumor from which they were derived. A panel of primary human tumors (NSCLC, pancreatic, esophageal, gastric, etc.) was treated with Compound (1) to determine the effectiveness of DNA-PK inhibition in combination with radiation, bleomycin (a radiomimetic agent that induces DSBs), doxorubicin (DNA intercalator), cisplatin, carboplatin, etoposide, paclitaxel, or 5-FU.

Compound (1) (10× and 30×IC50) was administered in combination with a dose range of bleomycin or radiation. Dissociated cells from mouse-passaged tumors were cultured for 6 days after combination exposure and then assessed for viability using the Cell Titer-Glo assay. The Bliss Additivity statistical model was used to determine the degree of synergy, additivity, or antagonism of each combination treatment.

Figure 31:
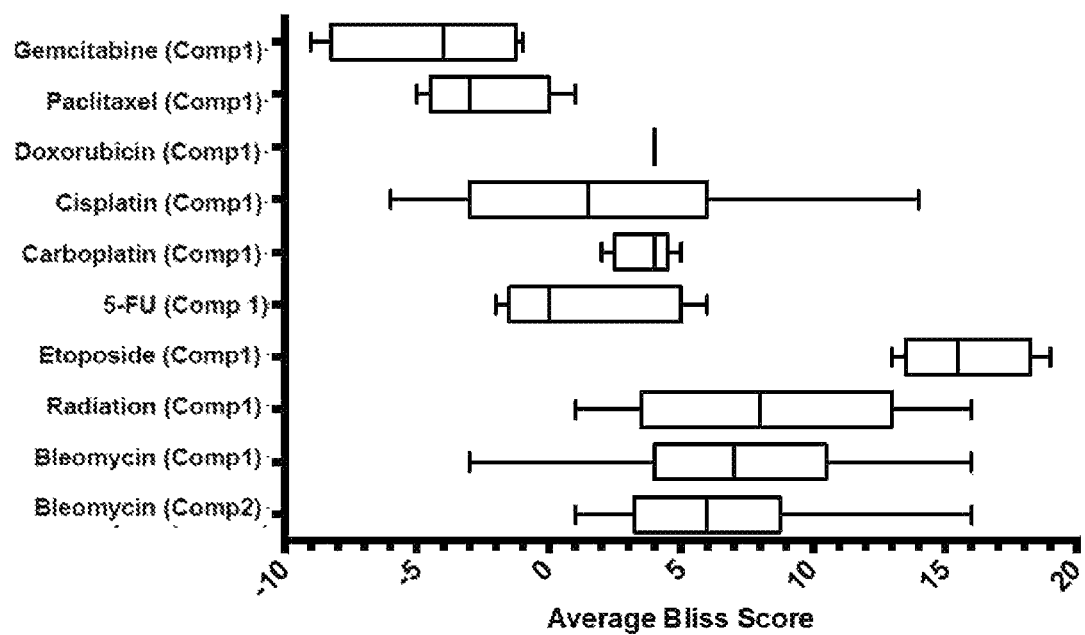
FIG. 31 shows a diagram summarizing Bliss analysis of Compound 1 or Compound 2 and standard of care combinations in primary human tumor chemosensitivity assays.

The combination of Compound (1) and bleomycin or radiation was additive or synergistic in all tumors tested (29/29) (see FIG. 31). In addition, strong synergy was seen in nearly a third of both bleomycin (9/29) and radiation (3/8) treated tumors in combination with Compound (1). Similarly, Compound (2) was tested in combination with a dose range of bleomycin in a smaller subset of tumors (gastric, pancreatic). The combination of Compound (2) and bleomycin was additive or synergistic in all tumors tested (20/20) and strongly synergistic in a subset of those (3/20) (see FIG. 31). These data suggest that a DNA-PK inhibitor in combination with radiation therapy may be more broadly effective than the standard of care alone.

A panel of primary tumors was also treated with Compound (1) in combination with a variety of chemotherapeutic agents (gemcitabine, paclitaxel, cisplatin, carboplatin, 5-FU,

TABLE 19

Effect of Compound (1) in Combination with Genotoxic Agents on the Viability of Cancer Cell Lines

| Cell Line | Combination with Compound (1) | | | | | | Synergy or Antagonism | |
| | Cisplatin | Etoposide | Carboplatin | Paclitaxel | 5-FU | Cetuximab | No Radiation | Plus Radiation (2 Gy) |
|---|---|---|---|---|---|---|---|---|
| A549 | ✓ | | | | | | Additivity | ND |
|  |  | ✓ | | | | | Strong Synergy | ND |
|  |  |  | ✓ | | | | Antagonism | ND |
|  |  |  |  |  |  |  | Synergy | Plus |
|  |  |  |  |  | ✓ |  | Additivity | Additivity, Plus |
|  | ✓ | ✓ | | | | | Strong Synergy | Strong Synergy, Plus |
|  | ✓ | | | ✓ | | | Additivity | Synergy, Plus |
| H460 |  |  |  |  |  |  | Synergy | Plus |
| H2009 |  |  |  |  |  |  | Additivity | Plus |
| Colo205 | ✓ |  |  |  | ✓ |  | Synergy | Synergy, Plus |
| DMS-53 | ✓ | ✓ |  |  |  |  | Strong Synergy | N/A |
| OE19 | ✓ |  |  | ✓ |  |  | Mix | Synergy, Plus |
|  |  |  | ✓ |  |  |  | Antagonism | Synergy*, Plus |
|  |  |  |  |  | ✓ |  | Additivity | Synergy*, Plus |
| FaDu |  |  |  |  |  | ✓ | Additivity | Additivity, Plus |
|  |  |  |  |  |  |  | Synergy | Plus |
| HFL1 | ✓ |  |  |  |  |  | Additive | ND |
|  |  | ✓ |  |  |  |  | Synergy | ND |
|  | ✓ |  |  |  | ✓ |  | Additivity | Additivity, Plus |
|  |  |  |  | ✓ |  |  | Additivity | ND |
|  |  |  |  |  |  |  | Additivity | No effect |

ND = Not Determined, N/A = Not Applicable: etoposide is a radiomimetic., Plus = enhanced effect of radiation.
*Viability reduction driven predominantly by Compound (1) plus radiation.

TABLE 20

Effect of Compound (2) in Combination with Genotoxic Agents on the Viability of the ESO26 (GEJ) Cancer Cell Line (Mixtures analysis)

| 1. Combinations with Comp 2 | 2. No Radiation | 3. Plus Radiation |
|---|---|---|
| Cisplatin, 5-FU | Synergy; Comp. 2 with 5-FU | Significant reduction in cell survival driven by Comp. 2 and radiation |
| Carboplatin, Paclitaxel | Additive overall | Significant reduction in cell survival driven by Comp. 2 and radiation |
| Etoposide | Significant synergy | Not applicable |

Based on IC$_{50}$ of 20 μM for Comp. 2, 50 μM for carboplatin, 1.5 μM for cisplatin, 3 nM for paclitaxel, 0.6 μM for etoposide and 20 μM for 5-FU.
Not applicable: etoposide is a radiomimetic.

TABLE 21

Effect of Compound (2) in Combination with Etoposide on the Viability of Cancer Cell Lines (Bliss analysis)

| Cell Line | Average Bliss Score |
|---|---|
| A549 | 27.3 (n = 1) |
| ESO26 | 43.2 ± 6.5 (n = 3) |
| HFL1 | 8.7 ± 5.6 (n = 3) |

C. Effect of the Combination of Compound (1) or (2) and SOC in Primary Tumor Chemosensitivity Assays (TCA)

etoposide) commonly used in the treatment of the tumor types tested. Additivity was observed in most tumors treated with Compound (1) and either gemcitabine, (2/4) paclitaxel (1/5), 5-FU (5/5), or doxorubicin (1/1). However, antagonism was seen in some tumors with gemcitabine (2/4) and paclitaxel (1/5). Synergy or additivity was observed in nearly all tumors with both carboplatin (5/5) and cisplatin (9/10), but one tumor showed antagonism with cisplatin. The combination of Compound (1) and etoposide showed strong synergy in all tumors tested (4/4). These TCA results were consistent with the combination data generated using cancer cell lines. Overall, these data suggest that a selective DNA-PK inhibitor may provide added benefit to cancer patients receiving standard of care treatment in a variety of clinical applications.

Example 14. Effect of Compound (1) on Clonogenic Survival of Irradiated Cancer Cell Lines The clonogenic cell survival assay measures the ability of a cell to proliferate indefinitely, thereby retaining its self-renewing ability to form a colony (i.e., clone). This assay has been a mainstay in radiation oncology for decades and was used to determine the effect of Compound (1) on the clonogenicity of a panel of cell lines across multiple tumor types following radiation. Compound (1) in combination with radiation was shown to be very efficacious in decreasing the clonogenicity of all cancer cell lines tested with dose enhancement factors (DEF, the difference in colony number at surviving fraction 0.1) ranging from 2.5 to >5. Miapaca2 cells exhibited the lowest DEF (2.5), while in FaDu cells, the combination of Compound (1) and radiation completely eliminated colony formation with as little as 0.5 Gy and showed a DEF of >8. A DEF greater than 1.5 is generally considered to be clinically meaningful; therefore, by these standards, Compound (1) would be characterized as a strong radio-enhancing agent. These data are consistent with the previous cell viability data in suggesting that a broad responder population can be expected in cancer patients treated with Compound (1) in combination with radiation.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All references provided herein are incorporated herein in its entirety by reference. As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997.

What is claimed is:

1. A method of potentiating a therapeutic regimen for the treatment of breast cancer, colorectal cancer, gastric-esophageal cancer, fibrosarcoma, glioblastoma, hepatocellular carcinoma, head and neck squamous cell carcinoma, melanoma, lung cancer, pancreatic cancer or prostate cancer in a patient comprising administering to said patient an effective amount of a co-crystal comprising a compound of the formula

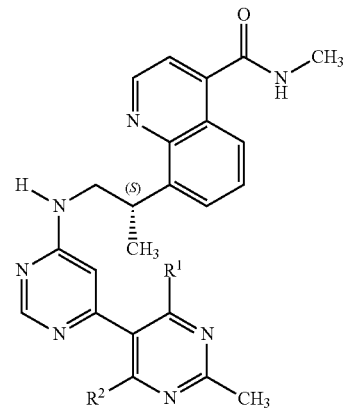

and
a co-crystal former, wherein the co-crystal former is adipic acid, wherein each of $R^1$ and $R^2$ is independently hydrogen or deuterium.

2. The method of claim 1, wherein a molar ratio of the adipic acid to the compound of formula I is about 1 to 2.

3. The method of claim 2, wherein the compound of formula I is (S)—N-methyl-8-(1-((2'-methyl-[4,5'-bipyrimidin]-6-yl)amino)propan-2-yl)quinoline-4-carboxamide.

4. The method of claim 2, wherein the compound of formula I is (S)—N-methyl-8-(1-((2'-methyl-4',6'-dideutero-[4,5'-bipyrimidin]-6-yl)amino)propan-2-yl)quinoline-4-carboxamide.

5. The method of claim 3, wherein the compound has X-ray powder diffraction peaks at about 6.46, 7.91, 11.92, 12.26, 12.99, 14.19, 18.68, and 19.07° 2-Theta.

6. The method of claim 3, wherein the compound has a DSC peak in its DSC thermogram at about 195° C. and about 245° C.

7. The method of claim 4, wherein the compound has a DSC peak in its DSC thermogram at about 195° C. and about 245° C.

8. The method of claim 4, wherein the compound has X-ray powder diffraction peaks at about 6.46, 7.91, 11.92, 12.26, 12.99, 14.19, 18.68, and 19.07° 2-Theta.

9. The method of claim 1, wherein the compound is administered in a pharmaceutical composition.

10. The method of claim 1, wherein the therapeutic regimen comprises radiation therapy or chemotherapy, or both radiation therapy and chemotherapy.

11. The method of claim 1, wherein the co-crystal is administered with etoposide, doxorubicin, daunorubicin, epirubicin or bleomycin.

12. A method of treating breast cancer, colorectal cancer, gastric-esophageal cancer, fibrosarcoma, glioblastoma, hepatocellular carcinoma, head and neck squamous cell carcinoma, melanoma, lung cancer, pancreatic cancer or prostate cancer in a patient comprising administering to said patient an effective amount of a co-crystal comprising a compound of the formula

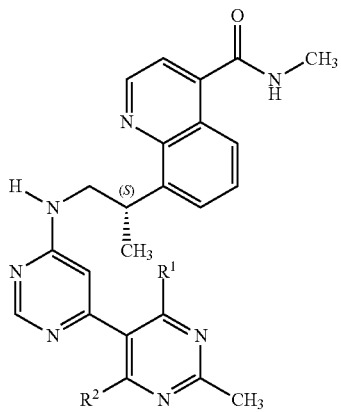

(I)

and a co-crystal former, wherein the co-crystal former is adipic acid, wherein each of R¹ and R² is independently hydrogen or deuterium.

13. The method of claim 12, wherein a molar ratio of the adipic acid to the compound of formula I is about 1 to 2.

14. The method of claim 13, wherein the compound of formula I is (S)—N-methyl-8-(1-((2'-methyl-[4,5'-bipyrimidin]-6-yl)amino)propan-2-yl)quinoline-4-carboxamide.

15. The method of claim 13, wherein the compound of formula I is (S)—N-methyl-8-(1-((2'-methyl-4',6'-dideutero-[4,5'-bipyrimidin]-6-yl)amino)propan-2-yl)quinoline-4-carboxamide.

16. The method of claim 14, wherein the compound has X-ray powder diffraction peaks at about 6.46, 7.91, 11.92, 12.26, 12.99, 14.19, 18.68, and 19.07° 2-Theta.

17. The method of claim 14, wherein the compound has a DSC peak in its DSC thermogram at about 195° C. and about 245° C.

18. The method of claim 15, wherein the compound has a DSC peak in its DSC thermogram at about 195° C. and about 245° C.

19. The method of claim 15, wherein the compound has X-ray powder diffraction peaks at about 6.46, 7.91, 11.92, 12.26, 12.99, 14.19, 18.68, and 19.07° 2-Theta.

20. The method of claim 12, wherein the compound is administered in a pharmaceutical composition.

21. The method of claim 12, wherein the co-crystal is administered with an additional therapeutic agent, wherein the additional therapeutic agent comprises radiation therapy or chemotherapy, or both radiation therapy and chemotherapy.

22. The method of claim 12, wherein the co-crystal is administered with etoposide, doxorubicin, daunorubicin, epirubicin or bleomycin.

* * * * *